United States Patent
Kellogg et al.

(10) Patent No.: US 6,706,519 B1
(45) Date of Patent: Mar. 16, 2004

(54) DEVICES AND METHODS FOR THE PERFORMANCE OF MINIATURIZED IN VITRO AMPLIFICATION ASSAYS

(75) Inventors: Gregory J. Kellogg, Cambridge, MA (US); Charles Able, Cambridge, MA (US); Todd Arnold, Glastonbury, CT (US); Bruce L. Carvalho, Watertown, MA (US); Hsin-Chiang Lin, Cambridge, MA (US); Stephen Kieffer-Higgins, Boston, MA (US); Norman F. Sheppard, Bedford, MA (US); Mikayla Kob, Somerville, MA (US); Shari Ommert, Stoneham, MA (US)

(73) Assignee: Tecan Trading AG, Baar (CH)

( * ) Notice: Subject to any disclaimer, the term of this patent is extended or adjusted under 35 U.S.C. 154(b) by 482 days.

(21) Appl. No.: 09/602,394

(22) Filed: Jun. 22, 2000

Related U.S. Application Data

(60) Provisional application No. 60/140,477, filed on Jun. 22, 1999.

(51) Int. Cl.[7] ............................................. C12M 1/34
(52) U.S. Cl. ........................ 435/287.2; 435/286.5; 435/287.3; 435/288.5; 435/288.7; 422/64; 422/82.08
(58) Field of Search ................ 435/286.5, 287.2, 435/287.3, 288.5, 288.7; 422/64, 67, 82.08

(56) References Cited

U.S. PATENT DOCUMENTS

| | | | | |
|---|---|---|---|---|
| 4,515,889 A | * | 5/1985 | Klose et al. | 435/4 |
| 4,683,195 A | | 7/1987 | Mullis et al. | 435/4 |
| 4,683,202 A | | 7/1987 | Mullis | 435/91 |
| 4,988,617 A | | 1/1991 | Landegren et al. | 435/6 |
| 5,304,487 A | | 4/1994 | Wilding et al. | 435/291 |
| 5,545,540 A | | 8/1996 | Mian | 435/91.2 |
| 5,639,428 A | * | 6/1997 | Cottingham | 422/112 |
| 5,674,743 A | * | 10/1997 | Ulmer | 435/287.2 |
| 6,030,581 A | * | 2/2000 | Virtanen | 422/68.1 |
| 6,063,589 A | | 5/2000 | Kellogg et al. | 435/24 |
| 6,143,248 A | * | 11/2000 | Kellogg et al. | 422/72 |
| 6,391,541 B1 | * | 5/2002 | Petersen et al. | 435/5 |
| 2002/0177144 A1 | * | 11/2002 | Remacle et al. | 435/6 |

FOREIGN PATENT DOCUMENTS

| | | | |
|---|---|---|---|
| EP | 0 693 560 | 1/1996 | |
| JP | 63085428 | 4/1998 | |
| WO | WO92/22058 | 11/1993 | ............... B01J/7/00 |
| WO | WO93/22053 | 11/1993 | ............... B01L/3/00 |
| WO | WO97/21090 | 6/1997 | ............ G01N/21/07 |
| WO | WO98/07019 | 2/1998 | ............ G01N/21/07 |
| WO | WO98/28623 | 7/1998 | ............ G01N/33/543 |
| WO | WO98/53311 | 11/1998 | ............ G01N/33/00 |

OTHER PUBLICATIONS

Birnboim & Doly, 1979, Nucl. Acids Res. 7:1513–1522.
Wilding et al., 1994 Clin Chem. 40:43–47.
Kopp et al. 1998 Science 280:1046.
Larson 1997, Micro Structure Bull. 1:3.
Duffy et al. 1998, Anal. Chem 70:49744984.

\* cited by examiner

*Primary Examiner*—David A. Redding
(74) *Attorney, Agent, or Firm*—McDonnell Boehnen Hulbert & Berghoff

(57) ABSTRACT

This invention relates to methods and apparatus for performing microanalytic and microsynthetic analyses and procedures. The invention provides a microsystem platform and a micromanipulation device for manipulating the platform that utilizes the centripetal force resulting from rotation of the platform to motivate fluid movement through microchannels. The invention specifically provides devices and methods for performing miniaturized in vitro amplification assays such as the polymerase chain reaction. Methods specific for the apparatus of the invention for performing PCR are provided.

30 Claims, 35 Drawing Sheets

653 base insert

DEVICES AND METHODS FOR THE PERFORMANCE OF MINIATURIZED IN VITRO AMPLIFICATION ASSAYS

This application claims priority to U.S. Provisional Application Ser. No. 60/140,477, filed Jun. 22, 1999, the disclosure of which is explicitly incorporated by reference herein.

BACKGROUND OF THE INVENTION

1. Field of the Invention

This invention relates to methods and apparatus for performing microanalytic and microsynthetic analyses and procedures. In particular, the invention relates to microminiaturization of genetic, biochemical and bioanalytic processes. Specifically, the present invention provides devices and methods for the performance of integrated and miniaturized sample preparation, nucleic acid amplification, and nucleic acid detection assays. These assays may be performed for a variety of purposes, including but not limited to forensics, life sciences research, and clinical and molecular diagnostics. The invention may be used on a variety of liquid samples of interest, including bacterial and cell cultures as well as whole blood and processed tissues. Methods for performing any of a wide variety of such microanalytical or microsynthetic processes using the Microsystems apparatus of the invention are also provided.

2. Background of the Related Art

Extraction and isolation of DNA from host cells is a cornerstone of modern molecular biology. One type of DNA, bacterial plasmid DNA has been particularly useful as a convenient vector for the insertion of genetic material into bacterial, yeast and mammalian cells. DNA isolated from an organism is inserted by being contiguously and covalently linked to plasmid DNA and is then introduced into a cell, such as a bacterial cell, and allowed to multiply, thereby creating large copy numbers of the plasmid in each cell. These plasmids may advantageously be harvested to provide a sufficient amount of DNA (typically on the order of several micrograms, although up to milligram quantities can be produced on an industrial scale) for a variety of experimental or therapeutic purposes. The harvesting of plasmid DNA, defined as its removal from cells and isolation from the genomic DNA content of the cells, has growing utility in life sciences research, diagnostics, therapeutics and other applications.

Currently, the extraction and isolation of DNA is either performed manually or through the use of robotic sample preparation stations. In either case, a variety of technologies and materials are used (see, for example, QIAamp DNA Mini Kit and QIAamp DNA Blood Mini Kit Handbook, 1999, Qiagen GmbH, Max-Volmer-Strasse 4, 40724 Hildren, Germany; Birnboim & Doly, 1979, *Nucl. Acids Res.* 7: 1513–1522). Typically, cells are first incubated in a surfactant (detergent) solution, in some cases containing protein digesting enzymes such as Protease or Proteinase K. These lyse the cells, thereby releasing the DNA into solution. This is frequently performed under alkaline conditions, to destabilize nucleases and hydrolyze contaminating RNA. The DNA must then be separated from other cell constituents, which is performed using a number of different separation protocols, including, for example, selective precipitation of proteins and other cell debris, organic chemical extraction (using phenol and chloroform), and DNA affinity column chromatography. Plasmid DNA must also be isolated from contaminating cellular (bacterial genomic DNA). Filtration methods can produce a plasmid DNA solution, but the solutions required to solvate DNA are usually inappropriate for the desired final application of the DNA. As a consequence, plasmid DNA is removed from these solutions by ethanol precipitation, or solid-phase separation is used, which often requires further changes in solvent pH and salt concentration (especially for affinity binding methods using glass or silica). The technologies required for these steps include pipetting, pumping, filtration, washing, and centrifugation, requiring an expensive suite of devices and skilled operators thereof. The additional requirements of automated systems include sample transfer and robotics for the handling of sample containers.

This discussion illustrates the need in the art for more efficient, rapid, inexpensive automated methods and devices for performing DNA sample preparation, particularly plasmid DNA preparation.

In the field of integrated genetic analysis, some progress has been made in the integration of sample preparation, PCR, and detection via real-time fluorescence or hybridization methods (Anderson et al., 1998, "Advances in Integrated Genetic Analysis," in *Proc. Micro Total Analysis '98*, Harrison & van den Berg, eds., Kluwer: Amsterdam, pp.11–16). These systems rely on macroscopic fluid handling systems such as pumps and valves that must be interfaced with the microfluidic devices within which fluids are processed.

However, there exists a need for devices and methods capable of processing cell cultures for harvesting DNA, particularly plasmid DNA.

In the biological and biochemical arts, analytical procedures frequently require incubation of biological samples and reaction mixtures at temperatures greater than ambient temperature. Moreover, many bioanalytical and biosynthetic techniques require incubation at more than one temperature, either sequentially or over the course of a reaction scheme or protocol.

One example of such a bioanalytical reaction is the polymerase chain reaction. The polymerase chain reaction (PCR) is a technique that permits amplification and detection of nucleic acid sequences. See U.S. Pat. Nos. 4,683,195 to Mullis et al. and 4,683,202 to Mullis. This technique has a wide variety of biological applications, including for example, DNA sequence analysis, probe generation, cloning of nucleic acid sequences, site-directed mutagenesis, detection of genetic mutations, diagnoses of viral infections, molecular "fingerprinting," and the monitoring of contaminating microorganisms in biological fluids and other sources. The polymerase chain reaction comprises repeated rounds, or cycles, of target denaturation, primer annealing, and polymerase-mediated extension; the reaction process yields an exponential amplification of a specific target sequence.

Methods for miniaturizing and automating PCR are desirable in a wide variety of analytical contexts, particularly under conditions where a large multiplicity of samples must be analyzed simultaneously or when there is a small amount of sample to be analyzed.

In addition to PCR, other in vitro amplification procedures, including ligase chain reaction as disclosed in U.S. Pat. No. 4,988,617 to Landegren and Hood, are known and advantageously used in the prior art. More generally, several important methods known in the biotechnology arts, such as nucleic acid hybridization and sequencing, are dependent upon changing the temperature of solutions containing sample molecules in a controlled fashion. Automation and miniaturization of the performance of these methods are desirable goals in the art.

Mechanical and automated fluid handling systems and instruments produced to perform automated PCR have been disclosed in the prior art.

U.S. Pat. No. 5,304,487, issued Apr. 19, 1994 to Wilding et al. teach fluid handling on microscale analytical devices.

International Application, Publication No. WO93/22053, published Nov. 11, 1993 to University of Pennsylvania disclose microfabricated detection structures.

International Application, Publication No. WO93/22058, published Nov. 11, 1993 to University of Pennsylvania disclose microfabricated structures for performing polynucleotide amplification.

Wilding et al., 1994, *Clin. Chem.* 40: 43–47 disclose manipulation of fluids on straight channels micromachined into silicon.

Kopp et al., 1998, *Science* 280: 1046 discloses microchips for performing in vitro amplification reactions using alternating regions of different temperature.

One drawback of the synthetic microchips disclosed in the prior art for performing PCR and other temperature-dependent bioanalytic reactions has been the difficulty in designing systems for moving fluids on the microchips through channels and reservoirs having diameters in the 10–100 $\mu$m range. This is due in part to the need for high-pressure pumping means for moving fluid through the small sizes of the components of these microchips. These disabilities of the prior art microchips limits the usefulness of these devices for miniaturizing and automating PCR and other bioanalytic processes.

Thus, there exists a need in the art for devices and methods that provide integrated sample preparation and analysis, particularly of DNA samples. This need is particularly acute for high throughput analyses, which are currently burdened by the high costs and complexity of automated, typically robotic, systems. Integration of DNA sample preparation and analysis would be particularly useful if it reduced the current need in the art for need for multiple, complex technologies that demand highly-skilled operators. Importantly, for DNA analysis integration of sample preparation and in vitro amplification methods would minimize the possibility of contamination and sample carry-over, which is particularly important in high-sensitivity techniques such as various in vitro amplification reactions used in the art.

Some of the present inventors have developed a microsystem platform and a micromanipulation device to manipulate said platform by rotation, thereby utilizing the centripetal forces resulting from rotation of the platform to motivate fluid movement through microchannels embedded in the microplatform, as disclosed in co-owned U.S. Pat. No. 6,063,589, issued May 16, 2000, and co-owned and co-pending patent applications U.S. Ser. Nos. 08/761,063, filed Dec. 5, 1996; 08/768,990, filed Dec. 18, 1996, now U.S Pat. No. 6,319,469; 08/910,726, filed Aug. 12, 1997, now U.S. Pat. No. 6,143,248; 08/995,056, filed Dec. 19, 1997, now U.S. Pat. No 6,143,147; 09/315,114, filed May 19, 1999; 09/579,492, filed May 12, 2000 and 09/595,239 filed Jun. 16, 2000 (Attorney Docket No. 95,1408-XX), the disclosures of each of which are explicitly incorporated by reference herein.

SUMMARY OF THE INVENTION

This invention provides Microsystems platforms as disclosed in co-owned U.S. Pat. No. 6,063,589, issued May 16, 2000, and co-owned and co-pending patent applications U.S. Ser. Nos. 08/761,063, filed Dec. 5, 1996; 08/768,990, filed Dec. 18, 1996; 08/910,726, filed Aug. 12, 1997; 08/995,056, filed Dec. 19, 1997; 09/315,114, filed May 19, 1999; 09/579,492, filed May 12, 2000 and 09/595,239, filed Jun. 16, 2000 (Attorney Docket No. 95,1408-XX), the disclosures of each of which are explicitly incorporated by reference herein.

The invention provides apparatus and methods for performing microscale processes on a microplatform, whereby fluid is moved on the platform in defined channels motivated by centripetal force arising from rotation of the platform. The Microsystems platform is provided to perform integrated and miniaturized sample preparation, nucleic acid amplification, and nucleic acid detection assays. A first element of the apparatus of the invention is a microplatform that is a rotatable structure, most preferably a disk, the disk comprising fluid (sample) inlet ports, fluidic microchannels, reagent reservoirs, collection chambers, detection chambers and sample outlet ports, generically termed "microfluidic structures". The disk is rotated at speeds from about 1 to about 30,000 rpm for generating centripetal acceleration that enables fluid movement through the microfluidic structures of the platform. The disks of the invention also preferably comprise air outlet ports and air displacement channels. The air outlet ports and in particular the air displacement ports provide a means for fluids to displace air, thus ensuring uninhibited movement of fluids on the disk. The disk, and most preferably a face of the platform, may also contain heating elements for raising the temperature of fluids contained therein to temperatures greater than ambient temperatures. Specific sites on the disk also preferably comprise elements that allow fluids to be analyzed.

A preferred embodiment of the platforms of the invention is a platen that rotates with the microfluidics disk. The platen is most preferably a printed circuit board comprising resistive heating elements, thermoelectric (Peltier) elements, temperature sensors, assay optics and microprocessor and other electronic components. Electrical communication between a rotating platen and stationary power sources, motor controllers, temperature controllers, and computers is most preferably accomplished through a slip-ring assembly. By mounting the microfluidic disk on the platen and rotating both disk and platen together, the distribution and flow rate of fluid throughout the microfluidic structures as well as the temperature of fluid within localized regions of the microfluidics disc can be controlled.

In a preferred embodiment, one face of the microfluidics disk is mounted onto a face of the platen and the temperature of fluids at particular positions within the microfluidics disk is controlled through temperature exchange between the platen and disk. In alternative embodiments, a microfluidic disk is positioned between two platens, each comprising elements that effect temperature exchange between the disk and thermal regulation elements comprising the platens. In a preferred embodiment, the platen is a printed circuit board with resistive heating elements, Peltier elements and temperature sensors embedded therein or affixed thereto. In an alternative embodiment, thermal regulation within the microfluidic disk is achieved by permanently bonding a layer comprising resistive heaters directly to the disk; in this case, fluids within the disk are heated to temperatures greater than ambient temperature with resistive heating elements and cooled to temperatures above or equal to ambient temperature by spinning the disk and through the loss of heat to the environment. As with the platen, electrical communication between this composite disk and power supplies, temperature controllers and computers is most preferably accomplished through a slip-ring assembly.

In a first aspect, the present invention provides devices and methods for the performance of integrated and miniaturized sample preparation for the extraction, isolation, and purification of DNA from cells. In preferred embodiments, the devices and methods of the invention are particularly provided to isolate plasmid DNA from bacterial cells.

The plasmid DNA sample preparation platforms of the invention are provided to perform the following functions: sample processing to free DNA from the bacterial cell; filtration of the resultant solution to remove bacterial cell fragments; application of the solution to a binding matrix using solvent conditions that promote DNA binding to the matrix; washing of bound DNA and replacement of the original solution by a solution that is compatible with further analytical methods; and elution of the DNA from the binding matrix in a suitable solvent. The DNA thus eluted can be isolated, amplified in vitro or sequenced using methods known in the art. The platforms of the invention are provided comprising microfluidic structures that perform plasmid DNA sample preparation as described in further detail below. These microstructures are illustrated for clarity with regard to a single microstructure. However, platforms comprising a multiplicity of such plasmid DNA preparation microfluidic structures are provided by the invention, wherein the microfluidics structures are arrayed on the surface of the platform with a density determined by the size of the platform and the volumetric capacity of the chambers and reservoirs comprising the microfluidic structures as disclosed herein.

In a second aspect, the invention is provided having microfluidics structures as described herein for performing an integrated suite of biochemical processes for accomplishing in vitro amplification reactions. These include sample processing to isolate DNA from bacterial or mammalian cells; sample conditioning to adjust the solution conditions to those appropriate for PCR; mixing of the conditioned sample with PCR reagents, including deoxyribosenuclotides, polymerase enzyme, primers, and appropriate salts, buffers and additives; and thermal cycling to effect PCR.

In certain preferred embodiments, the discs of the invention are provided with a multiplicity of microfluidics structures that enable to platform to process and amplify several samples simultaneously. In these embodiments, multiple copies of an arrangement of microfluidics structures for performing the biochemical reaction suite are arrayed on the disc, and sample input ports or reservoirs provided for each copy, thereby permitting processing of multiple samples. In addition, the portion of the sample DNA to be amplified can be independently, by the choice of amplification primers provided in each of the individual copies of the microfluidics structures arrayed on the disc, thereby permitting amplification "multiplexing" of a particular sample. Alternatively, the same primers can be provided to process in parallel multiple samples for amplification of the same target fragment in the DNA of each sample. Independent thermal cycling profiles, including the temperature used for each step of the amplification cycle, temperature ramp-rates, and hold times, may be individually programmed into the instrument for each of the microfluidics structures or for each of the samples processed.

The invention advantageously permits simultaneous, independent thermal cycling of a multiplicity of different samples, independent amplification of different target fragments from a particular sample, or both. This feature also enables a user to optimize thermal cycling parameters for a single sample or amplicon quickly and in a single experiment, by varying reaction parameters on a plurality of the microfluidics structures arrayed in the disc, thereby simultaneously performing multiple experiments simultaneously. Since particular copies of the microfluidics structures can be arranged in microfluidic isolation from other copies on the platform, portions comprising less than all of the microfluidics structures can be discretely used and the remainder retained for future use.

In alternative embodiments of the platforms of the invention, metering structures as disclosed in co-owned U.S. Pat. No. 6,063,589, issued May 16, 2000 and incorporated by reference herein, are used to distribute aliquots of reagent to each of a multiplicity of mixing structures, each mixing structure being fluidly connected to one of a multiplicity of sample reservoirs, thereby permitting parallel processing and mixing of the samples with a common reagent. This reduces the need for automated reagent distribution mechanisms, reduces the amount of time required for reagent dispensing (that can be performed in parallel with distribution of reagent to a multiplicity of reaction chambers), and permits delivery of small (nL-to-$\mu$L) volumes without using externally-applied electromotive means.

The assembly of a multiplicity of collection chambers on the platforms of the invention also permits simplified detectors to be used, whereby each individual collection/detection chamber can be scanned using mechanisms well-developed in the art for use with, for example, CD-ROM technology. Finally, the platforms of the invention are advantageously provided with sample and reagent entry ports for filling with samples and reagents, respectively, that can be adapted to liquid delivery means known in the art (such as micropipettors).

The discs of this invention have several advantages over those that exist in the centrifugal analyzer art. Foremost is the fact that flow is laminar due to the small dimensions of the fluid channels; this allows for better control of processes such as mixing and washing. Secondly, the small dimensions conferred by microfabrication enable the use of "passive" valuing, dependent upon capillary forces, over much wider range of rotational velocities and with greater reliability than in more macroscopic systems. To this are added the already described advantages of miniaturization.

The present invention solves problems in the current art through the use of a microfluidic disc in which centripetal acceleration is used to move fluids. It is an advantage of the microfluidics platforms of the present invention that the fluid-containing components are constructed to contain a small volume, thus reducing reagent costs, reaction times and the amount of biological material required to perform an assay. It is also an advantage that the fluid-containing components are sealed, thus eliminating experimental error due to differential evaporation of different fluids and the resulting changes in reagent concentration. Because the microfluidic devices of the invention are completely enclosed, both evaporation and optical distortion are reduced to negligible levels. The platforms of the invention also advantageously permit "passive" mixing and valving, i.e., mixing and valving are performed as a consequence of the structural arrangements of the components on the platforms (such as shape, length, position on the platform surface relative to the axis of rotation, and surface properties of the interior surfaces of the components, such as wettability as discussed below), and the dynamics of platform rotation (speed, acceleration, direction and change-of-direction), and permit control of assay timing and reagent delivery.

The devices of the invention also implement simpler, more robust, and more economical sample preparation for performing in vitro amplification reactions such as PCR. All mechanical aspects of sample processing are carried out using a single motor that rotates the disc at prescribed velocities, thereby driving fluids on the disc through microchannels and other microfluidics structures. This is in advantageous over current sample preparation methods involving robotic pipetting stations or other fluid transfer mechanisms, automation for the delivery of processing plates to different "stations," or both.

The invention advantageously integrates sample preparation with thermal cycling for PCR, thereby eliminating additional fluid transfer steps. This minimizes the potential for contamination or fluid loss.

The platforms of the invention reduce the demands on automation in at least three ways. First, the need for precise metering of delivered fluids is relaxed through the use of on-disc metering structures, as described more fully in co-owned U.S. Pat. No. 6,063,589, issued May 16, 2000, and co-owned and co-pending patent applications U.S. Ser. Nos. 08/761,063, filed Dec. 5, 1996; 08/768,990, filed Dec. 18, 1996; 08/910,726, filed Aug. 12, 1997; 08/995,056, filed Dec. 19, 1997; 09/315,114, filed May 19, 1999; 09/579,492, filed May 12, 2000 and 09/595,239, filed Jun. 16, 2000 (Attorney Docket No. 95,1408-XX), the disclosures of each of which are explicitly incorporated by reference herein. By loading imprecise volumes, slightly in excess of those needed for the assay, and allowing the rotation of the disc and use of appropriate microfluidic structures to meter the fluids, much simpler (and less expensive) fluid delivery technology may be employed than is the conventionally required for high-density microtitre plate assays.

Second, the total number of fluid "delivery" events on the microfluidic platform is reduced relative to microtiter plates. By using microfluidic structures that sub-divide and aliquot common reagents (such as reagent solutions, buffers, and enzyme substrates) used in all assays performed on the platform, the number of manual or automated pipetting steps are reduced by at least half (depending on the complexity of the assay). A reduction in fluid transfers to the device can reduce total assay time. Examples of these structures have been disclosed in co-owned U.S. Pat. No. 6,063,589, issued May 16, 2000, and incorporated by reference herein.

The invention also provides on-platform means for mixing reagents with sample and washing the resulting reaction products, removing the need for transferring the assay collection chamber(s) to a separate "wash" station. This also reduces manipulation of the assay device as well as providing controlled and integrated fluid processing.

The invention disclosed herein is flexible as to sample and source, being capable of isolating nucleic acid from bacteria, whole animal blood, tissues and cellular sources. It is rapid, being about 50% more rapid than existing "automated" nucleic acid preparatory methods. The nucleic acid output of the system is of a quality higher than or equal to methods known in the art. The system is simple and easy to use, robust because it is not dependent on operator variability. In addition, the platforms and systems disclosed are self-contained and integrated, thereby minimizing both operator handling and error.

Certain preferred embodiments of the apparatus of the invention are described in greater detail in the following sections of this application and in the drawings.

DETAILED DESCRIPTION OF PREFERRED EMBODIMENTS

Figure 1:
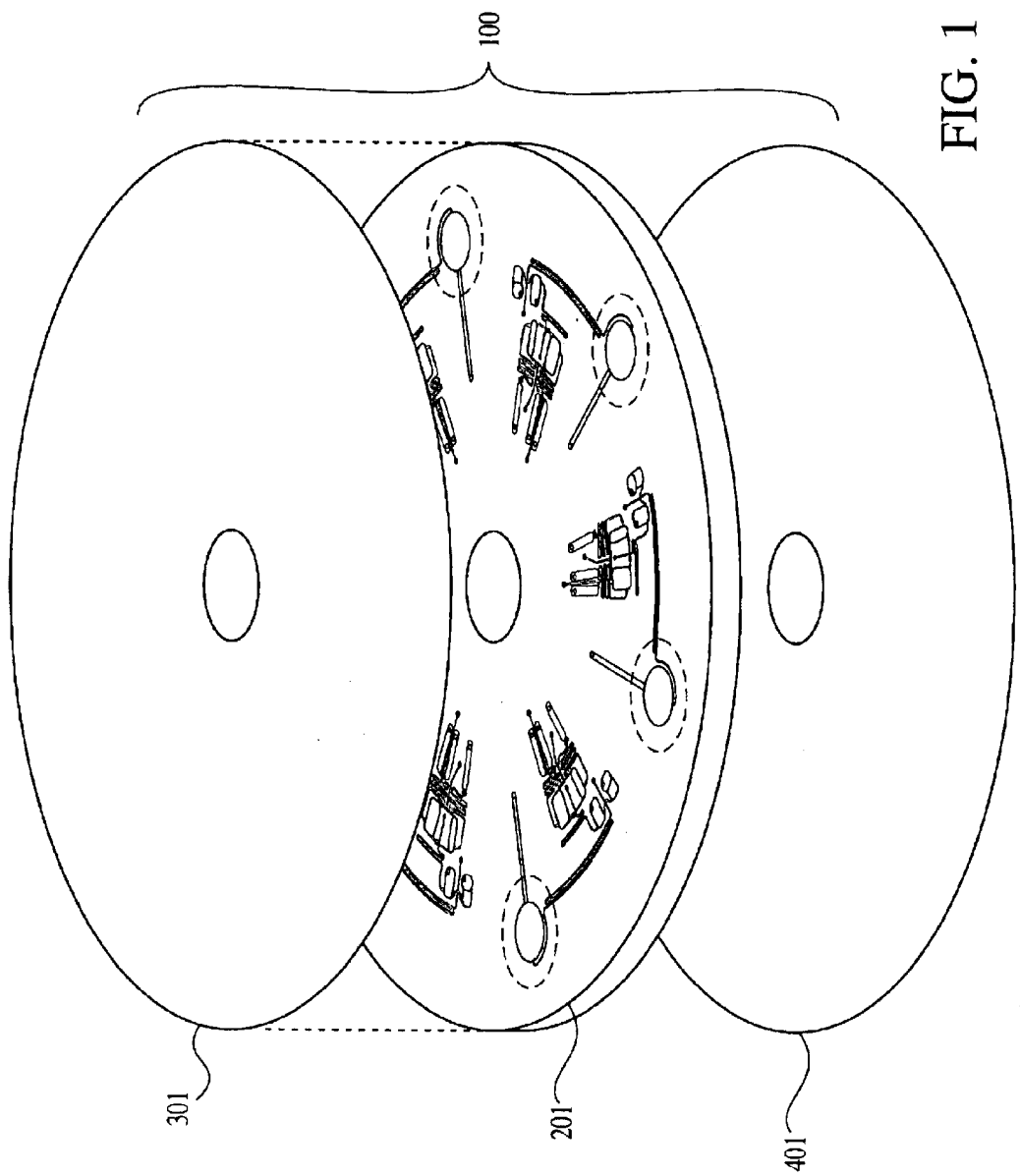
FIG. 1 depicts an exploded, oblique view of a microsystems platform of the invention.

This invention provides a microplatform and a micromanipulation device as disclosed in co-owned U.S. Pat. No. 6,063,589, issued May 16, 2000, and co-owned and co-pending patent applications U.S. Ser. Nos. 08/761,063, filed Dec. 5, 1996; 08/768,990, filed Dec. 18, 1996; 08/910, 726, filed Aug. 12, 1997; 08/995,056, filed Dec. 19, 1997; 09/315,114, filed May 19, 1999; 09/579,492, filed May 12, 2000 and 09/595,239, filed Jun. 16, 2000 (Attorney Docket No. 95,1408-XX), the disclosures of each of which are explicitly incorporated by reference herein, adapted for performing microanalytical and microsynthetic assays of biological samples.

For the purposes of this invention, the term "sample" will be understood to encompass any fluid, solution or mixture, either isolated or detected as a constituent of a more complex mixture, or synthesized from precursor species. In particular, the term "sample" will be understood to encompass any biological species of interest. The term "biological sample" or "biological fluid sample" will be understood to mean any biologically-derived sample, including but not limited to blood, plasma, serum, lymph, saliva, tears, cerebrospinal fluid, urine, sweat, plant and vegetable extracts, semen, and ascites fluid.

For the purposes of this invention, the term "a centripetally motivated fluid micromanipulation apparatus" is intended to include analytical centrifuges and rotors, microscale centrifugal separation apparatuses, and most particularly the Microsystems platforms and disk handling apparatuses as described in co-owned U.S. Pat. No. 6,063,589, issued May 16, 2000, and co-owned and co-pending patent applications U.S. Ser. Nos. 08/761,063, filed Dec. 5, 1996; 08/768,990, filed Dec. 18, 1996; 08/910,726, filed Aug. 12, 1997; 08/995,056, filed Dec. 19, 1997; 09/315,114, filed May 19, 1999; 09/579,492, filed May 12, 2000 and 09/595, 139, filed Jun. 16, 2000 (Attorney Docket No. 95,1408-XX), the disclosures of each of which are explicitly incorporated by reference herein.

For the purposes of this invention, the term "Microsystems platform" is intended to include centripetally-motivated microfluidics arrays as described in co-owned U.S. Pat. No. 6,063,589, issued May 16, 2000, and co-owned and co-pending patent applications U.S. Ser. Nos. 08/761,063, filed Dec. 5, 1996; 08/768,990, filed Dec. 18, 1996; 08/910,726, filed Aug. 12, 1997; 08/995,056, filed Dec. 19, 1997; 09/315,114, filed May 19, 1999; 09/579,492, filed May 12, 2000 and 09/595,239, filed Jun. 16, 2000 (Attorney Docket No. 95,1408-XX), the disclosures of each of which are explicitly incorporated by reference herein.

For the purposes of this invention, the terms "capillary", "microcapillary" and "microchannel" will be understood to be interchangeable and to be constructed of either wetting or non-wetting materials where appropriate.

For the purposes of this invention, the term "reagent reservoir," "assay chamber," "fluid holding chamber," "collection chamber" and "detection chamber" will be understood to mean a defined volume on a microsystems platform of the invention comprising a fluid. The volumetric capacity of these structures as provided herein is from about 2 nL to about 100 μL.

For the purposes of this invention, the terms "entry port" and "fluid input port" will be understood to mean an opening on a Microsystems platform of the invention comprising a means for applying a fluid to the platform.

For the purposes of this invention, the terms "exit port" and "fluid outlet port" will be understood to mean a defined volume on a microsystems platform of the invention comprising a means for removing a fluid from the platform.

For the purposes of this invention, the term "capillary junction" will be understood to mean a region in a capillary or other flow path where surface or capillary forces are exploited to retard or promote fluid flow. A capillary junction is provided as a pocket, depression or chamber in a hydrophilic substrate that has a greater depth (vertically within the platform layer) and/or a greater width (horizontally within the platform layer) that the fluidics component (such as a microchannel) to which it is fluidly connected. For liquids having a contact angle less than 90° (such as aqueous solutions on platforms made with most plastics, glass and silica), flow is impeded as the channel cross-section increases at the interface of the capillary junction. The force hindering flow is produced by capillary pressure, that is inversely proportional to the cross sectional dimensions of the channel and directly proportional to the surface tension of the liquid, multiplied by the cosine of the contact angle of the fluid in contact with the material comprising the channel. The factors relating to capillarity in microchannels according to this invention have been discussed in co-owned U.S. Pat. No. 6,063,589, issued May 12, 2000 and in co-owned and co-pending U.S. patent application, Ser. No. 08/910, 726, filed Aug. 12, 1997, incorporated by reference in its entirety herein.

Capillary junctions can be constructed in at least three ways. In one embodiment, a capillary junction is formed at the junction of two components wherein one or both of the lateral dimensions of one component is larger than the lateral dimension(s) of the other component. As an example, in microfluidics components made from "wetting" or "wettable" materials, such a junction occurs at an enlargement of a capillary as described in co-owned and co-pending U.S. Ser. Nos. U.S. Ser. Nos. 08/761,063, filed Dec. 5, 1996; 08/768,990, filed Dec. 18, 1996; and 08/910,726, filed Aug. 12, 1997. Fluid flow through capillaries is inhibited at such junctions. At junctions of components made from non-wetting or non-wettable materials, on the other hand, a constriction in the fluid path, such as the exit from a chamber or reservoir into a capillary, produces a capillary junction that inhibits flow. In general, it will be understood that capillary junctions are formed when the dimensions of the components change from a small diameter (such as a capillary) to a larger diameter (such as a chamber) in wetting systems, in contrast to non-wettable systems, where capillary junctions form when the dimensions of the components change from a larger diameter (such as a chamber) to a small diameter (such as a capillary).

A second embodiment of a capillary junction is formed using a component having differential surface treatment of a capillary or flow-path. For example, a channel that is hydrophilic (that is, wettable) may be treated to have discrete regions of hydrophobicity (that is, non-wettable). A fluid flowing through such a channel will do so through the hydrophilic areas, while flow will be impeded as the fluid-vapor meniscus impinges upon the hydrophobic zone.

The third embodiment of a capillary junction according to the invention is provided for components having changes in both lateral dimension and surface properties. An example of such a junction is a microchannel opening into a hydrophobic component (microchannel or reservoir) having a larger lateral dimension. Those of ordinary skill will appreciate how capillary junctions according to the invention can be created at the juncture of components having different sizes in their lateral dimensions, different hydrophilic properties, or both.

For the purposes of this invention, the term "capillary action" will be understood to mean fluid flow in the absence of rotational motion or centripetal force applied to a fluid on a rotor or platform of the invention and is due to a partially or completely wettable surface.

For the purposes of this invention, the term "capillary microvalve" will be understood to mean a capillary microchannel comprising a capillary junction whereby fluid flow is impeded and can be motivated by the application of pressure on a fluid, typically by centripetal force created by rotation of the rotor or platform of the invention. Capillary microvalves will be understood to comprise capillary junctions that can be overcome by increasing the hydrodynamic pressure on the fluid at the junction, most preferably by increasing the rotational speed of the platform.

For the purposes of this invention, the term "sacrificial valve" will be understood to mean a valve preferably made of a fungible material that can be removed from the fluid flow path. In preferred embodiments, said sacrificial valves are wax valves and are removed from the fluid flow path by heating, using any of a variety of heating means including infrared illumination and most preferably by activation of heating elements on or embedded in the platform surface as described in co-owned U.S. Pat. No. 6,063,589, incorporated by reference.

For the purposes of this invention, the term "in fluid communication" or "fluidly connected" is intended to define components that are operably interconnected to allow fluid flow between components. In preferred embodiments, the platform comprises a rotatable platform, more preferably a disk, whereby fluid movement on the disk is motivated by centripetal force upon rotation of the disk.

For the purposes of this invention, the term "air displacement channels" will be understood to include ports in the surface of the platform that are contiguous with the components (such as microchannels, chambers and reservoirs) on the platform, and that comprise vents and microchannels that permit displacement of air from components of the platforms and rotors by fluid movement.

The microplatforms of the invention (preferably and hereinafter collectively referred to as "disks"; for the purposes of this invention, the terms "microplatform", "Microsystems platform" and "disk" are considered to be interchangeable) are provided to comprise one or a multiplicity of microsynthetic or microanalytic systems (termed "microfluidics structures" herein). Such microfluidics structures in turn comprise combinations of related components as described in further detail herein that are operably interconnected to allow fluid flow between components upon rotation of the disk. These components can be microfabricated as described below either integral to the disk or as modules attached to, placed upon, in contact with or embedded in the disk. For the purposes of this invention, the term "microfabricated" refers to processes that allow production of these structures on the sub-millimeter scale. These processes include but are not restricted to molding, photolithography, etching, stamping and other means that are familiar to those skilled in the art.

The invention also comprises a micromanipulation device for manipulating the disks of the invention, wherein the disk is rotated within the device to provide centripetal force to effect fluid flow on the disk. Accordingly, the device provides means for rotating the disk at a controlled rotational velocity, for stopping and starting disk rotation, and advantageously for changing the direction of rotation of the disk. Both electromechanical means and control means, as further described herein, are provided as components of the devices of the invention. User interface means (such as a keypad and a display) are also provided, as further described in co-owned U.S. Pat. No. 6,063,589, issued May 16, 2000, and co-owned and co-pending patent applications U.S. Ser. Nos. 08/761,063, filed Dec. 5, 1996; 08/768,990, filed Dec. 18, 1996; 08/910,726, filed Aug. 12, 1997; 08/995,056, filed Dec. 19, 1997; 09/315,114, filed May 19, 1999; 09/579,492, filed May 12, 2000 and 09/595,239, filed Jun. 16, 2000 (Attorney Docket No. 95,1408-XX), the disclosures of each of which are explicitly incorporated by reference herein.

Temperature control elements are provided to control the temperature of the platform during incubation of a fluid thereupon. The invention therefore provides heating elements, including heat lamps, direct laser heaters, Peltier heat pumps, resistive heaters, ultrasonication heaters and microwave excitation heaters, and cooling elements, including Peltier devices and heat sinks, radiative heat fins and other components to facilitate radiative heat loss. Thermal devices are preferably arrayed to control the temperature of the platform over a specific area or multiplicity of areas. Preferably, heating and cooling elements comprise the platforms of the invention comprising a thermal regulation layer in the platform surface that is in thermal contact with the microfluidics components, most preferably microchannels as described herein. The temperature of any particular area on the platform (preferably, the microchannels at any particular thermally regulated area) is monitored by resistive temperature devices (RTD), thermistors, liquid crystal birefringence sensors or by infrared interrogation using IR-specific detectors, and can be regulated by feedback control systems. Temperature control on the microsystems platforms of this invention is most preferably achieved using the methods and devices disclosed in co-owned U.S. Pat. No. 6,063,589, incorporated by reference herein.

In preferred embodiments, portions of the microsystems platform surface are adapted for providing regions of controlled temperature (termed "thermal regions" or "thermal arrays" herein) using integral heating elements as disclosed in U.S. Pat. No. 6,063,589, incorporated by reference. In more preferred embodiments, the portions of the microsystems platform surface are constituted in arrays of thermal control elements, most preferably wherein is produced adjacent regions of the platform surface having different temperatures. In preferred embodiments, the platform also comprises other components as disclosed in co-owned and co-pending patent applications U.S. Ser. Nos. 08/761,063, filed Dec. 5, 1996; 08/768,990, filed Dec. 18, 1996; 08/910, 726, filed Aug. 12, 1997; 08/995,056, filed Dec. 19, 1997; 09/315,114, filed May 19, 1999; 09/579,492, filed May 12, 2000 and 09/595,239, filed Jun. 16, 2000 (Attorney Docket No. 95,1408-XX), the disclosures of each of which are explicitly incorporated by reference herein, most preferably channels and microchannels, whereby fluid flow traverses each of the different regions having different temperatures at least once, or more preferably, several times. In these embodiments, the amount of time fluid is within any particular thermal region, and thus at any particular temperature is dependent on the path length of the channel in the region, the square of the hydraulic diameter of the channel, and the square of the rotational speed of the platform. In preferred embodiments the arrays comprise at least 2 or 3 regions of different temperature adjacent to one another. In certain embodiments, the thermal regions are rectangular in shape, while in other embodiments the thermal regions are wedge-shaped, having a broader annular diameter at positions distal to the axis of rotation than at positions proximal to the axis of rotation.

In preferred embodiments of the platforms of the invention, the thermal arrays and regions of elevated temperatures constructed in the surface of the platforms of the invention comprise a thermal heating element. In preferred embodiments, the thermal heating element is a resistive heater element or a thermofoil heater, which is an etched-foil heating element enclosed in an electrically insulating plastic (Kapton, obtained from Minco). Resistive heater elements comprising the platforms of the invention are as described in co-owned U.S. Pat. No. 6,063,587. Briefly, said resistive heater elements comprise in combination an electrically inert substrate capable of being screen printed with a conductive ink and a resistive ink; a conductive ink screen-printed in a pattern; and a resistive ink screen-printed in a pattern over the conductive ink pattern wherein the resistive ink in electrical contact with the conductive ink and wherein an electrical potential applied across the conductive ink causes current to flow across the resistive ink wherein the resistive ink produces heat. Such structures are defined as "electrically-resistive patches" herein. Preferably, the conductive ink is a silver conductive ink such as Dupont 5028, Dupont 5025, Acheson 423SS, Acheson 426SS and Acheson SS24890, and the resistive ink is, for example, Dupont 7082, Dupont 7102, Dupont 7271, Dupont 7278 or Dupont 7285, or a PTC (positive temperature coefficient) ink. In alternative embodiments, the resistive heater element can further comprise a dielectric ink screen-printed over the resistive ink pattern and conductive ink pattern.

The invention provides a combination of specifically adapted microplatforms that are rotatable, analytic/synthetic microvolume assay platforms, and a micromanipulation device for manipulating the platform to achieve fluid movement on the platform arising from centripetal force on the platform as result of rotation. The platform of the invention is preferably and advantageously a circular disk; however, any platform capable of being rotated to impart centripetal for a fluid on the platform is intended to fall within the scope of the invention. The micromanipulation devices of the invention are more fully described in co-owned and co-pending U.S. Ser. Nos. U.S. Ser. Nos. 08/761,063, filed Dec. 5, 1996; 08/768,990, filed Dec. 18, 1996, now U.S. Pat. No. 6,319,469; 08/910,726, filed Aug. 12, 1997, now U.S. Pat. No. 6,143,248; 08/995,056, filed Dec. 19, 1997, now U.S. Pat. No. 6,143,247; 09/315,114, filed May 19, 1999; 09/579,492, filed May 12, 2000 and 09/515,239 filed Jun. 16, 2000 (Attorney Docket No. 95,1408-XX), now U.S. Pat. No. 6,582,662 the disclosures of each of which are explicitly incorporated by reference herein.

Fluid (including reagents, samples and other liquid components) movement is controlled by centripetal acceleration due to rotation of the platform. The magnitude of centripetal acceleration required for fluid to flow at a rate and under a pressure appropriate for a particular microfluidics structure on the microsystems platform is determined by factors including but not limited to the effective radius of the platform, the interior diameter of microchannels, the position angle of the microchannels on the platform with respect to the direction of rotation, and the speed of rotation of the platform. In certain embodiments of the methods of the invention an unmetered amount of a fluid (either a sample or reagent solution) is applied to the platform and a metered amount is transferred from a fluid reservoir to a microchannel, as described in co-owned U.S. Pat. No. 6,063,589, issued May 16, 2000, and co-owned and co-pending patent applications U.S. Ser. Nos. 08/761,063, filed Dec. 5, 1996; 08/768,990, filed Dec. 18, 1996; 08/910, 726, filed Aug. 12, 1997; 08/995,056, filed Dec. 19, 1997; 09/315,114, filed May 19, 1999; 09/579,492, filed May 12, 2000 and 09/595,239, filed Jun. 16, 2000 (Attorney Docket No. 95,1408-XX), the disclosures of each of which are explicitly incorporated by reference herein. In preferred embodiments, the metered amount of the fluid sample provided on an inventive platform is from about 1 nL to about 500 $\mu$L. In these embodiments, metering manifolds comprising one or a multiplicity of metering capillaries are provided to distribute the fluid to a plurality of components of the microfluidics structure.

The components of the platforms of the invention are in fluidic contract with one another. In preferred embodiments, fluidic contact is provided by microchannels comprising the surface of the platforms of the invention. Microchannel sizes are optimally determined by specific applications and by the amount of and delivery rates of fluids required for each particular embodiment of the platforms and methods of the invention. Microchannel sizes can range from 0.1 $\mu$m to a value close to the thickness of the disk (e.g., about 1 mm); in preferred embodiments, the interior dimension of the microchannel is from 0.5 $\mu$m to about 500 $\mu$m. Microchannel and reservoir shapes can be trapezoid, circular or other geometric shapes as required. Microchannels preferably are embedded in a microsystem platform having a thickness of about 0.1 to 25 mm, wherein the cross-sectional dimension of the microchannels across the thickness dimension of the platform is less than 1 mm, and can be from 1 to 90 percent of said cross-sectional dimension of the platform. Sample reservoirs, reagent reservoirs, reaction chambers, collection chambers, detections chambers and sample inlet and outlet ports preferably are embedded in a microsystem platform having a thickness of about 0.1 to 25 mm, wherein the cross-sectional dimension of the microchannels across the thickness dimension of the platform is from 1 to 75 percent of said cross-sectional dimension of the platform. In preferred embodiments, delivery of fluids through such channels is achieved by the coincident rotation of the platform for a time and at a rotational velocity sufficient to motivate fluid movement between the desired components.

Input and output (entry and exit) ports are components of the microplatforms of the invention that are used for the introduction or removal of fluid components. Entry ports are provided to allow samples and reagents to be placed on or injected onto the disk; these types of ports are generally located towards the center of the disk. Exit ports are also provided to allow products to be removed from the disk. Port shape and design vary according specific applications. For example, sample input ports are designed, inter alia, to allow capillary action to efficiently draw the sample into the disk. In addition, ports can be configured to enable automated sample/reagent loading or product removal. Entry and exit ports are most advantageously provided in arrays, whereby multiple samples are applied to the disk or to effect product removal from the microplatform.

In some embodiments of the platforms of the invention, the inlet and outlet ports are adapted to the use of manual pipettors and other means of delivering fluids to the reservoirs of the platform. In alternative, advantageous embodiments, the platform is adapted to the use of automated fluid loading devices. One example of such an automated device is a single pipette head located on a robotic arm that moves in a direction radially along the surface of the platform. In this embodiment, the platform could be indexed upon the spindle of the rotary motor in the azimuthal direction beneath the pipette head, which would travel in the radial direction to address the appropriate reservoir.

Also included in air handling systems on the disk are air displacement channels, whereby the movement of fluids displaces air through channels that connect to the fluid-containing microchannels retrograde to the direction of movement of the fluid, thereby providing a positive pressure to further motivate movement of the fluid.

Platforms of the invention such as disks and the microfluidics components comprising such platforms are advantageously provided having a variety of composition and surface coatings appropriate for particular applications. Platform composition will be a function of structural requirements, manufacturing processes, and reagent compatibility/chemical resistance properties. Specifically, platforms are provided that are made from inorganic crystalline or amorphous materials, e.g. silicon, silica, quartz, inert metals, or from organic materials such as plastics, for example, poly(methyl methacrylate) (PMMA), acetonitrile-butadiene-styrene (ABS), polycarbonate, polyethylene, polystyrene, polyolefins, polypropylene and metallocene. These may be used with unmodified or modified surfaces as described below. The platforms may also be made from thermoset materials such as polyurethane and poly(dimethyl siloxane) (PDMS). Also provided by the invention are platforms made of composites or combinations of these materials; for example, platforms manufactures of a plastic material having embedded therein an optically transparent glass surface comprising the detection chamber of the platform. Alternately, platforms composed of layers made from different materials may be made. The surface properties of these materials may be modified for specific applications, as disclosed in co-owned U.S. Pat. No. 6,063,589, issued May 16, 2000, and co-owned and co-pending patent applications U.S. Ser. Nos. 08/761,063, filed Dec. 5, 1996; 08/768,990, filed Dec. 18, 1996; 08/910,726, filed Aug. 12, 1997; 08/995,056, filed Dec. 19, 1997; 09/315,114, filed May 19, 1999; 09/579,492, filed May 12, 2000 and 09/595,239, filed Jun. 16, 2000 (Attorney Docket No. 95,1408-XX), the disclosures of each of which are explicitly incorporated by reference herein.

Preferably, the disk incorporates microfabricated mechanical, optical, and fluidic control components on platforms made from, for example, plastic, silica, quartz, metal or ceramic. These structures are constructed on a sub-millimeter scale by molding, photolithography, etching, stamping or other appropriate means, as described in more detail below. It will also be recognized that platforms comprising a multiplicity of the microfluidics structures are also encompassed by the invention, wherein individual combinations of microfluidics and reservoirs, or such reservoirs shared in common, are provided fluidly connected thereto. An example of such a platform is shown in FIG. 1.

Platform Manufacture and Assembly

Microfluidics structures are provided embedded in a substrate comprising the Microsystems platform of the invention. The platform is preferably manufactured and assembled as layers containing separate components that are bonded together. As illustrated in FIG. 1, the exemplified embodiment of the platforms of the invention comprise two layers, a reservoir layer and a microfluidics layer. Platforms having additional layers are also within the scope of the invention.

The reservoir layer of the platform is manufactured from a thermoplastic material such as acrylic, polystyrene, polycarbonate, or polyethylene. For such materials, fabrication methods include machining and conventional injection molding. For injection molding, the mold inserts that are used to define the features of the platform can be created using standard methods of machining, electrical discharge machining, and other means known in the art.

The reservoir layer of the platform can also be manufactured from a thermoset material or other material that exists in a liquid form until subjected to heat, radiation, or other energy sources. Examples of thermoset materials include poly(dimethyl siloxane) (PDMS), polyurethane, or epoxy. Typically, these materials are obtained from the manufacturer in two parts; the two parts are mixed together in a prescribed ratio, injected into or poured over a mold and subjected to heat to initiate and complete cross-linking of the monomers present in the pre-polymer fluid. The process of rapidly injecting a pre-polymer fluid into a mold and then cross-linking or curing the part is often referred to as reaction injection molding (RIM). The process of pouring a pre-polymer fluid over a mold and then allowing the part to cross-link or cure is often referred to as casting. Mold inserts for RIM or casting can be fabricated using standard methods of machining, electrical discharge machining, and other means known in the art.

The microfluidics layer of the platform can also be manufactured from a thermoplastic material such as acrylic, polystyrene, polycarbonate, or polyethylene. Because the dimensions of the channels and cuvettes may be much smaller than those found in the reservoir layer, typical fabrication methods with these materials may include not only machining and conventional injection molding but also compression/injection molding, and embossing or coining. For injection molding, the mold inserts that are used to define the features of this layer of the platform can be created using conventional methods such as machining or electrical discharge machining. For mold inserts with features too fine to be created in conventional ways, various microfabrication techniques are used. These include silicon micromachining, in which patterns are created on a silicon wafer substrate through the use of a photoresist and a photomask (Madou, 1997, *Fundamentals of Microfabrication*, CRC Press: Boca Raton, Fla.). When the silicon wafer is subjected to an etching agent, the photoresist prevents penetration of the agent into the silicon beneath the photoresist, while allowing etching to occur in the exposed areas of the silicon. In this way patterns are etched into the silicon and can be used to create microfabricated plastic parts directly through embossing. In this process, the etched silicon is brought into contact with a flat thermoplastic sheet under high pressure and at a temperature near the glass transition temperature of the plastic. As a result, the pattern is transferred in negative into the plastic.

Etched silicon may also be used to create a metal mold insert through electroplating using, for example, metallic nickel. Silicon etched using any one of a variety of techniques such as anisotropoic or isotropic wet etching or deep reactive ion etching (DRIE) may serve as a basis for a metal mold. A seed layer of nickel is deposited through evaporation on the silicon; once such an electrically-conductie seed layer is formed, conventional electroplating techniques may be used to build a thick nickel layer. Typically, the silicon is then removed (Larsson, 1997, *Micro Structure Bull.* 1: 3).

The insert is then used in conventional injection molding or compression/injection molding.

In addition to silicon micromachining for mold inserts, molds can alternatively be created using photolithography without etching the silicon. Photoresist patterns are created on silicon or other appropriate substrates. Rather than etching the silicon wafer as in silicon micromachining, the photoresist pattern and silicon are metallized through electroplating, thermal vapor deposition, or other means known in the art. The metal relief pattern then serves as a mold for coining, injection molding, or compression/injection molding as described above.

The microfluidic layer of the platform can also be manufactured using a thermoset material as described above for production of the reservoir layer, wherein the mold pattern for thermosets of the microfluidics layer is prepared as described above. Because reaction-injection molding and casting do not require the high pressures and temperatures of injection molding, a wider variety of mold patterns may be used. In addition to the use of a silicon or metal mold insert, the photoresist pattern as described can also be used as a mold relief itself. While the photoresist would not withstand the high pressures and temperatures of injection molding, the milder conditions of casting or RIM create no significant damage.

The assembly of the platform involves registration and attachment of the microfluidic layer to the reservoir layer. In order for the microfluidics structures on the platform to be useful for performing assays as described herein, certain microfluidics pathways in the reservoir layer must be connected to certain microfluidics pathways in the microfluidics layer. Registration of these microfluidics pathways may be accomplished through optical alignment of fiducial marks on the microfluidic and reservoir layers or through mechanical alignment of holes or depressions on the microfluidic layer with pins or raised features on the reservoir layer. The required registration tolerances may be relaxed by designing the microfluidics pathway in the reservoir layer to be much larger than the microfluidics pathway in the microfluidics layer, or vice versa.

Attachment may be accomplished in a number of ways, including conformal sealing, heat sealing or fusion bonding, bonding with a double-sided adhesive tape or heat-sealable film, bonding with a ultraviolet (UV) curable adhesive or a heat-curable glue, chemical bonding or bonding with a solvent.

A requirement for conformal sealing is that one or both of the layers are made of an elastomeric material and that the surfaces to be bonded are free of dust or debris that could limit the physical contact of the two layers. In a preferred assembly approach, an elastomeric microfluidics layer is registered with respect to and then pressed onto a rigid reservoir layer. The elastomeric microfluidics layer may be advantageously made of silicone and the rigid reservoir layer may be advantageously made of acrylic or polycarbonate. Hand pressure allows the layers to adhere through vander Waals forces.

A requirement for heat sealing or fusion bonding is that both the reservoir and microfluidics layers are made of thermoplastic materials and that the sealing occurs at temperatures above the glass transition temperatures, in the case of amorphous polymers, or melting temperatures, in the case of semi-crystalline polymers, of both of the layer materials. In a preferred assembly approach, the microfluidics layer is registered with respect to and pressed onto the reservoir layer, this composite disk is then placed between two flat heated blocks and pressure is applied to the composite through the heated blocks. By adjusting the temperature versus time profile at each of the faces of the composite disk and by adjusting the pressure versus time profile that is applied to the composite system, one can determine the time-temperature-pressure profile that allows for bonding of the two layers yet minimizes variation of the features within each of the layers. For example, heating two acrylic disks from room temperature to a temperature just above the glass transition temperature of acrylic at a constant pressure of 250 psi over one hour is a recipe that allows for minimal variation of 250 $\mu$m wide fluidic channels. In another assembly approach, the bond surfaces of the microfluidics and reservoir layers are separately heated in a non-contact fashion with radiative lamp and when the bond surfaces have reached their glass transition temperatures the microfluidics layer is registered with respect to and pressed onto the reservoir layer.

A double-sided adhesive tape or heat sealable film may be used to bond the microfluidics and reservoir layers. Before bonding, holes are first cut into the tape (or film) to allow for fluid communication between the two layers, the tape (or film) is registered with respect to and applied onto the reservoir layer, and the microfluidics layer is registered with respect to and applied onto the tape(or film)/reservoir layer composite. In order to bond a heat-sealable film to a surface, it is necessary to raise the temperature of the film to above the glass transition temperature, in the case of an amorphous polymer, or the melting temperature, in the case of a semicrystalline polymer, of the film's adherent polymer material. For bonding with an adhesive tape or a heat-sealable film, an adequate bond can typically be achieved with hand pressure.

A photopolymerizable polymer (for example, a UV-curable glue) or a heat-curable polymer may be used to adhere the microfluidics and reservoir layers. In one approach, this glue is applied to one or both of the layers. Application methods include painting, spraying, dip-coating or spin coating. After the application of the glue the layers are assembled and exposed to ultraviolet radiation or heat to allow for the initiation and completion of cross-linking or setting of the glue. In another approach, the microfluidics and reservoir layers are each fabricated with a set of fluid channels that are to be used only for the glue. These channels may, for example, encircle the fluid channels and cuvettes used for the assay. The microfluidics layer is registered with respect to and pressed onto the reservoir layer. The glue is pipetted into the various designated channels and after the glue has filled these channels, the assembled system is exposed to ultraviolet radiation or heat to allow for the cross-linking or setting of the glue.

When polydimethylsiloxane (PDMS) or silicone is first exposed to an oxygen plasma and then pressed onto a similarly treated silicone surface in an ambient environment, the two surfaces adhere. It is thought that the plasma treatment converts the silicone surface to a silanol surface and that the silanol groups are converted to siloxane bonds when the surfaces are brought together (Duffy et al., 1998, *Anal. Chem.* 70: 4974–4984). This chemical bonding approach is used to adhere the silicone microfluidics and reservoir layer.

A requirement for solvent bonding is that the bond surfaces of both the microfluidics and reservoir layers can be solvated or plasticized with a volatile solvent. For solvent bonding, the bond surfaces are each painted with the appropriate solvating fluid or each exposed to the appropriate solvating vapor and then registered and pressed together.

Plasticization allows the polymer molecules to become more mobile and when the surfaces are brought in contact the polymer molecules become entangled; once the solvent has evaporated the polymer molecules are no longer mobile and the molecules remain entangled, thereby allowing for a physical bond between the two surfaces. In another approach, the microfluidics and reservoir layers are each fabricated with a set of fluid channels that are to be used only for the solvent and the layers are bonding much like they are with the UV-curable or heat-curable glue as described above.

Once assembled, the internal surfaces of the microfluidic manifold may be passivated with a parylene coating. Parylene is a vapor-deposited conformal polymer coating that forms a barrier layer on the internal, fluid-contacting surfaces of a microfluidic device following construction. The coating forms an impermeable layer that prevents any exchange of matter between the fluids and materials used to construct the device. The use of a low temperature, vapor deposition method allows the device to be manufactured and then passivated in its final form. This passivation approach can be used to improve the performance of assays. In particular, when an adhesive is used in the disk construction, there is a potential for contamination of the fluids by the adhesive material (or the plastic substrate or cover). Interfering substances leaching from the adhesive, or adsorption and binding of substances by the adhesive, can interfere with chemical or biochemical reactions. This can be more of a problem at elevated temperatures or if solvents, strong acids or bases are required.

Construction of Electric or Electronic Platen Comprising Temperature Control Elements The invention provides an electric or electronic platen containing temperature control elements positioned on the platen to correspond to microfluidics structures such as thermal cycling chambers and sacrificial valves. The platen and microfluidics structures are aligned using fiducials or other registers for proper positioning the components on each platform layer with each other.

The invention also provides a micromanipulation apparatus for rotating the platen and microfluidics platform, including most preferably a slip ring feature on a rotational spindle or axis that permits electrical contact to be maintained between the device and the rotating platen. Temperature controlling elements are provided in the device to maintain any particular temperature at a specific position on the disc surface using thermistors and heating elements, including resistive heaters and Peltier elements. The device controls rotation of the microfluidics disc and distributes and receives electrical signals to the platen rotating with the microfluidics disc in real time.

Figure 20:
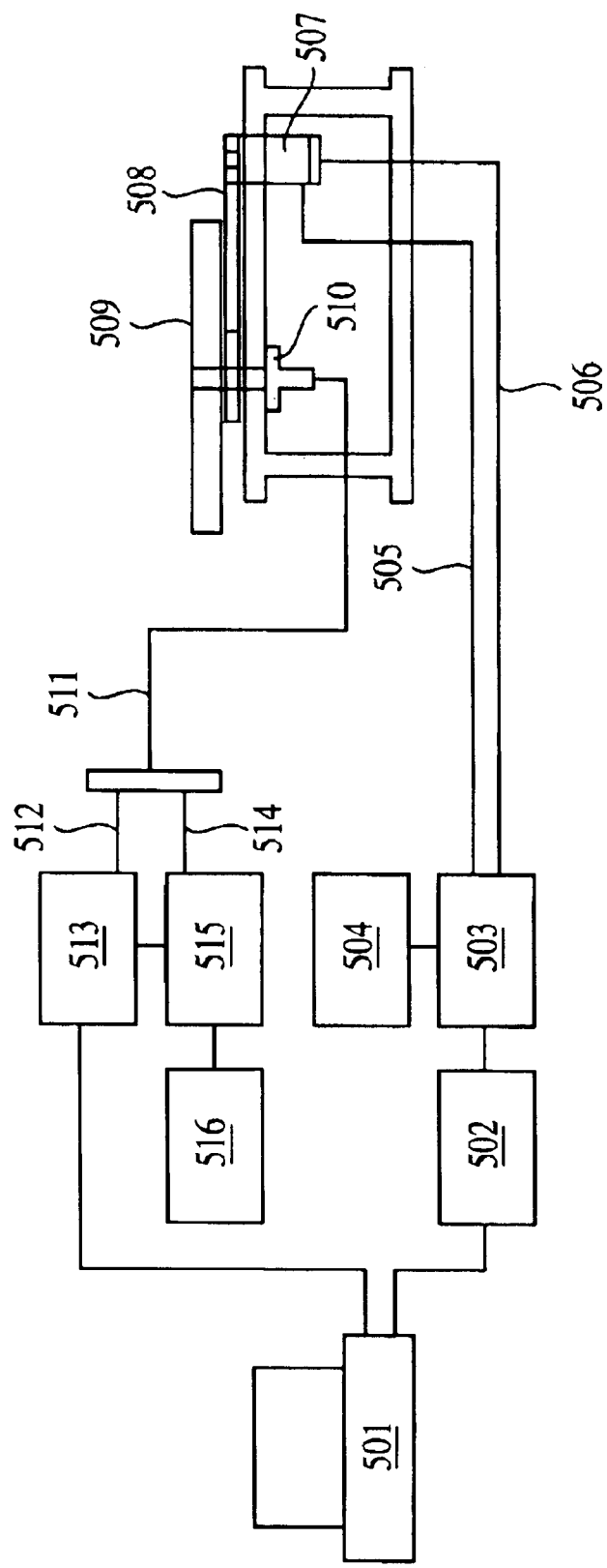
FIG. 20 is a plan view diagram of the electric platen and controlling elements of the invention.

The relationship between the device and platen is illustrated in FIG. 20. With regard to the Figure, platen 509 is inserted on a spindle containing 24-channel slip ring 510, commercially available from Litton, (Part No. AC6023-24). Rotation of the platen about the spindle is controlled by drive motor 507, preferably also comprising an encoder such as one commercially available from Micromo, (Part No. 3557K012CR), via drive belt 508. Drive motor 507 is controlled by the device through drive motor power line 505 and where application encoder signal line 506.

The device is controlled by microprocessor 501, most preferably comprising a computer such as a PC. Platform rotation is controlled by servomotor controller 503, for example as commercially available from J. R. Kerr (Part No. PIC-SERVO). Servo motor 503 is equipped with a power supply 504, commercially available from Skynet Electronic (Part No. ARC-2133). The servo motor is controlled by the PC through an interface, for example, using a serial port converter connected to the COM port of the PC (Part No. Z238-485, J. R. Kerr).

The device is also provided having a control system for controlling electric power to the platen. A multiline cable 511 connects the slip ring to a breakout board 517, which is connected to a proportional integral derivative (PID) circuit connected to a commercially-available AID board in the PC (Computer Boards, Part No. CIO-DAS1600) by temperature sensor line 512. This circuit receives temperature data from thermistors on the platen surface, disclosed more extensively below, and controls current delivery to temperature control elements by programmable current source 515 and power source 516.

Figure 21:
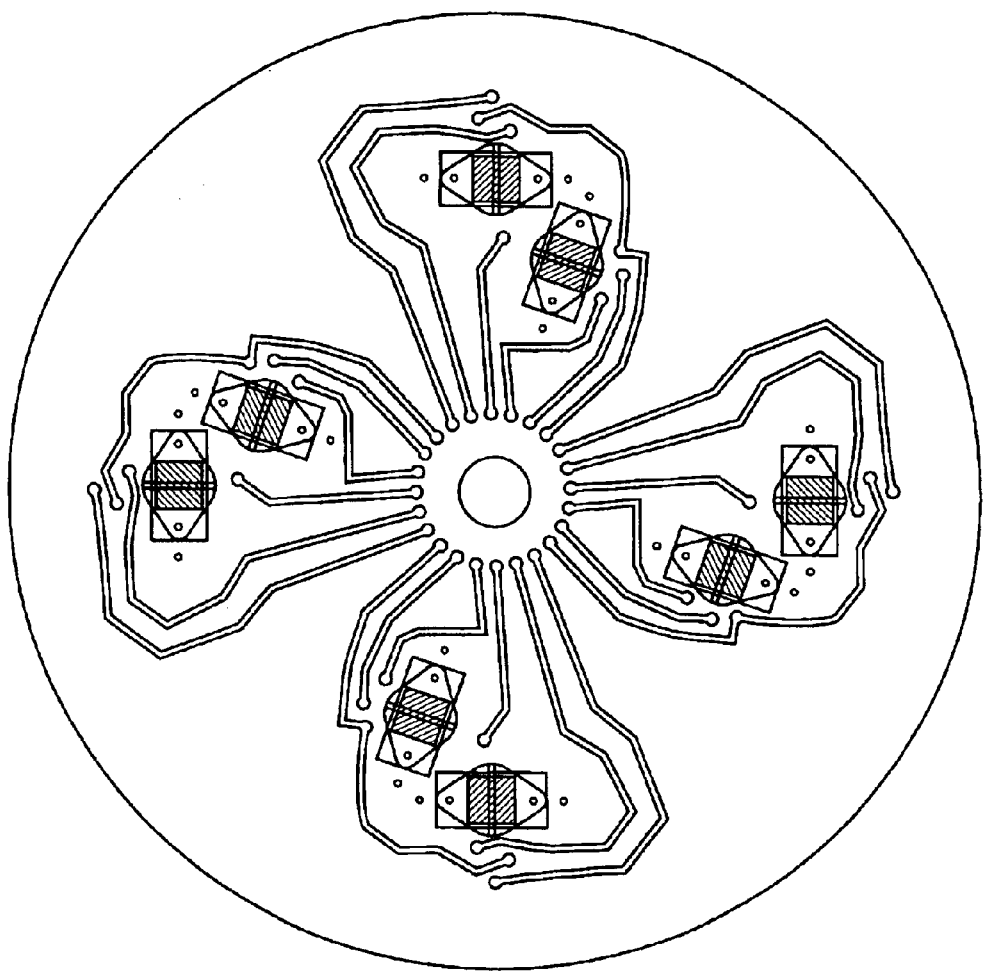
FIG. 21 is a plan view diagram of the temperature control elements on an electric platen of the invention.

The platen itself is shown in plan view in FIG. 21. The platen most preferably is constructed from printed circuit board 551 onto which electronic elements (including electrical leads, thermistors, Peltier elements, brass blocks for providing thermal contact with the microfluidics disc, and radiative fins for heat dissipation have been affixed.

FIG. 21 shows the layout of the temperature control elements on the platen, illustrated in the Figure with Peltier elements 554. The platen has brass thermal contacts 552 and 553 positioned on the platen surface to correspond to microfluidics structure on the microfluidics disc. Brass contact 552 has a groove 555 embedded therein to accommodate a temperature sensing element. Positioned in between the thermal contacts in each combination is Peltier element 554. Also illustrated in the Figure is a second temperature control element, comprising brass thermal contacts 557 and 558, groove 559, and Peltier element 558. The positioning of these elements permits temperature control and heating of multiple components of a particular microfluidics structure (such as control of thermal cycling chambers and lysis chambers, for example).

Figure 22:
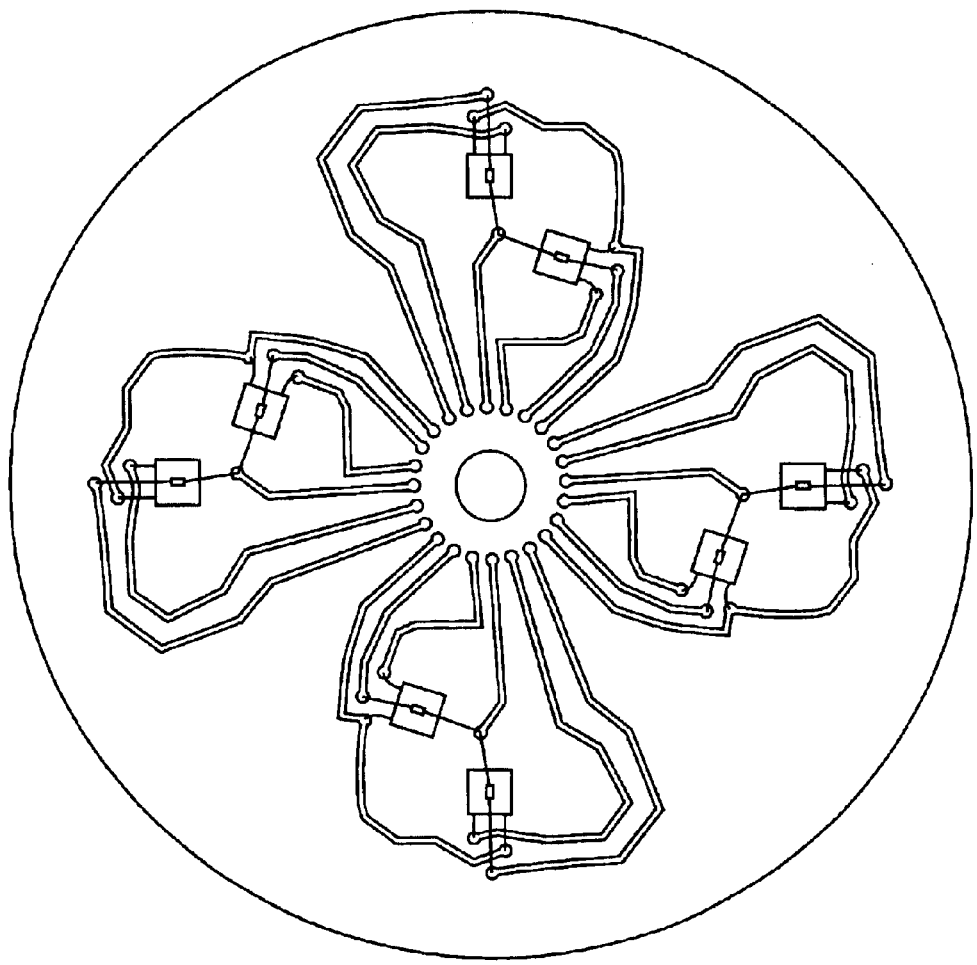
FIG. 22 is a plan view diagram of the electrical contacts between the electrical leads on the printed circuit board of the platen and temperature control elements.

Electric leads controlling the temperature control elements on the platen are more specifically depicted in FIG. 22. Peltier element 554 is controlled by leads 601 and 605 connected through 607 and 608. Thermistor 606 contained in groove 555 is controlled (that is, the temperature information in the form of changes in resistance to current flow in the thermistor upon heating or cooling is transmitted to the temperature control elements in the PC) through leads 600 and 602 connected through 609 and 610. Similarly, Peltier element 558 is controlled by leads 603 and 605 connected through 612 and 613. Thermistor 611 contained in groove 559 is controlled (that is, the temperature information in the form of changes in resistance to current flow in the thermistor upon heating or cooling is transmitted to the temperature control elements in the PC) through leads 602 and 604 connected through 614 and 615. In construction of the electric connections between the elements on the platen and the slip ring, the use of the same lead as a "ground" (see, for example, the communion connection to lead 602 between thermistor 606 and thermistor 611) conserves the number of connections used per element and permits control of up to 8 elements per platen.

Figure 23:
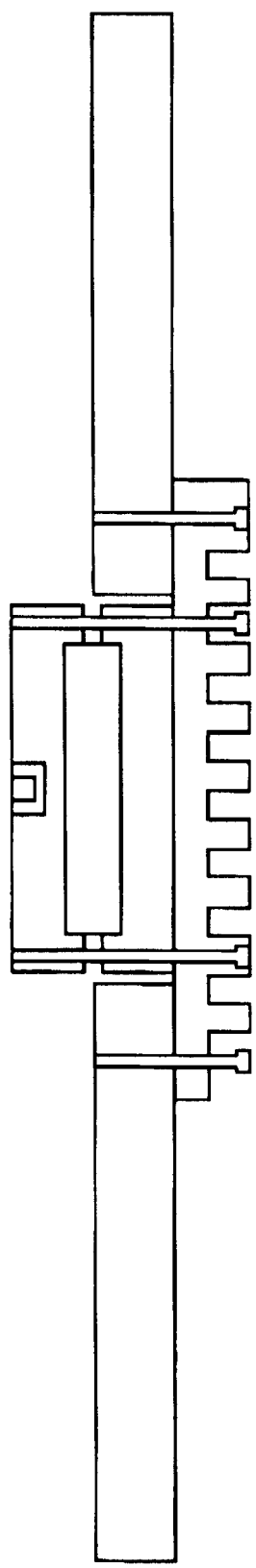
FIG. 23 is a cross-sectional view of the structure of a temperature control element comprising a Peltier element according to the invention.

The structure of the temperature control element is displayed in cross section in FIG. 23. Peltier element 554 is positioned on platen surface 551 between brass contacts 552 and 553 and held together with bolts 653 and 654. Brass contacts 552 and 553 act as heat sources and sinks to transfer heat to and from the Peltier element 554. The microfluidic disk sits on brass contact 552. When heating the disk, the top surface of the Peltier element 554 heats brass contact 552, and brass contact 553 is cooled. When cooling the disk, the top surface of the Peltier element 554 cools brass contact 554 and heats brass contact 553. An additional aluminum heat sink 652 is positioned in thermal contact with brass contact 553, providing additional heat sink capacity, enhancing Peltier element 554 performance. Aluminum heat sink 652 is mounted to the platen 551 using screws 651 and 655. Brass contact 552 contains thermistor 606 in a cavity containing alumina-filled epoxy 650 that increases the temperature sensitivity of the thermistor. Thermal grease is applied between pieces 552, 554, 553, and 652 to increase thermal contact between the parts.

In the use of the platen of the invention, the platform of the invention is assembled using thermal grease between the brass contacts and the plastic microfluidics layer. Alternatively, the brass contact is provided as a convex layer that is mechanically clamped to the flexible plastic microfluidics layer.

Alternative embodiments of the platens of the invention include so-called "intelligent" platens comprising one or a multiplicity of microprocessors, thereby permitting a reduced set of connections between the slip ring and the printed circuit board comprising the substrate of the platen. Integrated circuit packages such as a BASIC STAMP II embedded controller can be preprogrammed by the PC to control the distribution of signals through the platen circuitry, thereby requiring only an input power and ground connection between the slip ring and the platen.

DNA Sample Preparation Platform

The invention provides a DNA sample application platform for preparing plasmid and genomic DNA from bacteria or eukaryotic, most preferably mammalian cells. This aspect of the invention is described herein for a single microfluidics structure. However, platforms comprising a multiplicity of these microfluidics structures are provided and are encompassed by the invention, wherein a multiplicity of the microfluidics structures described herein are provided on the platform.

Figure 14:
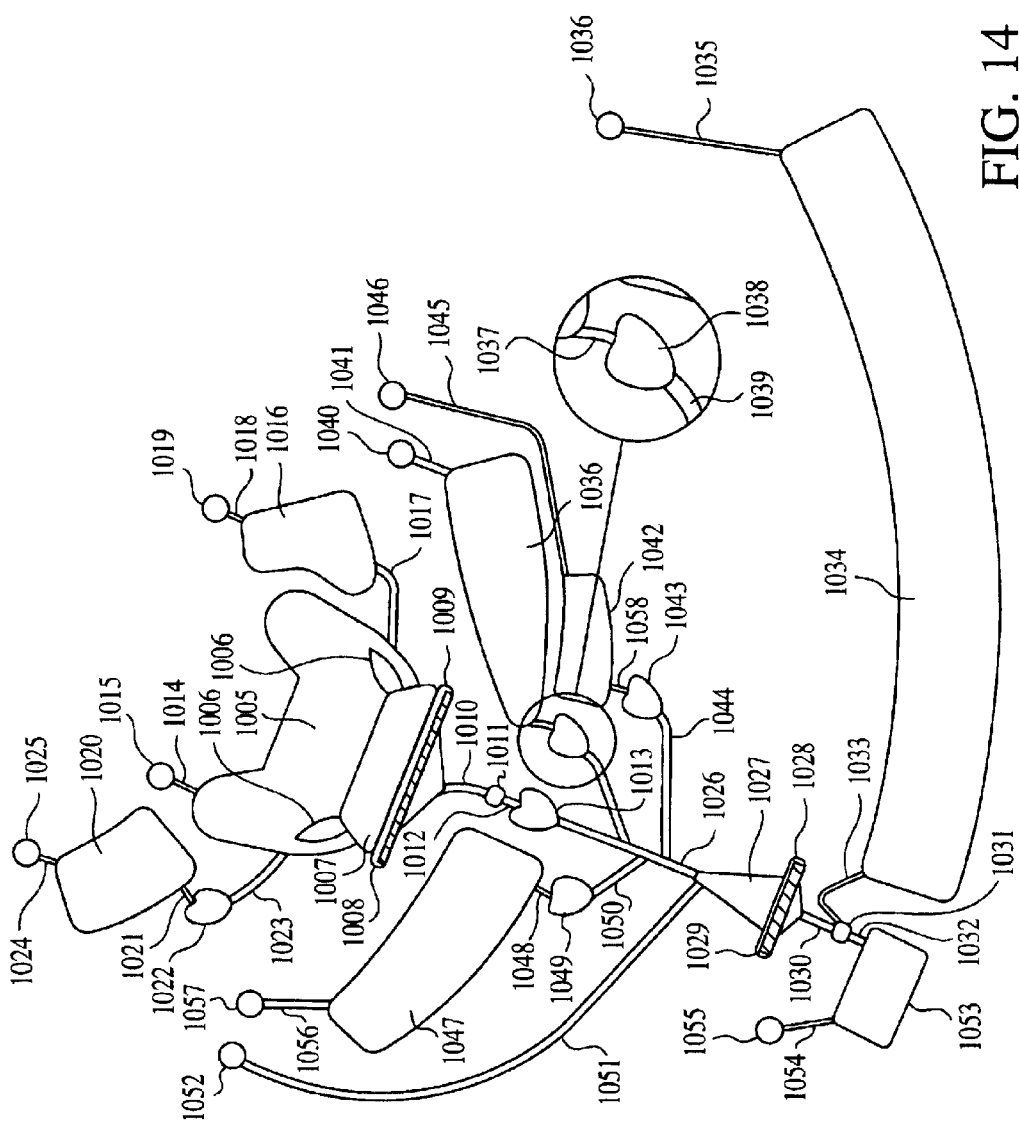
FIG. 14 depicts a plan view of the microfluidics structure for a plasmid DNA preparation platform.

Referring now to the Figures for a more thorough description of the invention, FIG. 14 illustrates one embodiment of sample processing structure of the microfluidics disc in close-up. For orientation, the center of the disc is beyond the top of the Figure. Chamber 1005 has a depth in the platform surface of from about 0.1 cm to about 0.25 cm, about 0.7 cm to 1.5 cm in width and about 0.4 cm to 0.8 cm in length, and has a volumetric capacity of from about 50 $\mu$L to about 1.0 mL (depth 0.2286 cm, width 1.4315 cm, length 0.7879 cm) is a combination sample input chamber and mixing chamber. Within the chamber are mixing baffles 1006 that are from about 0.05 cm to about 0.1 cm wide and from about 0.2 cm to about 0.4 cm long (width 0.1155 cm, length 0.3720 cm) for producing turbulent fluid motion in the chamber upon disc rotation, particularly disc rotation that changes direction rapidly and/or repeatedly. In a position in chamber 1005 most radially most distal from the center of rotation is slot 1008 having depth in the platform surface of from about 0.1 cm to about 0.25 cm (depth 0.2286 cm, width 1.0537 cm, length 0.0794 cm), which contains frit material in which a filter 1009 is placed. The frit material is manufactured by Porex, X-4588, 70 $\mu$m pore size, and the filter is a Whatman filter paper #54 which is placed further out radially on the disc from the frit material. The frit material acts in this application as a filter that, as a porous membrane, allows the liquid to flow through but retains the precipitate. The filter paper in this case is used as a final filtration step; the frit has filtered the majority of the precipitate, but the filter paper has a finer pore size that allows little to no precipitate through. Chamber 1005 is also equipped with an inclined portion 1007 where the depth of the platform decreases in a radially-outward direction and rises from the chamber floor to a depth from about 0.1 cm to about 0.25 cm (depth 0.2286 cm) to form the inner edge of filter slot 1008; the depth of the inner portion of the slot (depth 0.1524 cm) is intermediate between the floor of the chamber 1005 and the top surface of the disc, and thus forms a gap through which fluids flow upon disc rotation at sufficient speed. Entry port 1015 is fluidly connected to chamber 1005 through microchannel 1014, having dimensions of from about 0.001 cm to 0.2 cm in depth, about 0.0125 cm to about 0.025 cm in length and cross-sectional dimension of from about 0.001 cm to about 0.2 cm (depth 0.0254 cm, width 0.0254 cm, length 0.2118 cm). Entry port 1015 is preferably adapted to fluidics loading devices such as pipettors and automated embodiments thereof.

On the radially-distal side of filter 1009, the radially-outward exit from chamber 1005 is fluidly-connected to microchannel 1010 having a depth in the platform surface of from about 0.001 cm to about 0.2 cm, length of from about 0.01 cm to about 0.025 cm and cross-sectional dimension of from about 0.001 cm to about 0.2 cm (depth 0.0508 cm, width 0.0508 cm, length, 0.2631 cm). Microchannel 1014 is fluidly connected to pocket 1011 that defines the edge of sacrificial valve 1012. This pocket 1011 has a depth in the platform surface of from about 0.05 cm to about 0.1 cm, length of from about 0.04 cm to about 0.08 cm in length and cross-sectional dimension of from about 0.05 cm to about 0.1 cm (depth 0.1016 cm, width 0.1060 cm, length 0.0762 cm), on the radially-distal extent of which is sacrificial valve 1012 wherein the sacrificial valve is preferably made using wax or other material as set forth more fully in co-owned U.S. Pat. No. 6,063,589, issued May 16, 2000, incorporated by reference, and recrystallization chamber 1013, where melted wax resolidifies without blocking the flow path. Sacrificial valve 1012 has a depth in the platform surface of from about 0.001 cm to about 0.2 cm, length of from about 0.05 cm to about 0.1 cm in length and cross-sectional dimension of from about 0.001 cm to about 0.2 cm (depth 0.0254 cm, width 0.0254 cm, length 0.1056 cm), and recrystallization chamber 1013 has dimensions of from about 0.75 cm to about 0.15 cm deep, from about 0.1 cm to about 0.25 cm long and from about 0.1 cm to about 0.2 cm wide (depth 0.1524 cm, width 0.2031 cm, length 0.2351 cm). As is disclosed more fully herein, sacrificial valve 1012 is in thermal contact with a heating element, most preferably a resistive heater or Peltier heater, wherein the wax comprising the valve is melted by operation of the heater. In preferred embodiments, the heater is constructed in a platform layer beneath, most preferably immediately beneath, the valve, or alternatively comprises a separate platen positioned to have the heater be above or below, most preferably immediately above or below, the valve. Microchannel 1011 and recrystallization chamber 1013 serve to define the length of sacrificial valve 1012, and wax when deposited in the molten state is naturally confined to this short length of channel by the openings of 1011 and 1013.

Lysis solution reservoir 1016 is positioned radially on the disc substantially at the same distance from the axis of rotation as chamber 1005. Lysis solution reservoir 1016 has a depth in the platform surface of from about 0.1 cm to about 0.25 cm, about 0.18 cm to 0.36 cm in width and about 0.3 cm to 0.8 cm in length, and has a volumetric capacity of from about 25 μL to about 300 μL(depth 0.2286 cm, width 0.3579 cm at the top and 0.5536 cm at the bottom, length 0.7292 cm)and is fluidly connected to chamber 1005 through microchannel 1017. Lysis solution is most preferably applied fresh to the platform before use using entry port 1019 that is fluidly connected to lysis solution reservoir 1016 through microchannel 1017. In these structures, entry port 1019 is preferably adapted to fluidics loading devices such as pipettors and automated embodiments thereof, and microchannel 1017 has dimensions of from about 0.001 cm to about 0.2 cm deep, from about 0.25 cm to about 0.5 cm in length and cross-sectional dimension of from about 0.001 cm to about 0.2 cm (depth 0.0508 cm, width 0.0508 cm, length 0.4845 cm).

Precipitant buffer reservoir 1020 is also positioned radially on the disc substantially at the same distance from the axis of rotation as chamber 1005. Precipitant buffer reservoir 1020 has a depth in the platform surface of from about 0.1 cm to about 0.25 cm, about 0.4 cm to 0.8 cm in width and about 0.25 cm to 0.50 cm in length, and has a volumetric capacity of from about 35 μL to about 400 μL (depth 0.2286 cm, width 0.7349 cm, length 0.4960 cm) and is fluidly connected to chamber 1005 through microchannel 1023. Between precipitant buffer reservoir 1020 and microchannel 1023 is sacrificial valve 1021 and recrystallization chamber 1022, arrayed substantially as described above for sacrificial valve 1012 and recrystallization chamber 1013. Precipitant buffer solution is most preferably applied fresh to the platform before use using entry port 1025 that is fluidly connected to precipitant buffer reservoir 1020 through microchannel 1024. In these structures, entry port 1020 is preferably adapted to fluidics loading devices such as pipettors and automated embodiments thereof, and microchannel 1024 has dimensions of from about 0.001 cm to about 0.2 cm deep, from about 0.25 cm to about 0.5 cm in length and cross-sectional dimension of from about 0.001 cm to about 0.2 cm (depth 0.0508 cm, width 0.0508 cm, length 0.4845 cm).

Radially distal to sacrificial valve 1012 is microchannel 1026, which is thereby fluidly connected to chamber 1005. Microchannel 1026 has dimensions of from about 0.001 cm to about 0.2 cm deep, from about 0.025 cm to about 0.05 cm in length and cross-sectional dimension of from about 0.001 cm to about 0.2 cm (depth 0.1524 cm, width 0.0508 cm, length 0.7060 cm). Microchannel 1026 is fluidly connected to binding column 1027, which further comprises a DNA affinity matrix. Binding column 1027 has dimensions of from about 0.10 cm to about 0.2 cm deep, from about 0.3 cm to about 0.65 cm in length and cross-sectional dimension of from about 0.2 cm to about 0.4 cm, and has a volumetric capacity of from about 5 to about 20 μL (depth 0.1875 cm, width 0.3511 cm at the bottom, 0.04 cm at the top, length 0.5727 cm). Binding column 1027 also comprises matrix material slot 1028 having a depth in the platform surface of from about 0.1 cm to about 0.25 cm and is from about 0.05 cm to about 0.1 cm in length and cross-sectional dimension of from about 0.25 cm to about 0.5 cm, and has a volumetric capacity of from about 5 μL to about 15 μL (depth 0.2383 cm, width 0.5082 cm, length 0.0921 cm), that when assembled contains matrix material 1029, structurally supported by a frit. The binding material consists of Whatman Glass Fiber filter (GF-F) that is a glass fiber that binds the DNA when the DNA is in a chaotropic salt solution where the hydration shell of the DNA is disrupted. The frit material is a solid porous material (70 μm size pores) that is used in this case to provide a solid support backing for the glass fiber that is too flexible to support itself within the structure. Binding column 1027 is also equipped with an air displacement channel 1051, having a depth in the platform surface of from about 0.001 cm to about 0.2 cm and is from about 1.75 cm to about 3.5 cm in length and cross-sectional dimension of from about 0.001 cm to about 0.2 cm (depth 0.1524 cm, width 0.0508 cm, length 3.1955 cm) and air vent 1052, which are constructed to permit air to be displaced from the binding column upon fluid flow therethrough without permitting fluid to flow into air displacement channel 1051.

Microchannel 1030, having a depth in the platform surface of from about 0.001 cm to about 0.2 cm, cross-sectional dimension of from about 0.001 cm to about 0.2 cm, and being from about 0.1 cm to about 0.2 cm in length(depth 0.0508 cm, width 0.0508 cm, length 0.2041 cm), is fluidly connected to pocket 1031 which defines the edge of sacrificial valve 1032. This pocket has a depth in the platform surface of from about 0.05 cm to about 0.1 cm, length of from about −0.04 cm to about 0.08 cm in length and cross-sectional dimension of from about 0.06 cm to about 0.12 cm (depth 0.1016 cm, width 0.1121 cm, length 0.0762 cm). Pocket 1031 is separated from sample collection reservoir 1053 by sacrificial-valve channel 1032 having a depth in the platform surface of from about 0.001 cm to about 0.2 cm, cross-sectional dimension of from about 0.001 cm to about 0.2 cm, and being from about 0.05 cm to about 0.1 cm in length (depth 0.0254 cm, width 0.0254 cm, length 0.0876 cm), which is constructed as described above for sacrificial valves 1012 and 1021. Sample collection reservoir 1053 has dimensions of from about 0.1 cm to about 0.25 cm deep, from about 0.3 cm to about 0.6 cm in length and cross-sectional dimension of from about 0.2 cm to about 0.4 cm, and has a volumetric capacity of from about 20 μL to about 250 μL (depth 0.2286 cm, width 0.6132 cm, length 0.3748 cm). Sample collection reservoir is equipped with air displacement channel 1054 and air vent 1055. Air displacement channel 1054 has a depth in the platform surface of from about 0.001 cm to about 0.2 cm and is from about 0.2 cm to about 0.4 cm in length and cross-sectional dimension of from about 0.001 cm to about 0.2 cm (depth 0.0254 cm, width 0.0254 cm, length 0.3316 cm). These structures are constructed to permit air to be displaced from the binding column upon fluid flow therethrough without permitting fluid to flow into air displacement channel 1054.

Leading radially inward from pocket 1031 is microchannel 1033 having dimensions of from about 0.001 cm to about 0.2 cm deep, from about 0.025 cm to about 0.50 cm in length and cross-sectional dimension of from about 0.001 cm to about 0.2 cm (depth 0.0254 cm, width 0.0254 cm, length 0.4195 cm). In some embodiments, microchannel 1033 is treated to present a hydrophobic surface resistant to wetting by fluids. Along the extent of this microchannel is a bend that turns the microchannel direction radially outward and leads to waste reservoir 1034. Waste reservoir 1034 has dimensions of from about 0.15 cm to about 0.3 cm deep, from about 0.3 cm to about 0.6 cm in length and cross-sectional dimension of from about 2.5 cm to about 5.0 cm, and has a volumetric capacity of from about 350 μL to about 1.5 mL(depth 0.2794 cm, width 4.4783 cm, length 0.5687 cm). The waste reservoir is equipped with air displacement channel 1035 and air vent 1099. Air displacement channel 1035 has a depth in the platform surface of from about 0.001 cm to about 0.2 cm and is from about 0.5 cm to about 1.0 cm in length and cross-sectional dimension of from about 0.001 cm to about 0.2 cm (depth 0.0254 cm, width 0.0254 cm, length 0.9240 cm). These structures are constructed to permit air to be displaced from the binding column upon fluid flow therethrough without permitting fluid to flow into air displacement channel 1035.

The sample preparation microstructures of the platform also comprise first and second wash reservoirs 1036 and 1047. First wash reservoir 1036 has dimensions of from about 0.1 cm to about 0.25 cm deep, from about 0.23 cm to about 0.46 cm in length and cross-sectional dimension of from about 0.75 cm to about 1.5 cm, and has a volumetric capacity of from about 50 $\mu$L to about 600 $\mu$L (depth 0.2286 cm, width 1.3357 cm, length 0.4600 cm). This reservoir is fluidly connected to microchannel 1026 by microchannel 1039, which is interrupted by sacrificial valve 1037 and recrystallization chamber 1038, arrayed substantially as described above for sacrificial valve 1012 and recrystallization chamber 1013. Sacrificial valve 1037 has dimensions of from about 0.01 cm to about 0.03 cm, length of from about 0.08 cm to about 0.12 cm in length and cross-sectional dimension of from about 0.01 cm to about 0.03 cm (depth 0.0254 cm, width 0.0254 cm, length 0.1007 cm). Recrystallization chamber 1038 has dimensions of from about 0.1 cm to about 0.2 cm deep, from about 0.15 cm to about 0.3 cm in length and cross-sectional dimension of from about 0.15 cm to about 0.3 cm (depth 0.1524 cm, width 0.2126 cm, length 0.2302 cm) and microchannel 1039 has dimensions of from about 0.01 cm to about 0.2 cm deep, from about 0.3 cm to about 0.6 cm in length and cross-sectional dimension of from about 0.001 cm to about 0.2 cm (depth 0.1524 cm, width 0.0508 cm, length 0.5910 cm. First wash solution is most preferably applied fresh to the platform before use using entry port 1040 that is fluidly connected to precipitant buffer reservoir 1036 through microchannel 1041. In these structures, entry port 1040 is preferably adapted to fluidics loading devices such as pipettors and automated embodiments thereof, and microchannel 1041 has dimensions of from about 0.001 cm to about 0.2 cm deep, from about 0.15 cm to about 0.3 cm in length and cross-sectional dimension of from about 0.001 cm to about 0.2 cm (depth 0.0254 cm, width 0.0508 cm, length 0.2521 cm).

First wash reservoir 1047 has dimensions of from about 0.1 cm to about 0.25 cm deep, from about 0.25 cm to about 0.5 cm in length and cross-sectional dimension of from about 0.75 cm to about 1.5 cm, and has a volumetric capacity of from about 75 $\mu$L to about 850 $\mu$L (depth 0.2388 cm, width 1.4180 cm, length 0.5065 cm). This reservoir is fluidly connected to microchannel 1026 by microchannel 1050, which is interrupted by sacrificial valve 1048 and recrystallization chamber 1049, arrayed substantially as described above for sacrificial valve 1012 and recrystallization chamber 1013. Sacrificial valve 1048 has dimensions of from about 0.001 cm to about 0.2 cm deep, from about 0.05 cm to about 0.1 cm in length and cross-sectional dimension of from about 0.001 cm to about 0.2 cm (depth 0.0254 cm, width 0.0254 cm, length 0.1023 cm). Recrystallization chamber 1049 has dimensions of from about 0.75 cm to about 1.5 cm deep, from about 0.15 cm to about 0.3 cm in length and cross-sectional dimension of from about 0.15 cm to about 0.3 cm (depth 0.1524 cm, width 0.2179 cm, length 0.2435 cm) and microchannel 1050 has dimensions of from about 0.001 cm to about 0.2 cm deep, from about 0.2 cm to about 0.4 cm in length and cross-sectional dimension of from about 0.001 cm to about 0.2 cm (depth 0.1524 cm, width 0.0508 cm, length 0.3724 cm) Second wash solution is most preferably applied fresh to the platform before use using entry port 1057 that is fluidly connected to precipitant buffer reservoir 1047 through microchannel 1056. In these structures, entry port 1057 is preferably adapted to fluidics loading devices such as pipettors and automated embodiments thereof, and microchannel 1056 has dimensions of from about 0.001 cm to about 0.2 cm deep, from about −0.25 cm to about 0.5 cm in length and cross-sectional dimension of from about 0.001 cm to about 0.2 cm (depth 0.0254 cm, width 0.0508 cm, length 0.4347 cm).

Elution buffer reservoir 1042 is positioned radially more distal from the center of rotation than first or second wash reservoirs 1036 and 1047. Elution buffer reservoir 1042 has dimensions of from about 0.1 cm to about 0.25 cm deep, from about 0.15 cm to about 0.3 cm in length and cross-sectional dimension of from about 0.4 cm to about 0.8 cm, and has a volumetric capacity of from about 20 $\mu$L to about 250 $\mu$L (depth 0.2286 cm, width 0.7308 cm, length 0.2787 cm) and is fluidly connected to microchannel 1026 by microchannel 1044, which is interrupted by sacrificial valve 1058 and recrystallization chamber 1043, arrayed substantially as described above for sacrificial valve 1012 and recrystallization chamber 1013. Sacrificial valve 1058 has dimensions of from about 0.001 cm to about 0.2 cm deep, from about 0.05 cm to about 0.1 cm in length and cross-sectional dimension of from about 0.001 cm to about 0.2 cm (depth 0.0254 cm, width 0.0254 cm, length 0.1012 cm). Recrystallization chamber 1043 has dimensions of from about 0.075 cm to about 0.15 cm deep, from about 0.15 cm to about 0.3 cm in length and cross-sectional dimension of from about 0.15 cm to about 0.3 cm (depth 0.1524 cm, width 0.2126 cm, length 0.2302 cm) and microchannel 1044 has dimensions of from about 0.001 cm to about 0.2 cm deep, from about 0.025 cm to about 0.05 cm in length and cross-sectional dimension of from about 0.001 cm to about 0.2 cm (depth 0.1524 cm, width 0.0508 cm, length 0.8586 cm). Second wash solution is most preferably applied fresh to the platform before use using entry port 1057 that is fluidly connected to precipitant buffer reservoir 1047 through microchannel 1056. In these structures, entry port 1057 is preferably adapted to fluidics loading devices such as pipettors and automated embodiments thereof, and microchannel 1056 has dimensions of from about 0.001 cm to about 0.2 cm deep, from about 1.0 cm to about 2.0 cm in length and cross-sectional dimension of from about 0.001 cm to about 0.2 cm (depth 0.0254 cm, width 0.0254 cm, length 1.6623 cm).

The microfluidics structure as disclosed herein are preferably operated in thermal contact with a heater layer, which can be another layer of the platform or provided as a separate platen element as disclosed herein.

Figure 15:
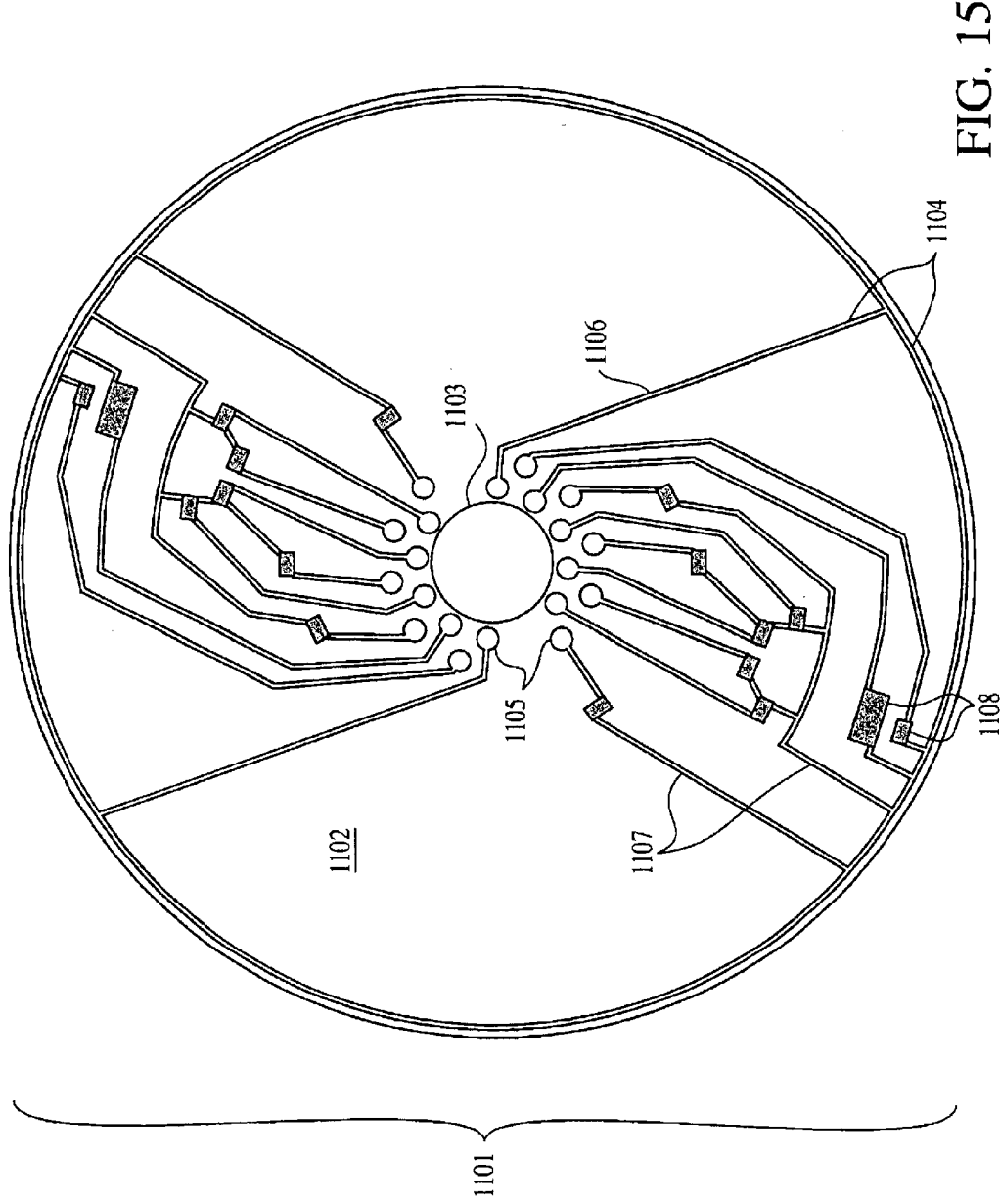
FIG. 15 depicts a plan view of the heating layer for a plasmid DNA preparation platform.
Figure 16:
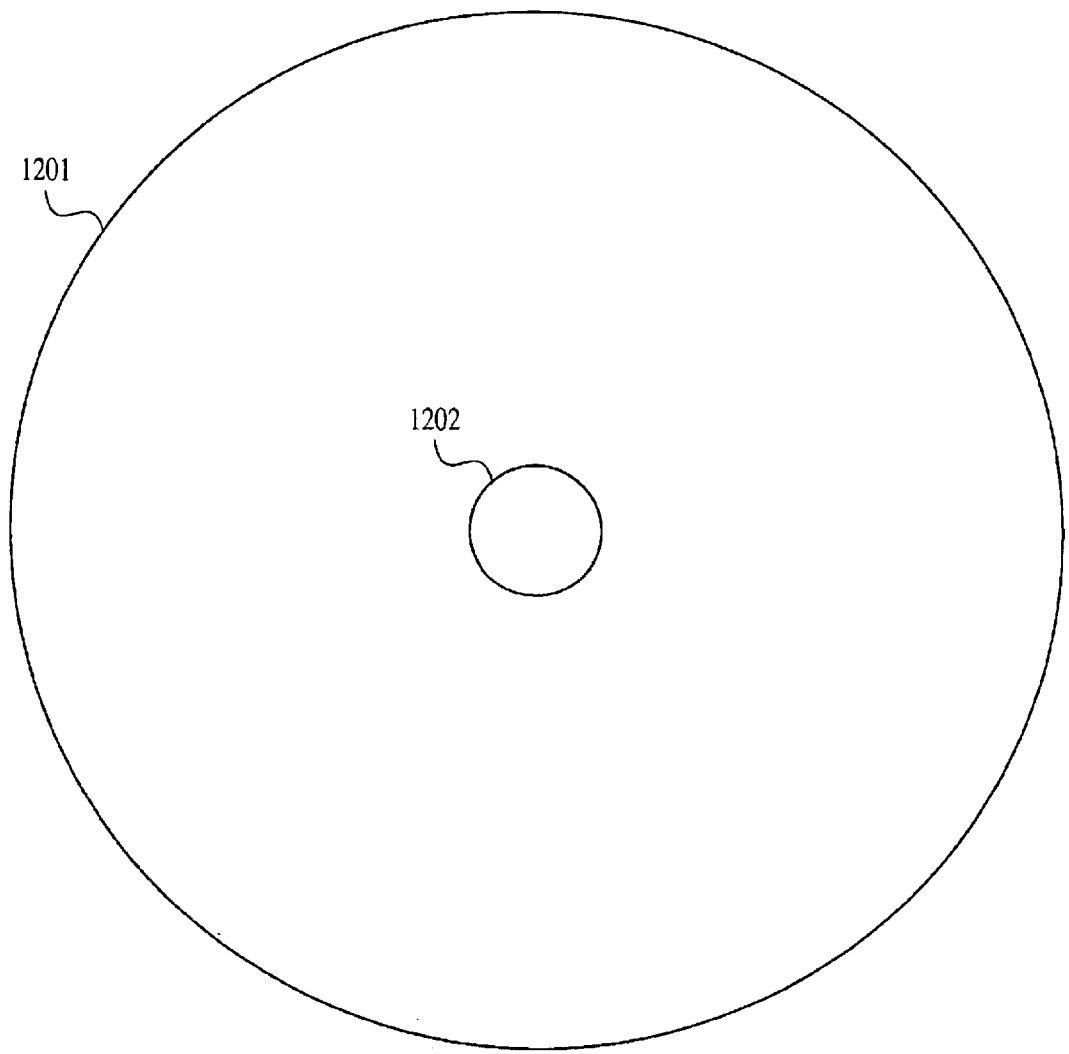
FIG. 16 depicts a plan view of a base layer for a plasmid DNA preparation platform.

In embodiments of the platform wherein the heater layer comprises a separate layer of the platform itself, the heater layer serves both to seal the reservoir layer, thereby forming enclosed chambers out of the pockets in the surface of that disc, and to provide localized heating through an array of electrical leads and heaters. Heater layer 1101 and component structures thereof is illustrated in FIG. 15. Heater layer 1101 consists of a flexible plastic sheet 1102 (most preferably a Mylar sheet, commercially available from ICI, and having a thickness of about 0.00762 cm) onto which are printed or otherwise deposited electrical leads 1104 having a width of from about 0.05 cm to about 0.07 cm (width 0.0508 cm) and a length that from about 1 to 10 cm arrayed on the surface of the heater layer. Heaters 1108 arc also printed or otherwise deposited on flexible plastic sheet 1102 and have dimensions of from about 0.1 to about 1 cm wide (width 0.6891 cm to 0.2032 cm) and from about 0.1 to about 0.5 cm long (length 0.2032 to 0.2067 cm). Electrical leads 1104 are preferably constructed of a conductive material, such as a silver-based ink, while heaters 1108 are preferably constructed of a resistive material, such as a carbon-based ink(having a thickness of printed material on Mylar sheet of about 10 μm). The electrical circuit consists of contact pads 1105 having a radius of about 0.1 to 0.2 cm (radius 0.1397 cm) arrayed near the center of the heater layer which may be contacted by a pin assembly on the micromanipulation instrument; when contacting these pins, closed electrical circuits may be formed in which the instrument forms one part and the heater layer the other part. These types of electrical connections between the heater layer and the instrument are more fully disclosed in co-owned U.S. Pat. No. 6,063,589, issued May 16, 2000 and incorporated by reference herein. Lead 1106 forms a common source or sink of current. Leads 1107 branch from this common lead through the heater elements 1108, and are then connected to the various pads 1105. When a source of high voltage is applied to pads corresponding to individual heaters and the contact pad associated with 1106 is grounded, electrical current flows through the lead and the resistive element, which dissipates energy and generates heat.

Finally, in some embodiments the platform also comprises a base layer 1201 that serves to insulate the platform for more efficient heating using the heater later. The structure of the base layer 1201 is simply a thermally-insulating material having a center hole 1202 (having a radius of about 1 to 1.5 cm; radius 1.4351 cm) for mating with the rotor or spindle of the micromanipulation device of the invention.

In the use of the DNA preparation platforms of the invention, cell cultures, particularly bacterial cell cultures, are applied to the platform and plasmid DNA is isolated by cell lysis, separation of plasmid DNA from bacterial cell debris, cell proteins and cell genomic DNA, plasmid DNA capture on an affinity matrix that is washed to effect a buffer change, thereby removing components of the isolation solutions that are incompatible with down-stream uses of the isolated plasmid DNA; and plasmid DNA elution and recovery.

The sequence of fluid movements through the microfluidics structures of the plasmid DNA preparation platforms of the invention is illustrated in FIG. 17. In the description of the use of the platform, the sizes and amounts of the microfluidics structures, reagents and samples are provided in exemplary embodiments parenthetically.

To prepare the platform for use, reagent solutions are applied as follows. An amount of the following solutions are added to the platform: alkaline cell lysis solution from about 25 μL to about 300 L (50 μL) is loaded into reservoir 1016 using entry port 1019 and microchannel 1018; elution buffer from about 20 μL to about 250 μL (40 μL) is loaded into reservoir 1042 using entry port 1046 and microchannel 1045; first wash solution from about 50 μL to about 600 μL (100 μL) is loaded into reservoir 1036 using entry port 1040 and microchannel 1041; second wash solution from about 75 L to about 850 μL (150 μL) is loaded into reservoir 1047 using entry port 1057 and microchannel 1056; and precipitating solution from about 35 μL to about 400 μL (70 μL) is loaded into reservoir 1020 using entry port 1025 and microchannel 1024.

A sample in an amount from about 25 μL to about 300 μL (50 μL) of bacterial culture is then added to chamber 1005 via entry port 1015 and channel 1014.

The platform is then placed into the micromanipulation device, preferably onto a rotor comprising a slip-ring as described herein and in co-owned U.S. Pat. No. 6,063,589, issued May 16, 2000, incorporated by reference, to enable activation of heaters as described herein. For embodiments with a heater layer, the pins of a slip-ring assembly are brought into contact with the pads 1105 of the heater layer. In these embodiments, alignment groove 1003 serves to set the orientation of the slip-ring assembly relative to the disc, as shown in FIG. 15. The heater layer is aligned with the fluidics layer in such a way that the slip ring pin lines up the pin marks on the heater layer.

The disc is then accelerated to the first rotational speed from about 500 to about 1500 rpm sufficient to motivate fluid flow of alkaline cell lysis solution from reservoir 1016 through microchannel 1017 into chamber 1005. The platform is then agitated by being subjected to rapid, positive and negative (i.e., forward and backward) angular accelerations, thereby increasing and decreasing its angular velocity to effect mixing. Mixing baffles 1006 serve to create a circular motion within the fluid, "laminating" the fluid by drawing it into long portions which are folded back onto the main mass of the fluid, as illustrated in the Figure. As the fluid is repeatedly laminated, it is homogenized. For large volumes and systems which are not microfabricated, and with sufficient angular acceleration, the flow within the chamber 1005 is also turbulent, which aids in mixing.

After time sufficient to achieve homogeneous mixing (which will be dependent on the amount of sample and the size of the chamber 1005 and thus empirically determined), bacteria within the sample will have undergone lysis, releasing DNA into the solution. The disc's rotational velocity is then maintained at a second rotational speed from about 500 to about 1500 rpm (???) and the wax valve within capillary 1021 is melted through application of voltage to the corresponding heater pad in thermal contact with the valve. Heat is applied for time sufficient to melt the wax and for the flowing fluid to drive the molten wax out of the capillary and into recrystallization chamber 1022. The angular velocity is maintained until all of the precipitating solution is driven into the mixing chamber.

The disc is then again agitated as described above to effect mixing. The effect of the precipitating solution is to precipitate genomic DNA, proteins and cellular debris components of the homogenous lysis mixture. This precipitation results in aggregates that can be trapped by filter 1009. Described above and in assembly portion of the text—comprised of Porex frit material X-4588, 70 μm pore size and Whatman Filter paper #54.

After sufficient mixing, the disc's rotational velocity is maintained at a third rotational speed from about 500 to about 1500 rpm and the wax valve within capillary 1012 is then melted through application of voltage to the corresponding heater pad in thermal contact with the valve. Heat is applied for time sufficient to melt the wax and for the flowing fluid to drive the molten wax out of the capillary and into recrystallization chamber 1013. The angular velocity is maintained until all of fluid is driven from the mixing chamber through capillaries 1010, 1012, and 1026 into binding column 1027. The cell debris and unwanted precipitates are trapped on the filter 1009.

The platform is rotated at this angular velocity as the fluid is driven via centripetal acceleration through the binding matrix. Because microcapillary 1032 is blocked by a sacrificial valve, fluid is driven into microchannel 1033, with the centrifugally-induced pressure overcoming the hydrophobicity of the surface treatment of the channel. The fluid is then delivered to the waste chamber 1034.

Platform rotation is maintained until all fluid passes through the matrix 1028 in binding chamber 1027, which is typically a porous material. Because the end of microchannel 1033 that is fluidly connected to waste chamber 1034 is more distant from the platform's axis of rotation than the opposite end of the channel, it is possible to draw all fluid out of binding chamber 1027, microchannel 1030, and pocket 1031 by siphoning action. This has the advantage of reducing contamination or backflow between various steps.

Once all of the fluid has been driven through the matrix 1028, plasmid DNA is bound thereto. Typically, these matrix materials present positive charges that attract the negative charges of the DNA. There are several different types of affinity matrices that have been implemented on the disc that utilize the differences in charge between the DNA and the matrix. Both ion exchange resins as well as silicas and glass fibers including diatomaceous earth, refined silica resins, DEAE as well as glass fiber filters have been used to demonstrate the capabilities on the disc to use charge differences to bind DNA. The platform is then rotated at a fourth rotational speed from about 500 to about 1500 rpm while heat is applied to the wax valve within capillary 1037, releasing the first wash solution through microchannels 1039 and then 1026, fluidly connected to binding column 1027. This fluid is driven through the binding matrix and into the waste chamber as previously described. This wash is intended to remove the components of the lysis and precipitating solutions trapped within the matrix material.

The second wash solution contained within reservoir 1047 is then released through melting of its sacrificial valve 1048 and fluid flow through microchannels 1050 and 1026 and into binding chamber 1027 where it is washed through matrix 1028 and into waste chamber 1034.

After these treatments, the bound plasmid DNA on the matrix contains only trace amounts of other fluids and materials used in the sample processing steps. The platform is then rotated at fifth rotational speed from about 500 to about 1500 rpm and sacrificial valve in capillary 1032 is opened through application of heat, opening the fluid connection between matrix 1028 in binding chamber 1027 with sample collection reservoir 1053. Heat is also applied to the sacrificial valve within capillary 1058. Elution buffer is driven through microchannels 1044 and 1026 and binding column 1027 and most particularly through matrix 1028. Because microchannel 1032 is open, fluid preferentially flows into sample collection reservoir 1053. Under these conditions, the topography of microchannel 1033, the hydrophobic coating thereof or both advantageously prevents the fluid from flowing into waste reservoir 1034. The hydrophobic coating also advantageously prevents back-flowing of waste solution into sample collection chamber 1053 through microchannel 1033.

The platform is then brought to a halt and the fluid sample containing isolated plasmid DNA is recovered through port 1055 and microchannel 1054.

Integrated Sample Preparation and In vitro Amplification Platform

The invention also provides platforms having microfluidics structures that are able to perform an integrated suite of biochemical reactions that include DNA sample preparation, in vitro amplification, and product recovery or analysis. This aspect of the invention is described herein for a single microfluidics structure. However, platforms comprising a multiplicity of these microfluidics structures are provided and are encompassed by the invention, wherein a multiplicity of the microfluidics structures described herein are provided on the platform.

Referring now to the Figures for a more thorough description of the invention, FIG. 1 shows an exploded view of an example of a disc for performing a multiplicity of in vitro amplification reactions. The illustrated embodiment of this platform is capable of performing six independent sample prep and PCR operations on six individual samples. Alternative embodiments of the invention, extending the capacity of the platform to larger sample numbers, as well as subdivision and/or combination of samples, is straightforward and is discussed below. The disc shown here performs 96 assays of the general form: mix first fluid A with second fluid B, This disc illustrates that identical assays may be made by repeating microfluidics structures around the disc at a given radius as well as modifying the structures for placement at different radial positions. In this way, it is possible to fully cover the surface of the disc with microfluidics structures for performing assays. The maximum number of assays that may be performed will depend upon the volume of fluid that may be manipulated reproducibly, i.e., the minimum reproducible dimensions with which the disc may be fabricated, and the amount of hydrodynamic pressure required to drive small volumes of fluid through microchannels at convenient rotational rates. Taking these considerations into account, it is estimated that greater than 10,000 assays having volumes of 1–5 nL can be created in a circular platform having a 6 cm radius.

In FIG. 1, the disc 100 comprises at least three components: a microfluidics disc 201, a sealing layer 301, and one or more thermal sealing layers 401. In certain embodiments, microfluidics disc 201 is further provided as a combination of at least two component layers, wherein a reservoir layer 501 is bonded to a microfluidics layer 601. In these embodiments, the bottom face of the reservoir layer, when mated with the microfluidic layer described below, forms a complete network of enclosed channels and reservoirs through which fluids flow under the impetus of centripetal force created by rotation of the platform about a central axis. In all embodiments, fluid flow permits mixing of various component fluids in the assay and movement of the fluids from sample and reagent reservoirs through mixing structures and into assay collection chambers. In addition, fluid flow can be effectuated to include incubation and wash steps, using structures disclosed in co-owned U.S. Pat. No. 6,063,589, issued May 16, 2000 and incorporated by reference herein. Fluid flow rates of from about 1 nL/s to about 1000 µL/s are achieved at rotational speeds of from about 4 to about 30,000 rpm. "Passive" or capillary valves are preferably used to control fluid flow in the platform as described in co-owned U.S. Pat. No. 6,063,589, issued May 16, 2000, and co-owned and co-pending patent applications U.S. Ser. Nos. 08/761,063, filed Dec. 5, 1996; 08/768,990, filed Dec. 18, 1996; 08/910,726, filed Aug. 12, 1997; 08/995,056, filed Dec. 19, 1997; 09/315,114, filed May 19, 1999; 09/579,492, filed May 12, 2000 and 09/595,239, filed Jun. 16, 2000 (Attorney Docket No. 95,1408-XX), the disclosures of each of which are explicitly incorporated by reference herein. In the operation of the platforms of the invention, competition between rotationally-induced hydrostatic pressure and the capillary pressure exerted in small channels and orifices are exploited to provide a rotation-depending gating or valving system. After fluids are deposited in detection chambers positioned towards the outer edge of the platform, a signal, most preferably an optical signal, is detected.

Figure 2:
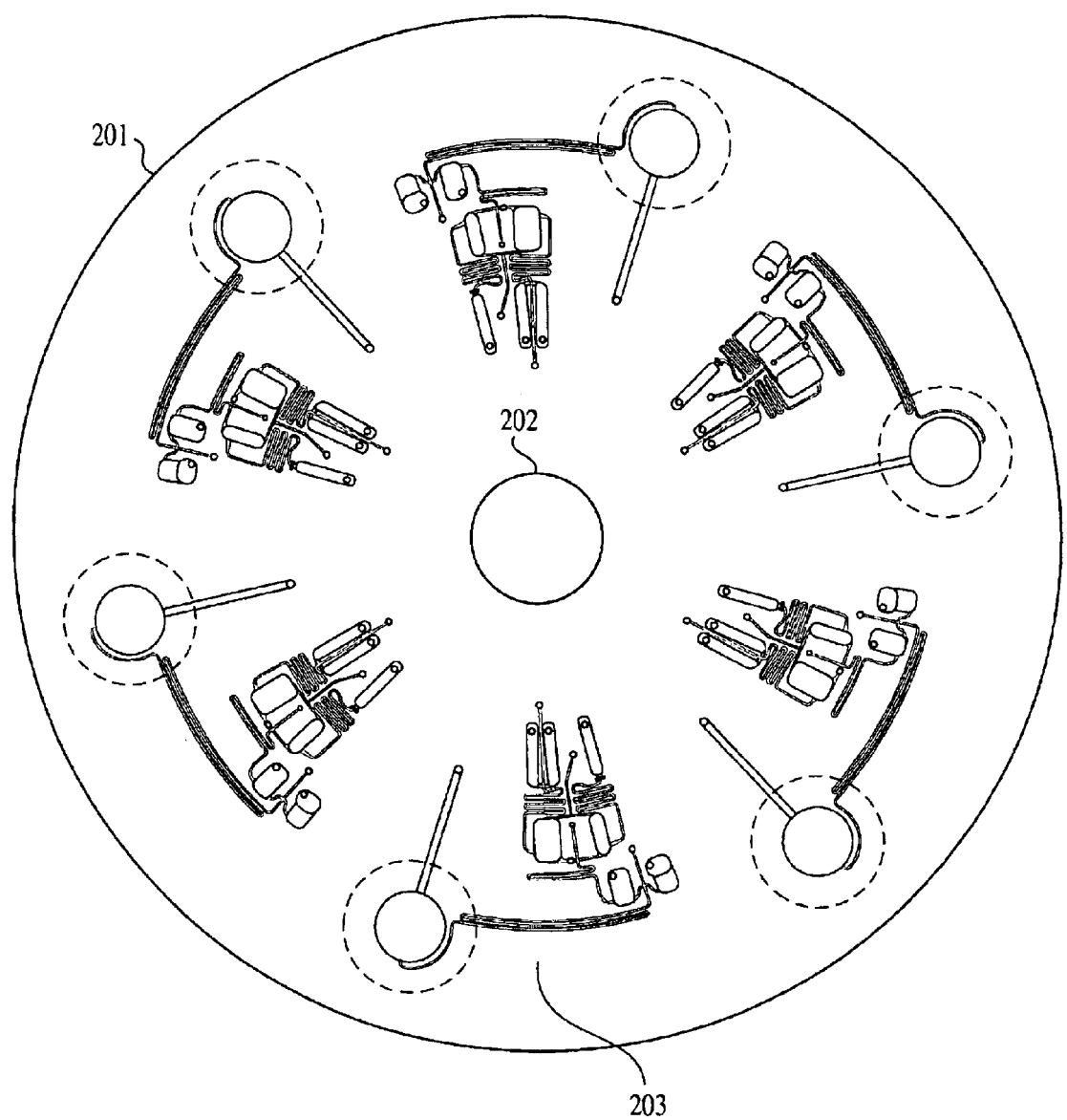
FIG. 2 depicts a plan view of one component of the Microsystems platform shown in exploded, oblique view in FIG. 1, the microfluidics layer

Platform 100 is preferably provided in the shape of a disc, a circular planar platform having a diameter of from about 10 mm to about 50 mm and a thickness of from about 0.1 mm to about 25 mm. The structure of microfluidics disc 201 is shown in FIG. 2, which depicts the "bottom" face to more clearly illustrate this embodiment of the platforms of the invention.

Microfluidics disc 201 is preferably provided in the shape of a disc, a circular planar platform having a diameter of from about 10 mm to about 50 mm and a thickness of from about 0.1 mm to about 25 mm. The disc preferably comprises a center hole 202 for mounting on a spindle, having a diameter of from about 1 mm to about 20 mm. Center hole 202 can be replaced by an extruded fitting for connection to a spindle, or may be absent entirely, in which case registry and connection to the spindle is accomplished using another portion of the surface of the platform. Microfluidics disc 201 can also include registry features such as the groove 203 that permits a clamping fixture above the platform to be brought in proximity with, but not in contact with, the top surface of the platform when the platform is loaded into the spindle. In embodiments having this feature, a pin on the clamping fixture, preferably spring-loaded, slips into the groove as the disc is spun at low rpm, and captures the clamping fixture, thus determining the platform's orientation with respect thereto. In other embodiments, the platform comprises "home-flag" 204, that is a reflective or absorbing stripe that can be positioned on the surface of the platform and sensed by an emitter/photodiode pair as the disc is spun, thus permitting the orientation of the disc with respect to the instrument to be determined.

Figure 3:
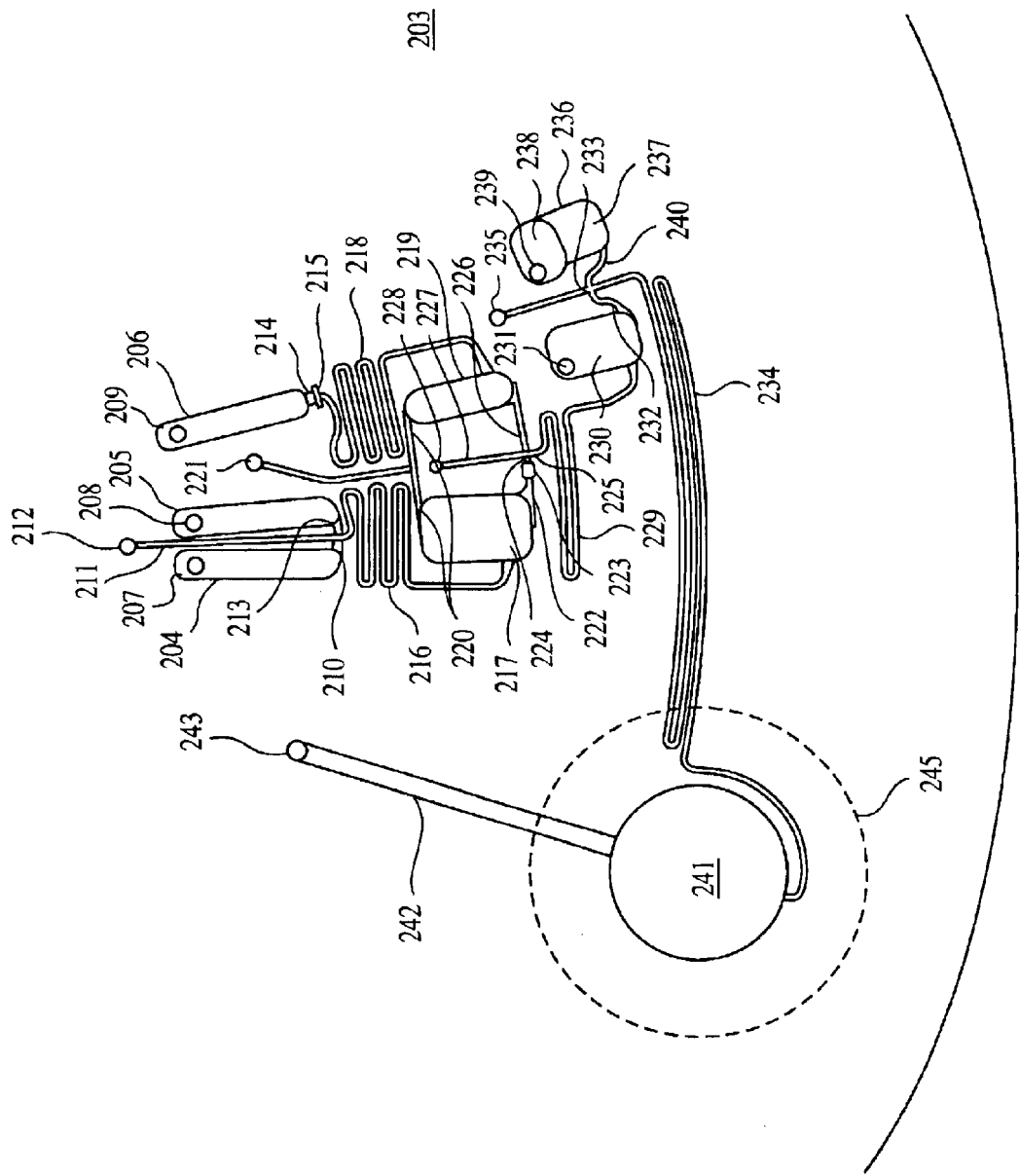
FIG. 3 is a detail of a section of the microfluidics layer illustrated in FIG. 2.

FIG. 3 illustrates an expanded view of a section of the microfluidics disc, with the center of the disc being beyond the top of the figure. Reservoirs 204, 205, and 206 are designed to contain the fluid sample, cell alkaline lysis solution, and neutralizing buffer, respectively. Reservoirs 204 and 205 are designed such their radial position on the disc and extent are identical, and with cross-sectional areas (i.e., depth in the platform×lateral dimension) which form a ratio equal to the desired ratio of fluids to be placed within the reservoirs. Each reservoir has a loading hole (207, 208 and 209, respectively) located in the reservoir at a position proximal to the center of the disc. Each reservoir has dimensions of from about 0.05 mm to about 5 mm wide, from about 0.05 mm to about 20 mm long, and from about 0.05 mm to about 5 mm thick, and has a volumetric capacity of from about 0.1 $\mu$L to about 500 $\mu$L. Loading holes 207, 208 and 209 preferably have dimensions adapted to automated loading devices such as micropipettors, for example, a standard 200 $\mu$L plastic pipette tip having a tip diameter of 1.5 mm; micropipette tips of diameter 1 mm; piezoelectric or ceramic drop delivery systems (such as are sold by the IVEK Corp., Springfield, Vt.); and inkjet-based fluid delivery systems. For non-contact delivery systems such as piezoelectric or inkjet delivery, the dimensions of the ports must be a few times greater than the size of the droplets, e.g., 0.2 nm for a 1 nL drop.

The opposite end of reservoir 204 is fluidly connected to microchannel 210 that preferably is constructed at a different depth in the platform surface than the reservoir. This microchannel ends at capillary 211 that preferably is constructed at a different depth in the platform surface than the microchannel 210. Capillary 211 ends at air-vent 212 located more proximally to the center of the disc than the inner ends of the reservoirs. Reservoir 205 is fluidly connected to microchannel 213 at a position in the reservoir distal to the axis of rotation. Microchannel 213 also ends at capillary 211 as described for microchannel 210. The construction of the microchannels 210 and 213 and the connection of these microchannels to capillary 211 permits air to be displaced by fluid flow from reservoirs 204 and 205, but the cross-sectional area of capillary 211 is constructed to be too small to permit liquid fluid flow therethrough. Reservoir 206 is fluidly connected to microchannel 214 that ends at capillary junction 215.

Microchannels 210 and 213 are fluidly connected to mixing microchannel 216, and permit mixing of the contents of reservoirs 204 (herein illustrated to contain sample) and 205 (herein illustrated to contain alkaline cell lysis solution). Mixing microchannels are configured to provide mixing of different solutions as the mixture traverses the longitudinal extent of the microchannel. The degree of mixing is dependent on the flow rate of the fluids and the longitudinal extent of the mixing microchannel, which is proportional to the amount of time the two fluids are in contact and are mixed together. The degree of mixing is also dependent on the lateral extent of the mixing microchannel, and is further dependent on the diffusion constants of the fluids to be mixed. In order to accommodate mixing microchannels having sufficient lengths for mixing fluids having a useful range of viscosities, the mixing microchannels are provided as shown. Mixing is promoted by configuring the microchannel to bend several times as it traverses a path on the platform surface that is perpendicular to the direction of rotation, but extends radially on the surface of the platform from a position more proximal to a position more distal to the axis of rotation. Mixing microchannel 216 has a length of from about 1 mm to about 100 mm, its length in some cases achieved through the use of bends.

Mixing in the device is promoted through diffusion. If two small volumes A and B are added to a single container, diffusion of A into B and/or B into A will effect mixing. The amount of time required for this mixing will depend upon the diffusion constants of the molecules within the solutions whose mixing is desired and the distances over which the molecules must diffuse. For example, 0.5 microliter of solution A comprising a molecule with diffusion constant D is added to a reservoir 1 mm on a side. Solution B comprising a molecule whose diffusion constant is also D is added. The solutions will initially occupy the volume with an interface partitioning them. Even if the fluids are highly miscible, the diffusion times to create a completely homogeneous solution will be approximately $t=2 \times^2/D$. For $x=0.05$ cm. (0.5 mm) and $D=10^{-5}$ cm$^2$/s, the mixing time is 500 seconds, an unacceptably long time for most reactions. This mixing time may be reduced by mechanical stirring, for example, but stirring is difficult to obtain in fluids confined in small structures because the flow of the fluid is laminar and does not contain turbulent eddies that are known to promote mixing. If, instead of placing fluids A and then B in a 1 mm$^3$ container, fluids A and B were placed side-by-side in a long, thin capillary of lateral dimension d, the relevant time for mixing is much shorter. If, for example, d is 100 microns, mixing time t is 20 seconds. The mixing channels of the device simulate the placement of fluid in a long capillary by co-injecting fluid streams A and B into a capillary microchannel. These fluids flow side-by-side down the channel initially. As the fluid is pushed through the microchannel due to centrifugal force produced by rotation of the platform, diffusion occurs between the fluids. By choosing a capillary of sufficiently narrow diameter, sufficient length, and a pumping rate that is sufficiently low, the portion of A and B of the total volumes of A and B present in the channel during pumping can be caused to mix.

These choices may be determined by setting the required time for mixing equal to the amount of time necessary for the fluid to traverse the channel. The required time for diffusion is $$t_m \approx \frac{2w^2}{D}$$

where w is the lateral size of the channel. The amount of time necessary to traverse the channel is simply the length of the channel divided by the fluid velocity, the velocity being calculated as described in co-owned and co-pending U.S. Ser. No. 08/910,726, filed Aug. 12, 1997, and Duffy et al. (1999, *Anal. Chem.* 11: 4669–4678):

$$t_t = \frac{l}{U} = \frac{l}{\left(\frac{\rho\omega^2 \Delta R \langle R \rangle (d^H)^2}{32\eta l}\right)} = \frac{32\eta l^2}{\rho\omega^2 \Delta R \langle R \rangle (d^H)^2}$$

where the fluid properties are the density ρ and viscosity η, ΔR and <R> are the extent along the radius and average radial position of the fluid subject to centripetal acceleration, and l and $d^d$ are the length and hydraulic diameter of the channel. By choosing variables such that $t_m$, is at least equal to or greater than $t_m$, mixing in the microchannels is assured.

Mixing microchannel is fluidly connected at its end distal to the axis of rotation to reservoir 217. Reservoir 217 has dimensions of from about 0.05 mm to about 5 mm wide, from about 0.05 mm to about 20 mm long, and from about 0.05 mm to about 5 mm thick, and has a volumetric capacity of from about 0.1 nL to about 500 μL, and is equipped at the end of the reservoir proximal to the axis of rotation with air displacement capillary 220 and air vent 221. This permits air to be displaced from the reservoir upon fluid flow through mixing microchannel 216 and delivery to reservoir 217.

Mixing microchannel is fluidly connected at its end distal to the axis of rotation to reservoir 217. Reservoir 217 has dimensions of from about 0.05 mm to about 5 mm wide, from about 0.05 mm to about 20 mm long, and from about 0.05 mm to about 5 mm thick, and has a volumetric capacity of from about 0.1 nL to about 500 μL, and is equipped at the end of the reservoir proximal to the axis of rotation with air displacement capillary 220 and air vent 221. This permits air to be displaced from the reservoir upon fluid flow through mixing microchannel 216 and delivery to reservoir 217.

Capillary junction 215 is fluidly connected to microchannel 218. As illustrated in FIG. 3, this microchannel is preferably configured to have the same length and diameter as mixing microchannel 216 in order to most easily permit delivery of fluid from reservoirs 204 and 205 into reservoir 217, and from reservoir 207 to reservoir 219, to be accomplished simultaneously and coordinately. In alternate embodiments, microchannel 218 is provided having a different length than mixing microchannel 216, since no mixing occurs in microchannel 218. In other alternative embodiments, fluid is loaded directed into reservoir 219. Reservoir 219 has dimensions of from about 0.05 mm to about 5 mm wide, from about 0.05 mm to about 20 mm long, and from about 0.05 mm to about 5 mm thick, and has a volumetric capacity of from about 0.1 nL to about 500 μL, and is equipped at the end of the reservoir proximal to the axis of rotation with air displacement capillary 220 and air vent 221. This permits air to be displaced from the reservoir upon fluid flow through mixing microchannel 218 and delivery to reservoir 219. Reservoirs 217 and 219 are designed such their radial position on the disc are identical, and with cross-sectional areas (depth in the platform x lateral dimension) that form a ratio equal to the desired ratio of fluids to be placed within the reservoirs.

Figure 4:
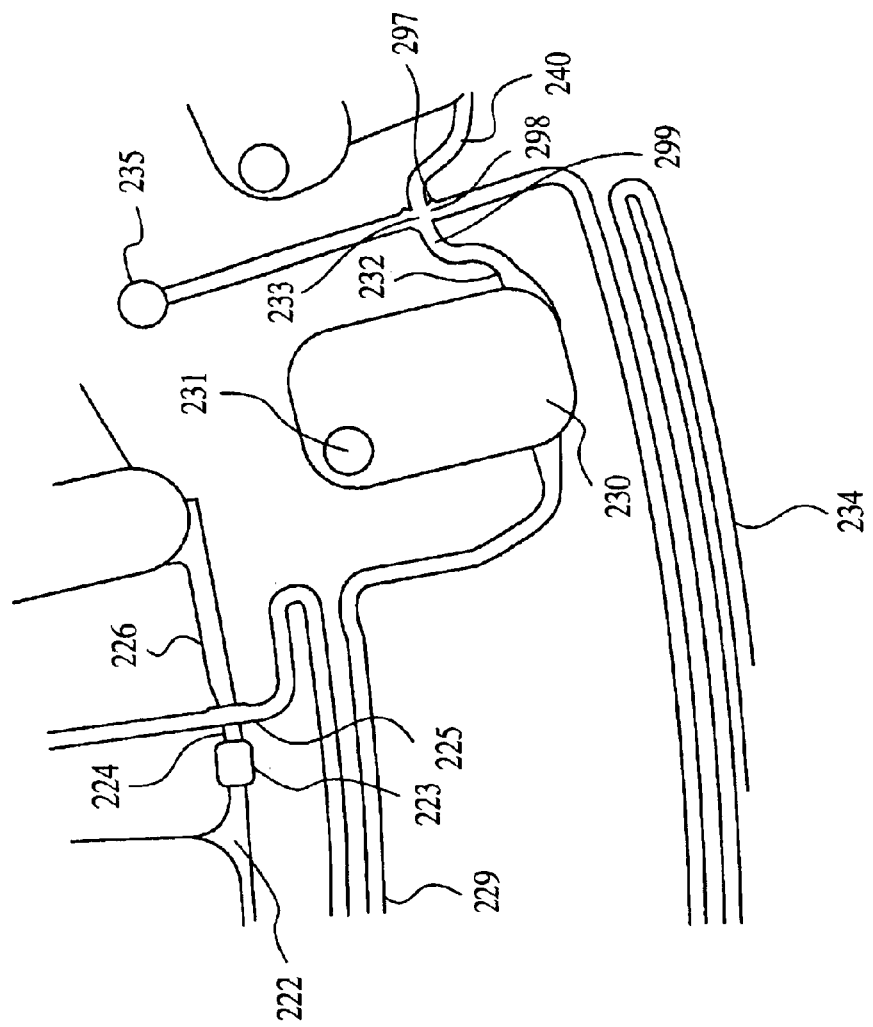
FIG. 4 shows a detail of a region of the structure illustrated in FIG. 3.

Reservoir 217 is fluidly connected to microchannel 222 having a length of from about 0.15 cm to about 0.30 cm (length 0.2552 cm) and terminates at capillary junction 223. On the other side of the capillary junction is microchannel 224 having a length of from about 0.015 cm to about 0.030 cm (length 0.0218 cm) that terminates at air displacement capillary 225. Air displacement capillary 225 is connected by capillary 227 to expansion volume 228; alternatively in some embodiments expansion volume 228 is replaced by air vent 228. The construction of microchannels 222 and 224 and the connection of these microchannels to capillary 227 permits air to be displaced by fluid flow from reservoirs 217 and 219, but the cross-sectional area of capillary 227 is constructed to be too small to permit liquid fluid flow therethrough. These structures are more fully illustrated in FIG. 4.

Reservoir 219 is fluidly connected to microchannel 226 having a length of from about 0.20 cm to about 0.40 cm (length 0.3205 cm) and terminates at air displacement capillary 225, forming a capillary junction therewith. The depth and width of microchannel 226 where it joints capillary 225 is preferably different than the depth and width of microchannels 222 and 224.

Microchannels 224 and 226 are fluidly connected to mixing microchannel 229, designed similarly to mixing microchannel 216 to insure mixing of fluids from reservoirs 217 and 219. Mixing microchannel 229 has a length of from about 1 mm to about 100 mm, its length in some cases achieved through the use of bends, and terminates at reservoir 230, which also contains air-vent 231. Reservoir 230 has dimensions of from about 0.05 mm to about 5 mm wide, from about 0.05 mm to about 20 mm long, and from about 0.05 mm to about 5 mm thick, and has a volumetric capacity of from about 0.1 nL to about 500 μL. Reservoir 230 is fluidly connected to microchannel 232, which is arrayed on the surface of the platform in a direction radially-inward and terminating at air displacement capillary 233. The junction 299 between microchannel 232 and capillary 233 is designed with a smoothly-widening enlargement to substantially inhibit capillary-pinning (valving) action, as described more fully below. This junction 299 is fluidly connected to mixing microchannel 234, the radially-inward end of which is terminated in an expansion volume 235. Reservoir 236 is positioned at the same radial distance from the axis of rotation as reservoir 230. Reservoir 236 has dimensions of from about 0.05 mm to about5 mm wide, from about 0.05 mm to about 20 mm long, and from about 0.05 mm to about 5 mm thick, and has a volumetric capacity of from about 0.1 nL to about 500 μL. In preferred embodiments, a portion 237 of reservoir 236 radially more distal from the axis of rotation has a depth in the surface of the platform that is more shallow than the depth in the surface of the platform of the portion 238 radially more proximal to the axis of rotation. Reservoir 236 also comprises air vent 239, which also serves as a loading port.

Microchannel 240 having dimensions of from about 0.15 cm to 0.3 cm long(length 0.25 cm) and a cross sectional area of from about 0.001 cm to about 0.2 cm fluidly connects reservoir 236 with air displacement capillary 233 at capillary junction 298. In contrast to capillary junction 299, the joint of the microchannel, is designed to provide a "pinning" action, that is, the junction prevents fluid flow. Microchannel 240 is designed to contain a restriction 297 followed by a flared opening in the retrograde direction (i.e., back towards the axis of rotation), connected to capillary 233. Alternative embodiments of capillary junctions, as disclosed more fully in co-owned U.S. Pat. No. 6,063,589 issued May 16, 2000 and in co-owned and co-pending patent applications U.S. Ser. No. 08/910,726, filed Aug. 12, 1997, incorporated by reference herein.

Mixing microchannel 234 having a length of from about 1 mm to about 100 mm, most preferably wherein its length in some cases achieved through the use of bends, terminates at thermal cycling chamber 241. The depth in the platform surface of thermal cycling chamber 241 is determined by the thermal requirements of cycling, as disclosed more fully below. As shown in FIG. 3, the portion of thermal cycling chamber 241 more proximal to the axis of rotation is connected to air channel 242 that terminates in an airvent 243. The chamber also comprises an insulating air pocket 245 that is a depression having a diameter greater than the diameter of thermal cycling chamber 241 in the other face of the disc 201.

Figure 5:
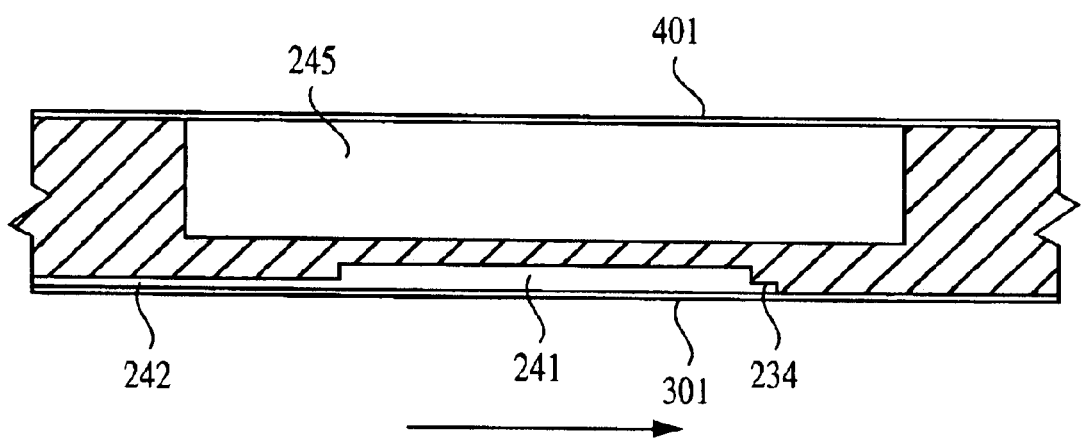
FIG. 5 is a cross-sectional view of the Microsystems platform of FIG. 1 in the vicinity of the thermal cycling chamber.

FIG. 5 illustrates the assembled disc in the region of the thermal cycling chamber in cross-section. The outward radial direction is indicated by the arrow. The thermal cycling chamber 241 is a depression in the face of the disc 201, with channel 234 entering at a position radially distal from the axis of rotation, as shown. Sealing layer 301 is provided as described below to cover thermal cycling chamber 241. Insulating air pocket 245 is shown in he surface of platform 201, covered by sealing layer 301.

The microsystems platforms of the invention are provided to perform in vitro amplification reactions, most preferably in an integrated suite of biochemical reactions including DNA isolation, amplification most preferably using the polymerase chain reaction (PCR) and isolation of the amplified fragment, for detection on-disc or off disc (for example, using conventional gel electrophoresis).

This use of the platforms of the invention is shown in FIGS. 1 through 5; although this use will be understood by those with skill in the art from the disclosure and examples, the functioning of the platform is explicitly described as follows.

The platforms of the invention most preferably accept raw, or at most pre-diluted, biological fluids containing bacteria or eukaryotic cells, or sample of bacterial or eukaryotic, most preferably mammalian cell culture, or biological fluids such as blood comprising mammalian cells, and to process these fluids through the steps of DNA release from the cells and amplification, most preferably via PCR.

Figure 8:
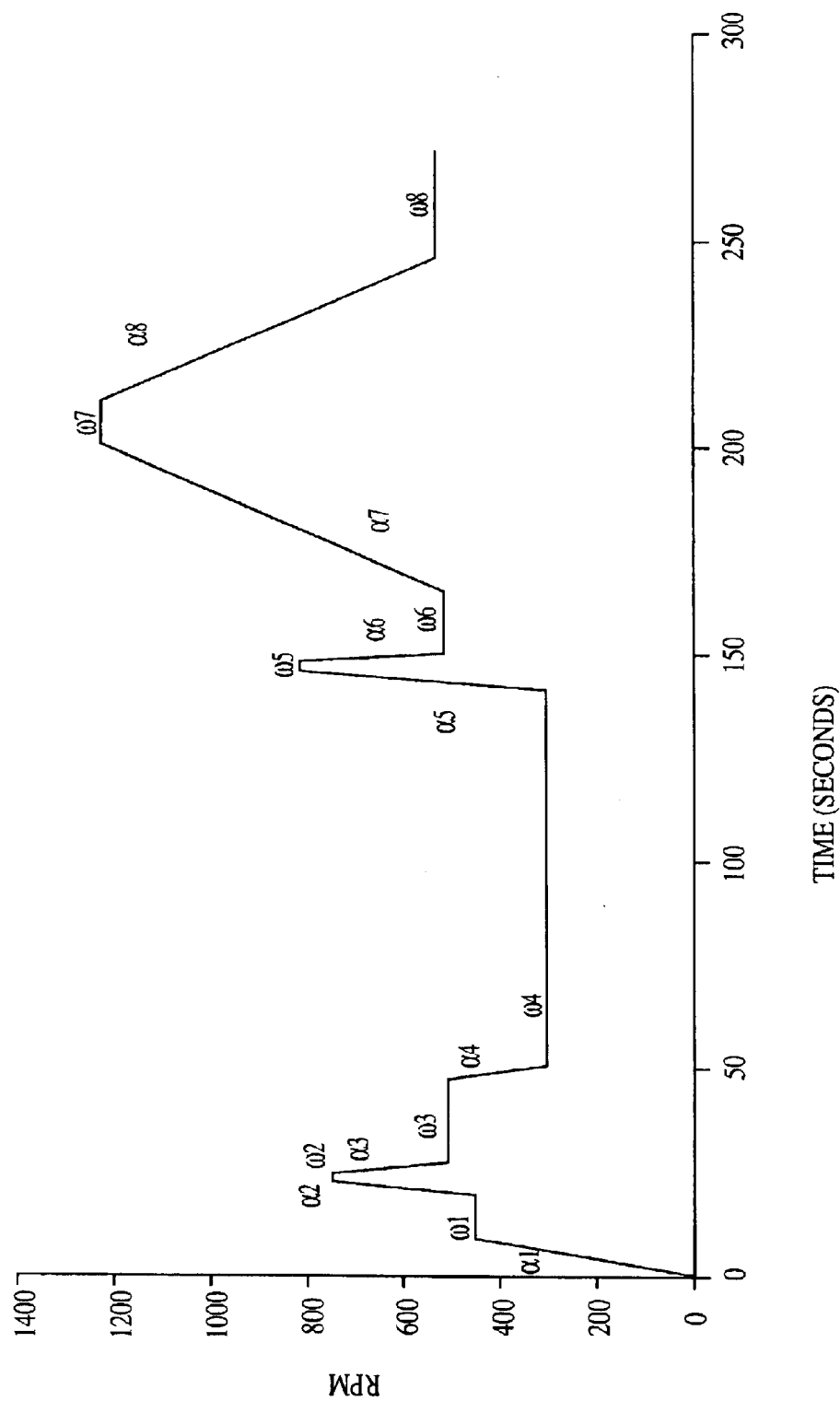
FIG. 8 illustrates the velocity profile, rotational rate (rpm) vs. time, used to effect fluid motion through the Microsystems platform in Examples 1 and 2.
Figure 9A:
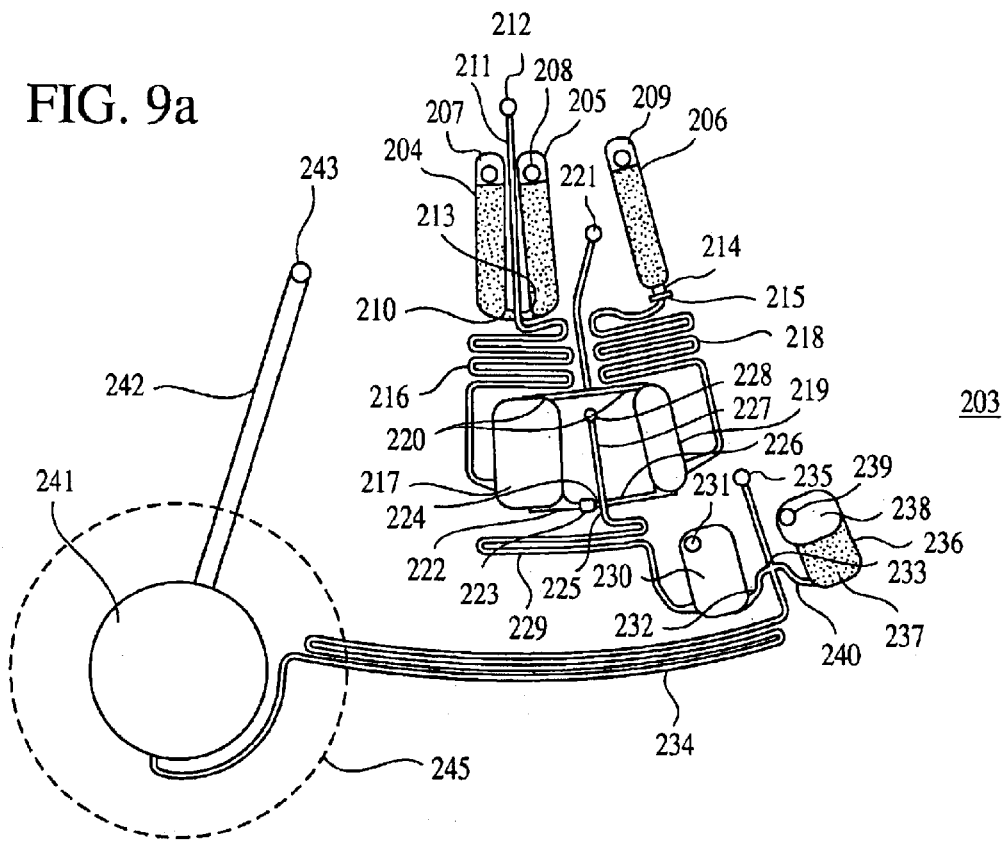
FIG. 9 illustrates the sequence of fluid motions motivated by the velocity profile of FIG. 8.

The fluid sample is added to reservoir 204 through entry port 207, an alkaline cell lysis solution, in one instance, NaOH, is added to reservoir 205 through entry port 208, and a conditioning or neutralization buffer solution, in one example, Tris HCl, is added to reservoir 206 through entry port 209. An amplification solution comprising a balanced mixture of deoxyribonucleotide triphosphates (dNTPs) at a concentration of about 200 $\mu$M, 1–10 Units of a polymerase, most preferably a thermostable polymerase such as Taq polymerase from *Thermus aquaticus*, and buffers and salts, particularly $MgCl_2$, appropriate for the amount of target DNA in the sample and the enzyme (the amount of magnesium chloride is typically determined empirically due to the sensitivity of amplification reactions to the concentration of this salt) is added through entry port 239 into reservoir 237. This is shown in FIG. 9a. The platform is then placed on a micromanipulation device described herein and more fully in co-owned U.S. Pat. No. 6,063,589, and co-owned and co-pending U.S. Ser. Nos. 08/761,063, filed Dec. 5, 1996; 08/768,990, filed Dec. 18, 1996; and 08/910,726, filed Aug. 12, 1997 incorporated by reference. The platform is rotated to motivate fluid flow on the disc in a manner determined by the placement and dimensions of the microfluidics structures on the disc. An exemplary rotational profile is shown in FIG. 8. As shown, the platform is first accelerated gently at angular acceleration $\alpha_1$ to an initial rotational rate $\omega_1$ (slightly higher than 400 rpm in FIG. 8). Rotation is maintained for a time (about 10 seconds in FIG. 8) sufficient to allow the sample and alkaline cell lysis solutions to enter microchannels 210 and 213, flowing until they are stopped ("pinned," as used herein) at the capillary junction with microchannel 211. Similarly, fluid in reservoir 206 flows into microchannel 214 until it is pinned at capillary junction 215. The disc is then accelerated rapidly at angular acceleration $\alpha_2$ to speed $\omega$2 (about 1800 rpm in FIG. 8), which may be maintained for a period (as shown in FIG. 8). The pressure induced by rotation at this speed forces one or both fluids pinned at microchannel 211 to cross the narrow gap of the microchannel and to come in contact with or "wet" the other fluid; this permits the fluids, now in contact, to drain into mixing microchannel 216 under the impetus of rotational speed $\omega_3$ (about 500 rpm in FIG. 8).

As shown in FIG. 3, microchannel 210 has a larger cross-sectional area than microchannel 213, and as a result supports a lower capillary pressure than this microchannel. Consequently, the sample fluid bridges the gap across microchannel 211 first.

Concurrently, the velocity increase that motivates fluid from reservoirs 204 and 205 into mixing microchannel 216 also overcomes capillary junction 215, thereby motivating fluid flow from reservoir 206 into mixing microchannel 218.

Figure 9B:
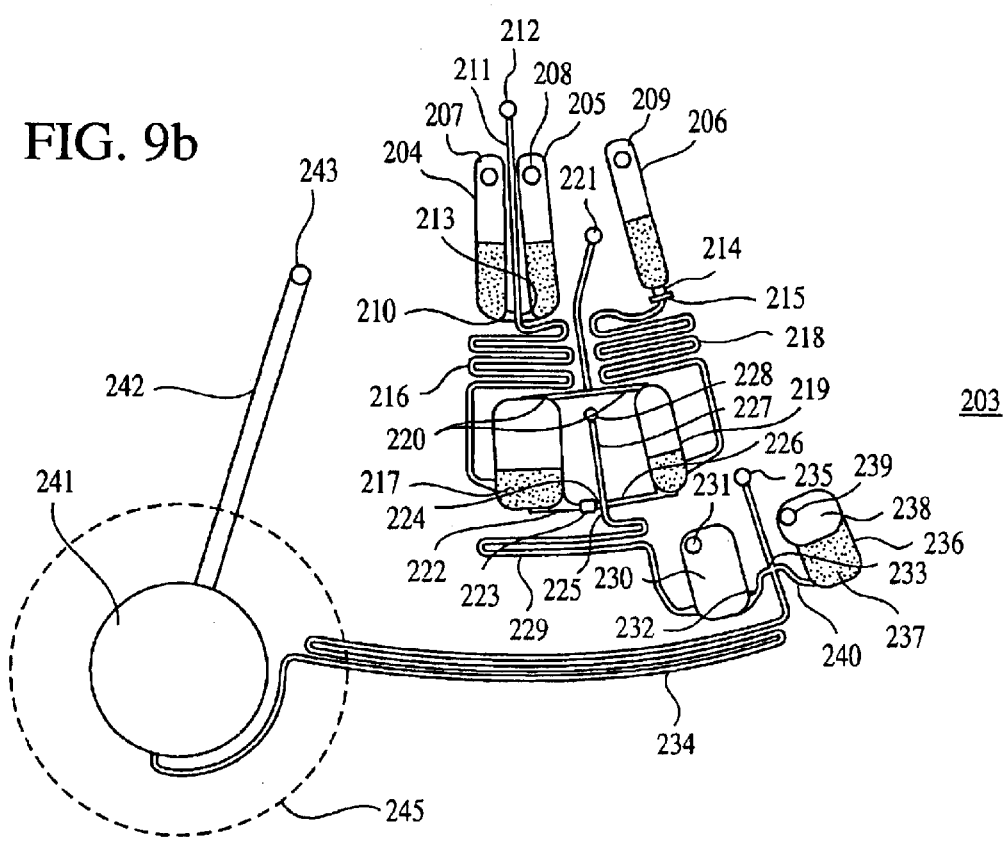

Once the capillary junctions impeding fluid flow out of the reservoirs 204, 205 and 206 have been overcome, the rotational rate is reduced at acceleration $\alpha_3$ to velocity $\omega_3$ (about 500 rpm in FIG. 3); in preferred embodiments, acceleration rate $\alpha_3$ is substantially equivalent to (but has the opposite sign, since this is deceleration) acceleration rate $\alpha_2$; this is shown in the Figure. At this lower speed, the overall pressure driving flow into mixing microchannel 216 is reduced. Because mixing microchannel 216 is narrow and long, it presents considerable hydraulic resistance to flow. At this low speed, pressure differences between the fluids in reservoirs 204 and 205 (as may be occasioned, for example, by these reservoirs having different volumes, for example) are "evened out" as fluids flow into mixing microchannel 216. For example, if the fluid from reservoir 204 initially flows more rapidly than the fluid from reservoir 205 flows, the extent of fluid in the radial direction in reservoir 204 will be smaller than that in reservoir 205 at a larger time; hence the pressure exerted at microchannel 211 will be lower than that exerted by the fluid in reservoir 205, resulting in an increase in flow rate of the fluid in reservoir 205 relative to that in reservoir 204, resulting in an "evening out" of the fluid extents or heads in the radial direction. As a result, the fluids enter in strict ratios equal to the ratios of the cross-sectional areas of the reservoirs. Air displaced by the fluids is vented through channels 220 to air-vent 221. FIG. 9b illustrates the situation at some time at rotational speed $\omega_3$.

The concurrent fluid flow from reservoir 206 through mixing microchannel 219 is accomplished at rotational speed $\omega_3$. Since no actual mixing usually occurs, the shape of microchannel 218 is unimportant as long as the fluid pumped through it does not fill chamber 219 at too high a rotational rate (i.e., before the velocity drops to $\omega_3$).

Rotation at speed rotational speed $\omega_3$ motivates fluid flow from reservoirs 204, 205 and 206 and into reservoirs 217 and 219. In addition to preventing changes in the mixing ratio of fluids from reservoirs 204 and 205, the lower velocity means that the pressure exerted at the outer ends of reservoirs 217 and 219 is low enough not to force the fluids past the capillary junctions designed to retain them.

Figure 9C:
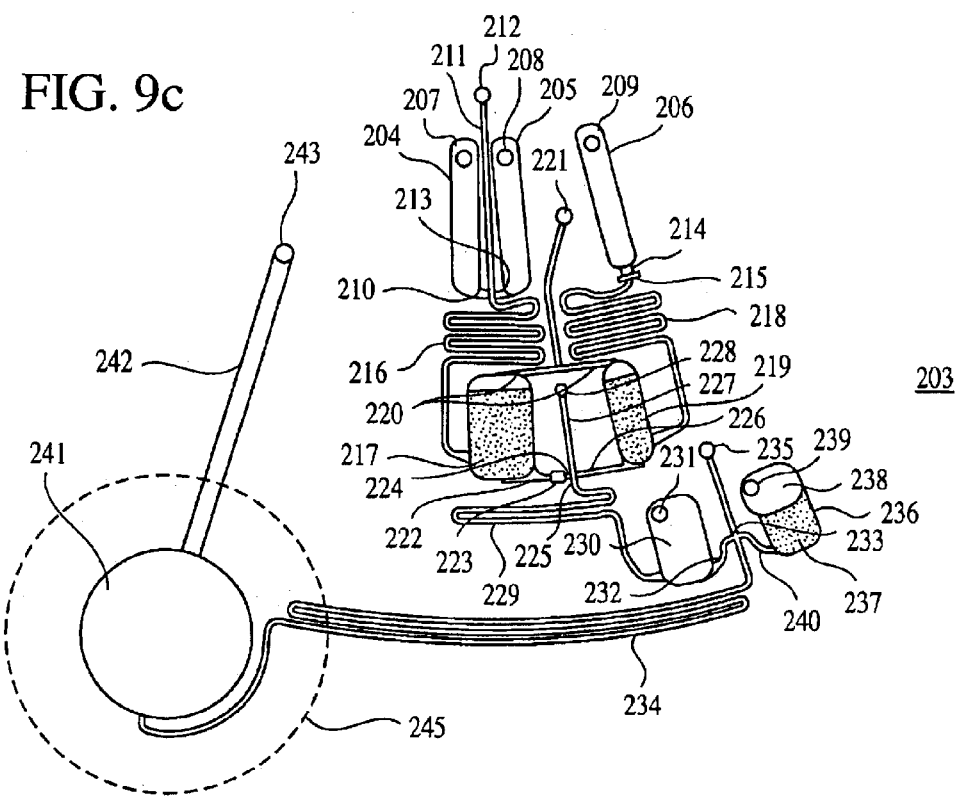

When sufficient time has passed to pump the fluids from reservoirs 204, 205 and 206 and into reservoirs 217 and 219, the rotational rate is decreased further at acceleration $\alpha_4$ to $\omega_4$;, which is shown to be slightly less than 400 rpm, in FIG. 8. This disposition of the fluids on the disc is shown in FIG. 9c. Heat is then applied to reservoir 217, containing the mixture of sample and alkaline cell lysis buffer This heating step, performed at between 85° C. and 95° C. is applied for between 60 and 120s, and is sufficient to disrupt the bacterial cell walls or mammalian cell plasma membranes, thereby releasing DNA into the solution. The alkaline cell lysis solution also has the effect of denaturing proteins, such as hemoglobin found in blood samples that can interfere with the activity of the polymerase enzyme.

Figure 9D:
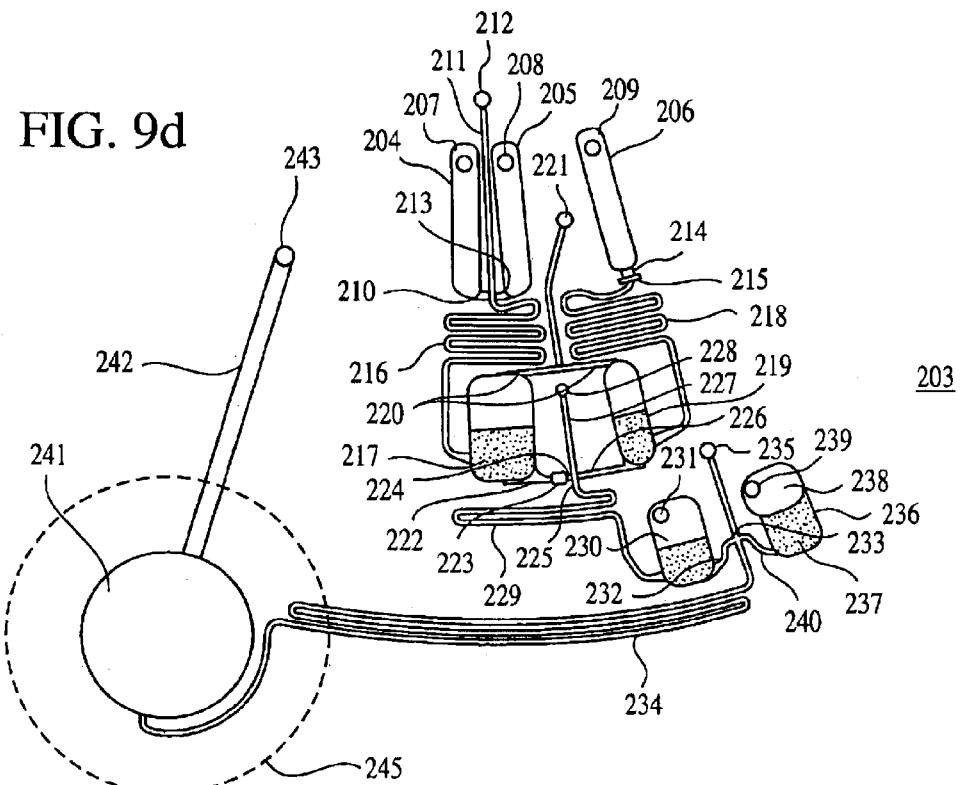
Figure 9E:
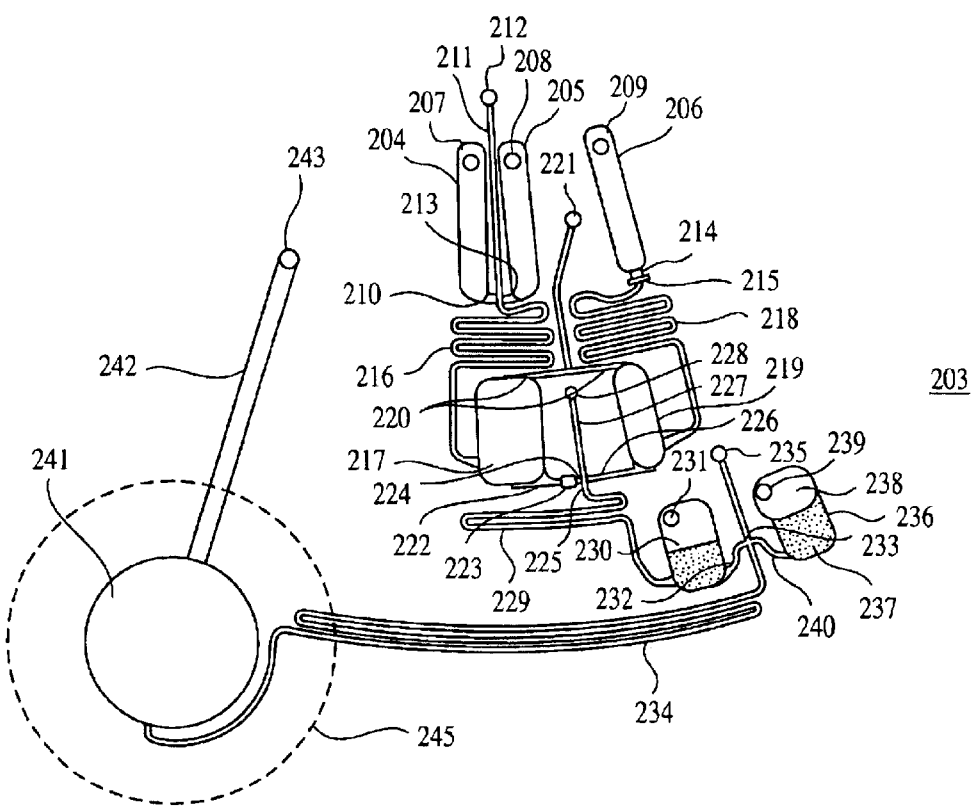

The velocity is then increased at $\alpha_5$ to $\omega_5$ (about 800 rpm) rapidly, as shown in FIG. 8, causing the fluids retained at capillary junctions 223 and 226 to come into contact as capillary pressure is overcome. The microfluidics structures are provided wherein the cross-sectional area of 223 is larger than that of 226, insuring that the lysate is the first to flow. The fluids, once in contact, flow into mixing microchannel 229 and mix, as described above; the velocity is reduced to $\omega_6$ (about 500 rpm in FIG. 8) at acceleration $\alpha_6$ for controlled mixing of the lysate and neutralization fluids. FIG. 9d illustrates the movement of the fluid mixture into reservoir 230; FIG. 9e illustrates the disposition of fluids after they have been pumped.

Figure 9F:
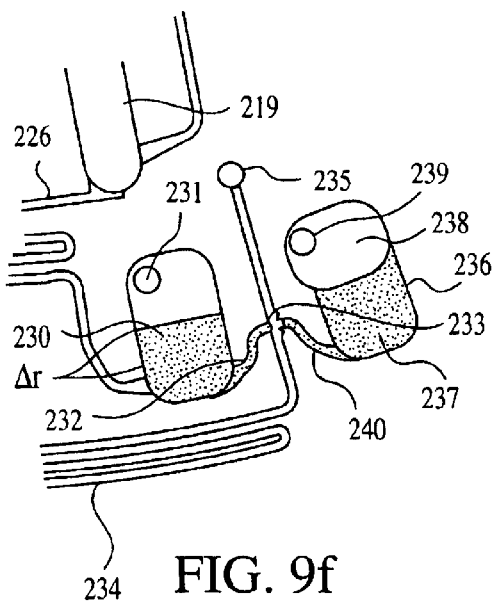
Figure 9G:
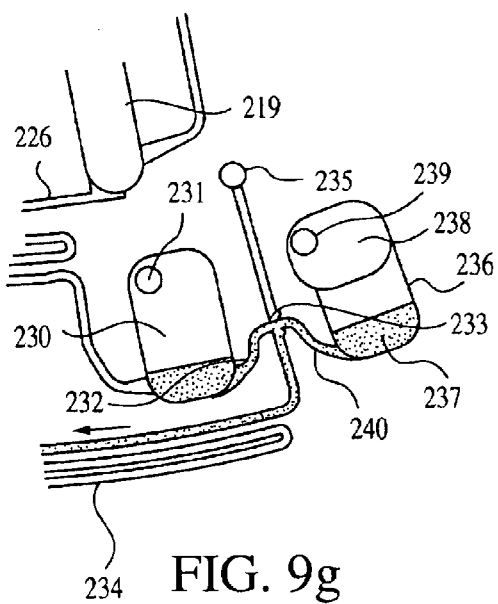

When the mixture of the cell lysate and neutralizing buffer have been transferred into reservoir 230, platform velocity is increased at $\alpha_7$ to velocity $\omega_7$ (about 1200 rpm in FIG. 8). This acceleration is typically gentle compared with other accelerations (as depicted by the more lower slope of the acceleration profile shown in FIG. 8); this is because the design of chambers 230 and 237 and capillary junctions 233 and 240 present a very small "pressure head" as shown in FIG. 9f. The pressure at the capillary junction due to centrifugation is given by $$P = \rho \omega^2 <R> \Delta R$$

where $\rho$ is the fluid density, $\omega$ is the angular velocity $= 2\omega \times$ speed in rpm$\times 60$, $<R>$ is the average position relative to the center of rotation of the fluid, and $\Delta R$ is the extent of the fluid in the radial direction inward of the radial position of the capillary junction. Because the geometry is designed to make $\Delta R$ small relative to a channel emptying radially-outward from the bottom of the reservoir, for example, the pressure at a given rotational rate can be made quite low. This has the advantage of making the rotational rate required to drive the PCR reaction mixture in reservoir 236 beyond the capillary junction with microchannel 233 very high and allows the fluid to be retained even during the rapid accelerations sand decelerations of earlier steps in the velocity profile. In contrast, the exit of microchannel 232 into microchannel 233 flares open and presents at least one smooth edge, to prevent pinning of the advancing meniscus. As a result, fluid is not retained, but moves into microchannel 233 and wets the retained PCR reaction mixture. As the rotational velocity is gradually increased, fluids are pumped into mixing microchannel 234. As shown in FIG. 9g, the configuration of the junction of microchannel 233 and microchannel 240 relative to the fluid position in reservoirs 230 and 236 results in the fluids being drawn into mixing microchannel 234 by, in part, a siphoning action. The neutralized cell lysate and PCR reaction mixture are in contact for sufficient time in the mixing microchannel 234 to effect mixing by diffusion; as shown in FIG. 8, this mixing is performed at relatively high speed (about 1200 rpm).

Figure 9H:
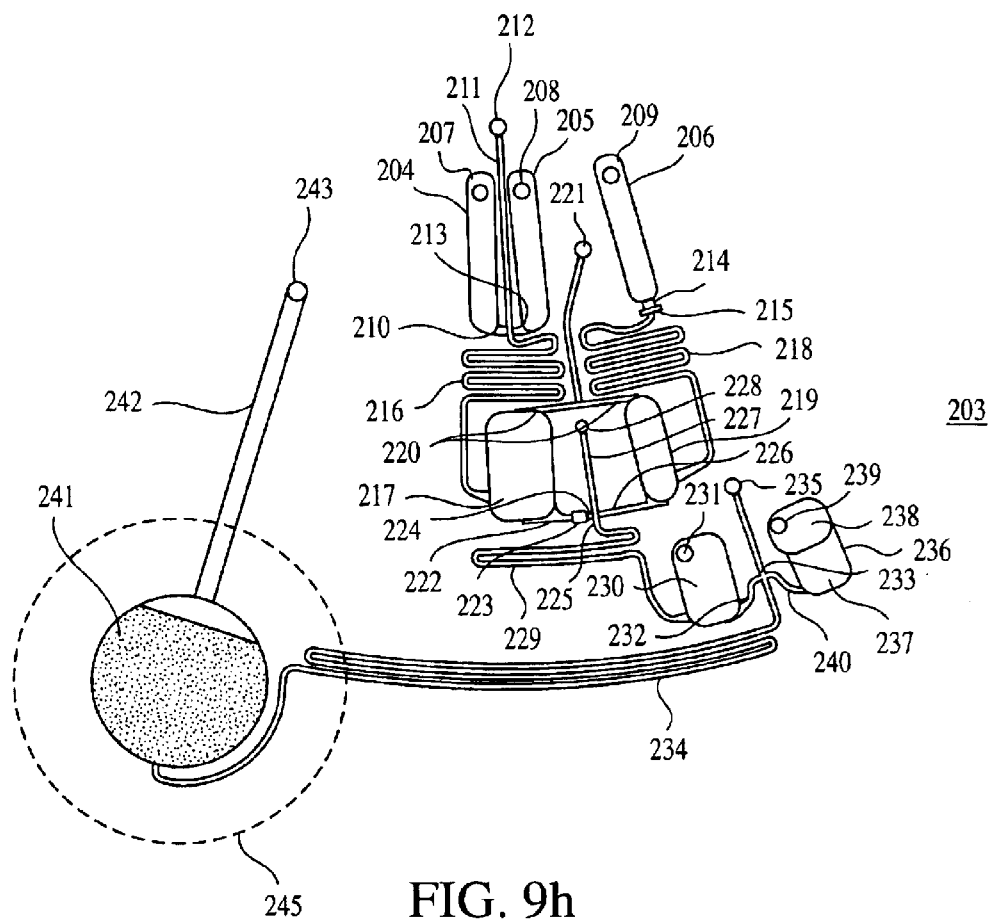

FIG. 9h illustrates the final microfluidics state of the disc, with all fluid having been delivered to thermal cycling chamber 241. The platform speed is reduced to rotational speed $\omega_8$ (about 500 rpm in FIG. 8), in a slow deceleration profile $\alpha_8$ that is similar to the gradual acceleration Thermal cycling is effected in thermal cycling chamber 241 using a variety of thermal cycling protocols and temperature profiles. Examples of such temperature profiles include:

1. Hold the reaction mixture at high temperature (e.g., 95° C.) to denature double-stranded DNA
2. Perform a cycle of step, wherein for n cycles, the following steps are repeated identically n-1 times:
    a) drop the temperature to an annealing temperature (e.g., 45° C.–75° C.), either transiently or for an annealing period to allow annealing of primers to single-stranded DNA;
    b) raise the temperature an extension temperature (e.g., 60° C.–70° C.), either transiently or more preferably with a primer extension period that allows extension of the amplification primers; and
    c) raise the temperature to the denature temperature of the amplified fragment.

Optionally, the final reaction step comprises dropping the mixture to the annealing temperature and then raising the temperature of the thermal cycling chamber to the extension temperature for a time sufficient to substantially complete the extension reactions on all extended products.

The temperature of the sample is then usually reduced to room temperature or below to stop the reaction.
NOW, AS I UNDERSTAND IT THE THERMAL CYCLING CHAMBER IS SIMPLY A BIG RESERVOIR COVERED BY A THERMAL INSULATING LAYER, RIGHT?

The following Examples are intended to further illustrate certain preferred embodiments of the invention and are not limiting in nature.

Example 1

Sample Preparation and PCR of Genomic DNA from *E. coli*

A microfluidics platform as depicted in FIGS. 1 through 4 was used to prepare and amplify a DNA target from samples of *E. coli*. Aspects of the instrument used for controlling the rotational profile and thermal cycling are described in co-owned U.S. Pat. No. 6,063,589, issued May 16, 2000, and co-owned and co-pending patent applications U.S. Ser. Nos. 08/761,063, filed Dec. 5, 1996; 08/768,990, filed Dec. 18, 1996; 08/910,726, filed Aug. 12, 1997; 08/995,056, filed Dec. 19, 1997; 09/315,114, filed May 19, 1999; 09/579,492, filed May 12, 2000 and 09/595,239, filed Jun. 16, 2000 (Attorney Docket No. 95,1408-XX), the disclosures of each of which are explicitly incorporated by reference herein. The instrument used in this example is described above in the Detailed Description of Preferred Embodiments.

The microfluidics structures were manufactured through machining of acrylic using computer/numerical code machining using a Light Machines VMC5000 milling machine running Light Machines "Benchman" software (Light Machines Corporation, Manchester, N.H.). The disc was then vapor polished by exposure to vapor from boiling methylene chloride to remove machine marks and smooth the machined surface. A layer of double-sided tape (such as 7953MP(1.5-0.5-1.5)) was applied to the machined face of the disc. The tape was either die-cut prior to application or the tape was razored out from the openings of the thermal cycling chamber after application. This was done to minimize possible exposure to known inhibitors of PCR in the adhesive of the tape. A layer of Mylar(ISI) was then applied to the double-sided tape, completing the sealing of the fluid structures of the disc. In many cases, the discs were then passivated by exposure to parylene using methods disclosed more fully in co-owned and co-pending U.S. patent application Ser. No. 09/579,492, filed May 12, 2000, incorporated by reference.

The solutions used for sample preparation and PCR were alkaline cell lysis solution, neutralization buffer; and PCR reaction mixture containing oligonucleotide primers for amplifying a specific target sequence.

The E. coli suspension was provided in Luria-Bertani media and had a cell concentration of between $2.7 \times 10^9$ cells/mL and $3.3 \times 10^9$ cells/mL as calculated using absorbance at 600 nm in a standard laboratory spectrophotometer; dilutions of the culture to achieve desired cell numbers were made using Luria-Bertani broth and then diluted 40-fold with deionized water.

The alkaline cell lysis solution used was 10 mM NaOH, and the neutralization buffer was 16 mM Tris-HCl, pH 7.5. The PCR reaction mixture was either the Amersham Pharmacia Ready-to-Go bead or Stratagene Taq 2000. The Ready-to-Go bead was resuspended and brought to a final volume of 25 μL. Both systems give a final concentration of 200 μM of each dNTP and 1.5 mM $MgCl_2$, along with appropriate salts and stabilizers. To this mix were added the primers of interest at a concentration of 20 pmol of each primer in the reaction. These primers were EcoCtl, a primer pair which defines a randomly-selected 300 base-pair (bp) non-coding sequence of the E. coli genome, or lac I, a pair which defines a 422 bp codon for the lac I repressor protein.

EcoCtl-F sequence: 5'-AGTACCGCAAATCGCCAT CAAAAGTAATGC-3' (SEQ ID No.:1);

EcoCtl-R sequence: 5'-GTCAGTTCGCCTTTCAGA GGAATAACCGC-3' (SEQ ID No.:2);

LacI-F sequence: 5'-CCGAGACAGAACTTAAT GGGCCC-3' (SEQ ID No.:3);

LacI-R sequence: 5'-ACAACAACTGGCGGGCAAA CA-3' (SEQ ID No.:4).

All primers were obtained from Research Genetics, Inc., Huntsville, Ala.

The PCR protocol was adapted from Rudbeck & Dissing (1998, *BioTechniques* 25: 588–592). It consists of the following steps: mixing 5 μL of the sample with 5 μL of NaOH; heating the mixture to about 95° C. for 120s to lyse the cells; mixing the lysate with 5 μL of Tris-HCl neutralization buffer; and mixing of neutralized lysate with 10 μL of PCR reaction mixture containing selected primers. This final solution was then subjected to thermal cycling.

Control reactions were performed conventionally on the benchtop by manually carrying out the sample preparation steps above. Thermal cycling was carried out in an M J Research Model PTC-100 with hot bonnet thermal cycler. The cycling parameters for this reaction were as follows:

| Step | E. coli Temperature | Time(min:sec) |
|---|---|---|
| 1: initial acclimation | 25° C. | 00:15 |
| 2: ramp 1 | +70° C. | 1.5° C. per 0:01 |
| 3: initial dehybridization | 95° C. | 2:00 |
| 4: denature | 95° C. | 0:15 |
| 5: ramp 2 | −35° C. | 1.4° C. per 0:01 |
| 6: anneal | 60° C. | 0:15 |
| 7: ramp 3 | +12° C. | 1.2° C. per 0:01 |
| 8: extend | 72° C. | 0:15 |
| 9: ramp 4 | +23° C. | 1.5° C. per 0:01 |
| 10: denature | 95° C. | 0:15 |
| 11: ramp 2 | −35° C. | 1.4° C. per 0:01 |
| 12: anneal | 60° C. | 0:15 |
| 13: ramp 3 | +12° C. | 1.2° C. per 0:01 |
| 14: extend | 72° C. | 0:15 |
| 15: repeat command | Goto step 9 | 33 times |
| 16: final extension | 72° C. | 3:00 |

A similar profile was employed using the platform. The ramp rates or rates of temperature change used were allowed to be "as fast as possible" given the thermoelectric elements used for cycling. The constant temperature times for dehybridization, annealing, and extension were approximately equivalent to those used for the conventionally-performed controls, although it is recognized that the response of the fluid in the disc is slower than that of the temperature sensors embedded in the metal blocks used to interface the disc with the thermoelectric components.

After loading the appropriate volumes into chambers 204, 205, 206 and 236 shown in FIG. 3, the disc was placed on the platen of the instrument, with the center hole of the disc being placed over a threaded screw on the axis of the platen. Thermal grease was used to insure good thermal contact between the disc and the thermoelectric components. A retaining screw was used to hold the disc in place.

The rotational profile used consisted of the following steps:

| Step | starting time (sec) | ending time (sec) | Acceleration (rpm/sec) | speed (rpm) |
|---|---|---|---|---|
| 1. initial acceleration | 0 | 10 | 45 | |
| 2. spin liquids to bottom of chamber | 10 | 20 | 0 | 450 |
| 3. release NaOH and Tris | 20 | 22 | 125 | |
| 4. decelerate to prevent further releases | 22 | 24 | −100 | |
| 5. pump the liquids through to lysis chambers | 24 | 50 | 0 | 500 |
| 6. decelerate for lysis heating | 50 | 52 | −100 | |
| 7. hold for lysis heating | 52 | 140 | 0 | 300 |
| 8. release of lysate and Tris to neutralize sample | 140 | 142 | 250 | |
| 9. decelerate to prevent further releases | 142 | 145 | −100 | |
| 10. pump the liquids through to neutralization | 145 | 160 | 0 | 500 |
| 11. release of neutralized lysate and PCR reagents | 160 | 200 | 25 | |
| 12. pump the liquids through to cycling chamber | 200 | 210 | 0 | 1500 |
| 13. decelerate for thermal cycling | 210 | 245 | −25 | |
| 14. thermal cycling | 245 | 3600 | 0 | 500 |

The thermal cycling profile as described above was then used while the platen and disc rotated at 500 rpm.

Figure 10:
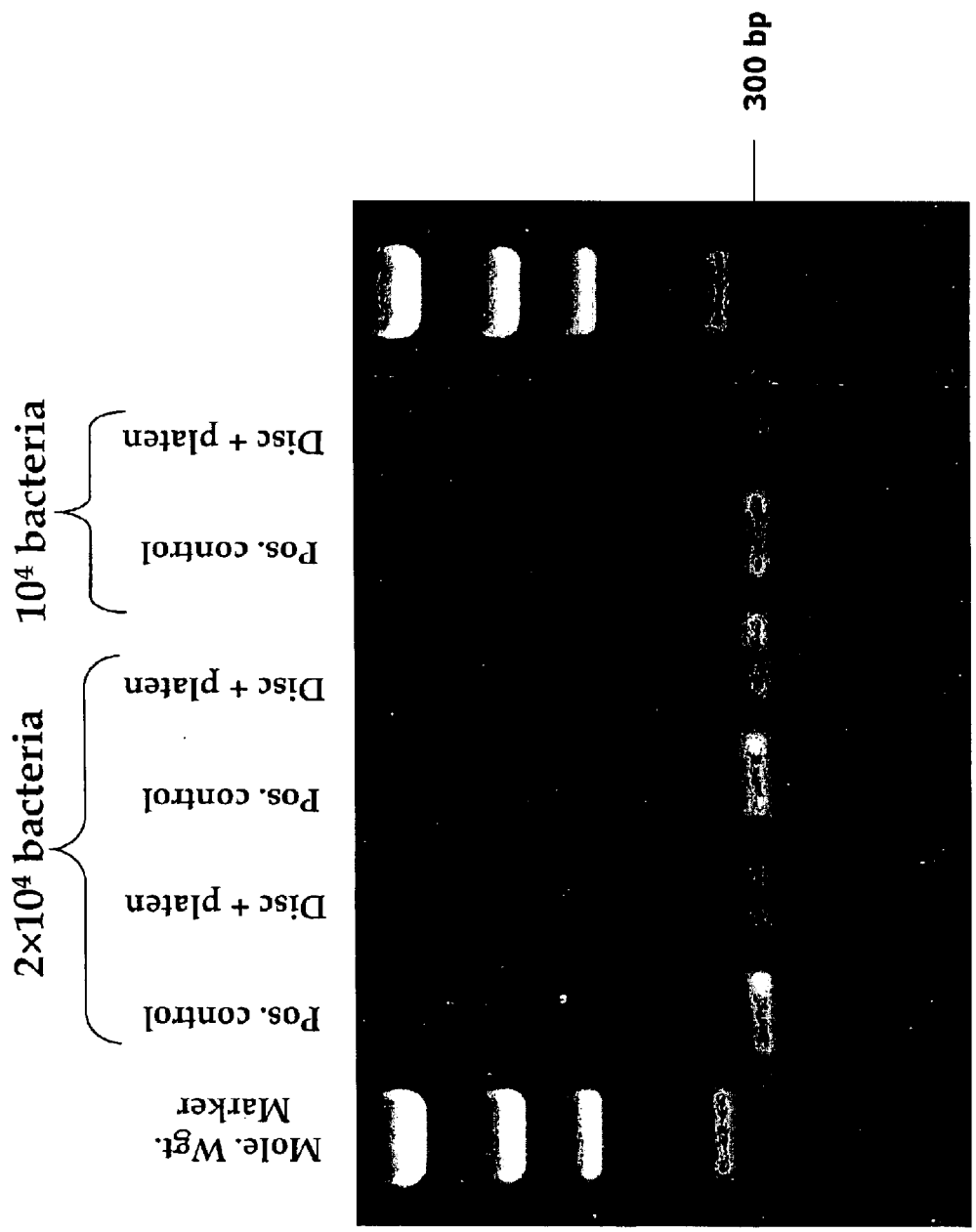
FIG. 10 is a photograph of gel electrophoretic analysis of PCR amplification of a target fragment contained in DNA isolated from $E.\ coli$.

The results of a representative assay are shown in FIG. 10. This Figure depicts a conventional gel electrophoretic analysis (as described in Sambrook et al, 1989, *MOLECULAR CLONING: A LABORATORY MANUAL*, $2^{nd}$ ed., Cold Spring Harbor Laboratory Press: Cold Spring Harbor, N.Y.) of DNA fragments produced by the platforms of the invention compared with a conventional PCR apparatus. These results demonstrate that PCR performance on the platform of the invention produced an amplified target fragment having the correct size as determined by comparison with the conventionally-amplified fragment, and with a yield equivalent to the yield of the fragment amplified using a conventional thermocycling apparatus.

PCR product fragment yields were quantitatively evaluated through the use of an epifluorescence microscope with an illumination source (Nikon, Super high pressure Mercury Lamp Power Supply, Model HB-10101AF). The typical yields are 60–100% of the yields compared to the benchtop method (35–40 ng with 20000 target copies starting material).

In cycling with the above described instrument, volume loss due mostly to evaporation is typically around 20% of the total input volume, so for a 25 μL reaction, typical recovery is approximately 20 μL. This volume loss occurs gradually over the course of the amplification, and the majority of the evaporation condenses in the channel just above the cycling chamber and collects until enough liquid has collected to spin back down into the cycling chamber.

Figure 27:
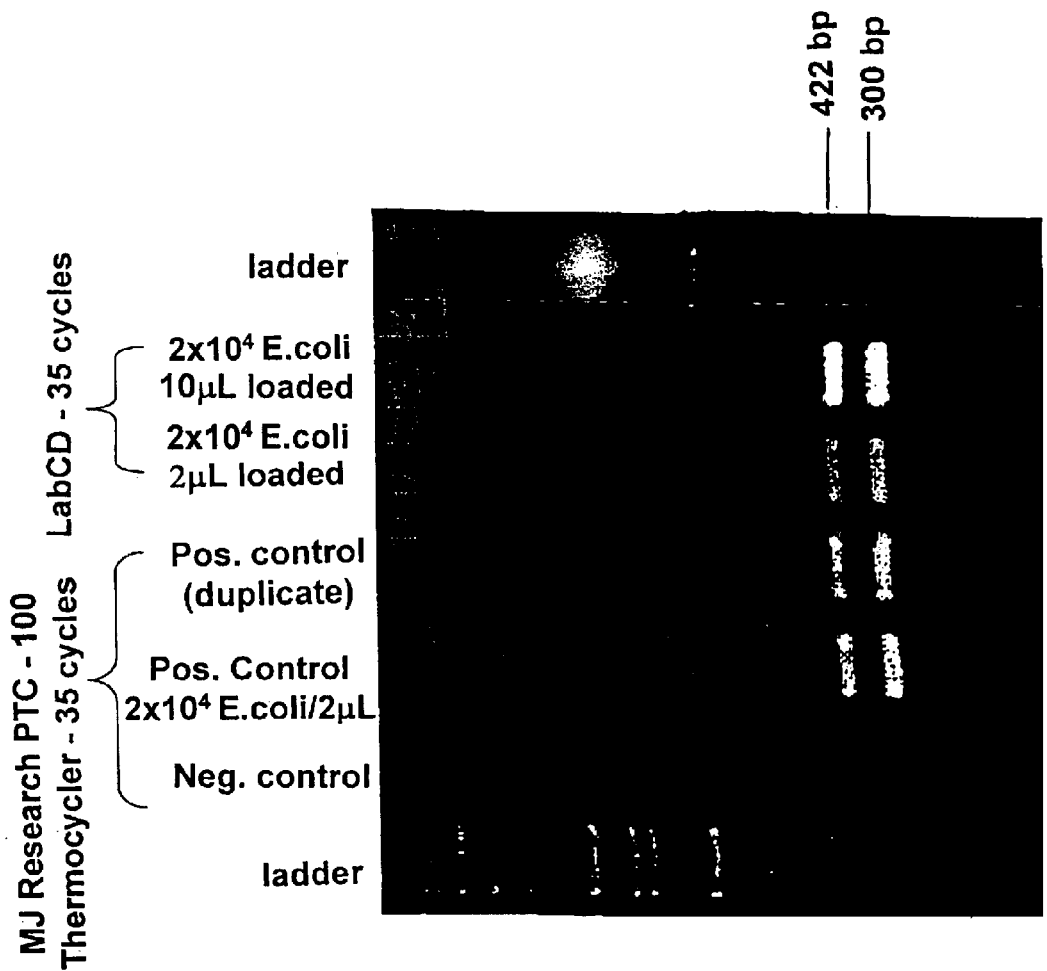
FIG. 27 depicts an example of multiplexed PCR performed in the thermal cycling chamber.

Multiplexing by thermal cycling the sample on the disc was also demonstrated with *E. coli* samples. 20000 cells were lysed and mixed with the PCR reagents on the bench according to the protocol described above. The primers used were the EcoCtl and lacl primers described above. The sample was pipetted directly into the cycling chamber and cycled using the parameters outlined above. The velocity profile was also as above for the cycling portion of the profile: 500 rpm for the duration of the temperature cycling. Typical results for heat-cycled, multiplexed samples can be found in FIG. 27. The PCR product fragment yields were quantitatively evaluated through the use of an epifluorescence microscope with an illumination source as described above. The yield of PCR fragments recovered from the disc was generally about 70% of benchtop yields, and is within the range of yields of the single-amplicon samples.

Example 2

Sample Preparation and PCR of Genomic DNA from Bovine Blood

The experiment set forth in Example 1 was repeated using whole blood samples. In these experiments, heparinized bovine blood was diluted 1:40 in deionized water. While the precise number of white blood cells (WBCs) of the bovine blood was not determined, it is known that the average value is around $5 \times 10^6$ cells/mL.

The alkaline cell lysis solution, neutralization solution, and PCR reagents used were as described above. To the PCR reaction mixture was added the primer pair of interest, those defining the 289 bp codon for M-actin.

β-actin-F sequence: 5'-ACCCACACTGTGCCCATCTA-3' (SEQ ID No.:5)

β-actin-R sequence: 5'-CGGAACCGCTCATTGCC-3' (SEQ ID No.:6).

The general protocol used was similar to that described above. Because white blood cells are less robust than bacteria, the lysis temperature chosen was 91° C.

The rotational profile used is as described in Example 1. The thermal cycling parameters were:

|  | Bovine blood | |
| --- | --- | --- |
| Step | Temperature | Time(min:sec) |
| 1: initial acclimation | 25° C. | 0:15 |
| 2: ramp 1 | +66° C. | 1.5° C. per 0:01 |

-continued

|  | Bovine blood | |
| --- | --- | --- |
| Step | Temperature | Time(min:sec) |
| 3: initial dehybridization | 91° C. | 2:00 |
| 4: denature | 92° C. | 0:30 |
| 5: ramp 2 | −36° C. | 1.5° C. per 0:01 |
| 6: anneal | 56° C. | 0:30 |
| 7: ramp 3 | +13° C. | 1.5° C. per 0:01 |
| 8: extend | 69° C. | 0:30 |
| 9: ramp 4 | +23° C. | 1.5° C. per 0:01 |
| 10: denature | 92° C. | 0:30 |
| 11: ramp 2 | −36° C. | 1.5° C. per 0:01 |
| 12: anneal | 56° C. | 0:30 |
| 13: ramp 3 | +13° C. | 1.5° C. per 0:01 |
| 14: extend | 69° C. | 0:30 |
| 15: repeat command | Go to step 9 | 33 times |
| 16: final extension | 69° C. | 3:00 |

Figure 11:
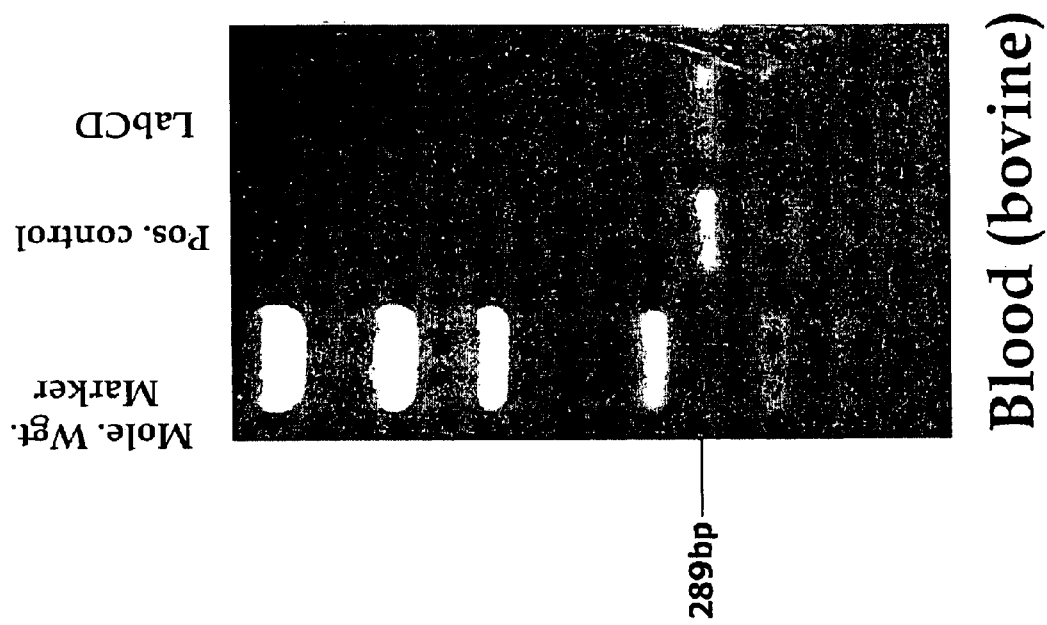
FIG. 11 is a photograph of gel electrophoretic analysis of PCR amplification of a target fragment contained in DNA isolated from bovine blood.
Figure 12:
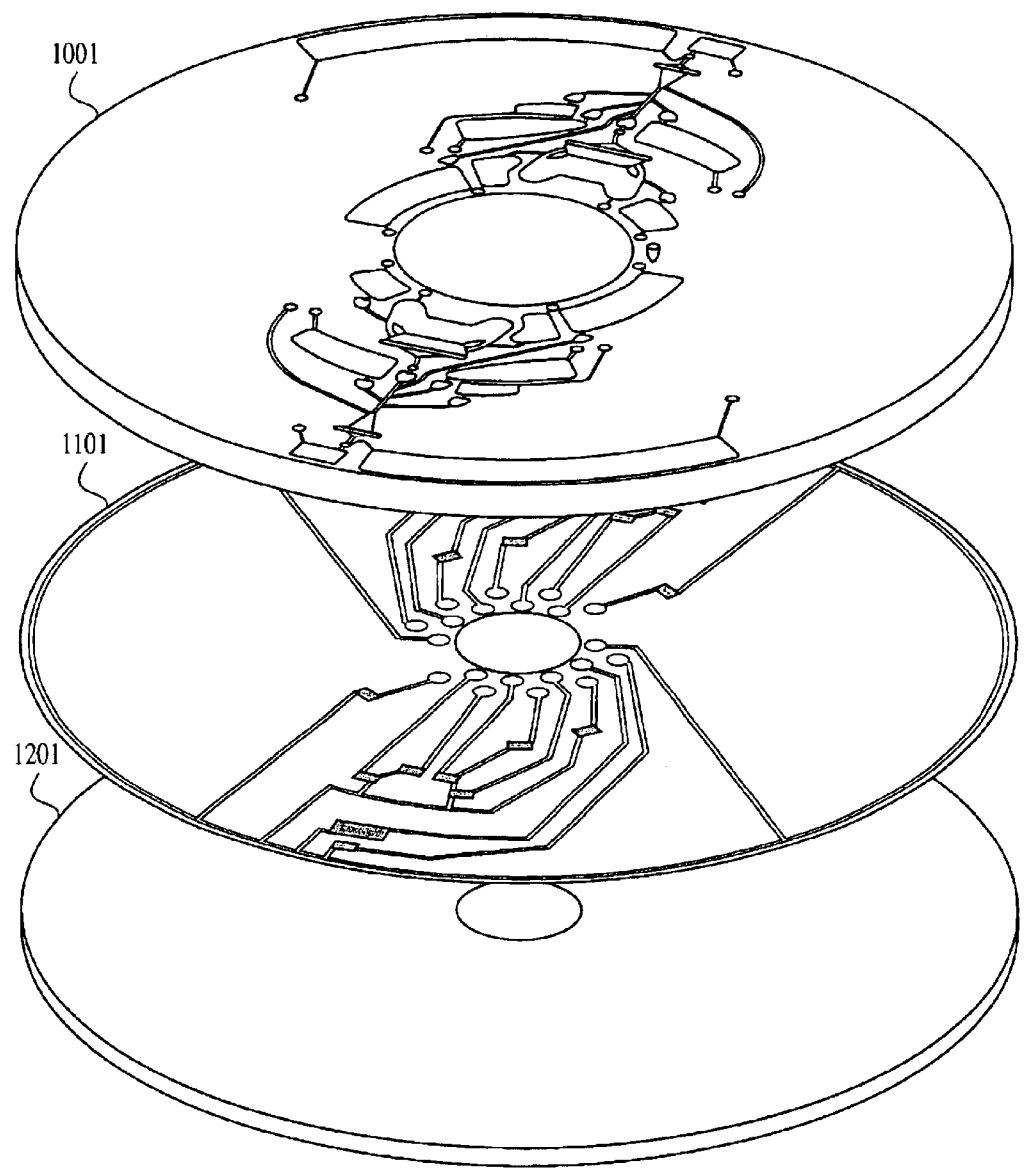
FIG. 12 depicts an exploded, oblique view of the DNA sample preparation disk.
Figure 13:
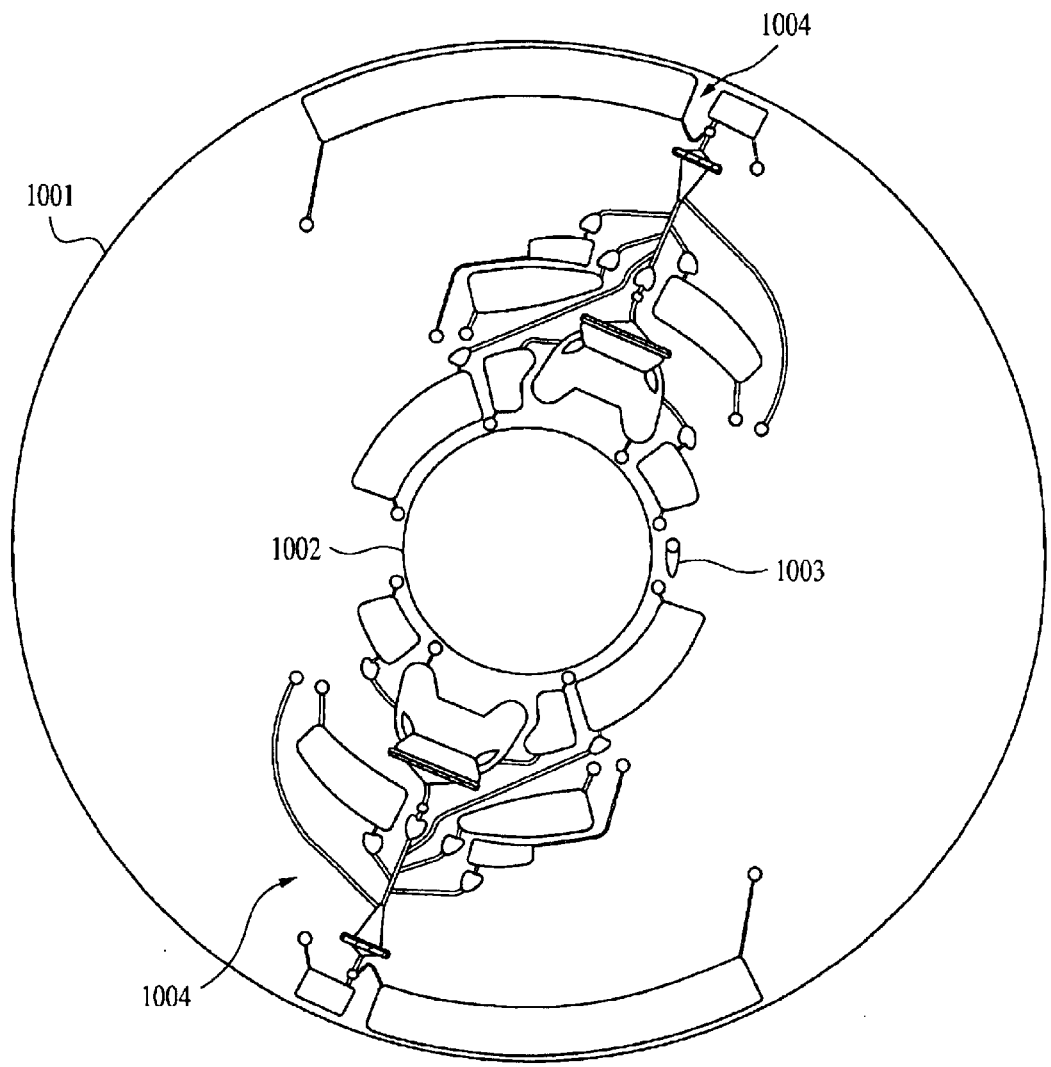
FIG. 13 is a plan view of this disk shown in FIG. 12.

Typical results are shown in FIG. 11, showing the results of conventional gel electrophoretic analysis (as described in Sambrook et al., ibid.). These results demonstrate that PCR performance on the platform of the invention produced an amplified target fragment having the correct size as determined by comparison with the conventionally-amplified fragment, and with a yield equivalent to the yield of the fragment amplified using a conventional thermocycling apparatus.

Example 3

Sample Preparation and PCR of pTrcHis A Plasmid DNA from *E. coli*

The platform shown in FIG. 14 was used for the processing of samples of *E. coli* and the isolation and purification of plasmid DNA. The instrument used for control of the rotational profile and thermal cycling was as described The instrument used for controlling the rotational profile and thermal cycling consisted of a personal computer, interface electronics between the PC and a servo-controlled drive motor and interface electronics between the PC and the screen-printed circuit. For this example, the spindle is driven by a servo-controlled DC motor with encoder (Micromo part #3557K012CR). A serial port converter (J. R. Kerr part #Z232-485) and motor control board (J. R. Kerr, PIC-SERVO) provide a communication interface between the PC and motor. A slip-ring (Litton part #AC6023-24) provided the electrical connection between the rotating platform and the stationary control system.

The microfluidics disc was manufactured through machining of acrylic using computer/numerical code machining as described above. The disc was then vapor polished by exposure to vapor from boiling methylene chloride to remove machine marks and smooth the machined surface.

Paraffin wax valves with a melting point of about 54° C. were inserted by pipetting a small amount of melted wax into the sacrificial valve capillary and quickly pressing the wax flat with a flat edge before it solidified. The excess was wiped away from the edges of the channel, and extra wax on either end of the channel was cut off using an Exacto blade. After the disc was completely assembled (as described below), 5V was applied across each of the leads corresponding to a wax valve, and the wax was allowed to melt and re-crystallize within the channel, allowing the wax to continuously cover the cross-section of the channel.

A piece of Whatman filter paper #54 and piece of frit material (obtained from Porex, #X-4588, having a 70 µm pore size) were cut to the width of the slot at the bottom of chamber 1005. The filter paper and frit material, with the "shiny" side facing toward the filter paper, were inserted into the slot. The frit material was placed on the side of the slot closest to the center of the disc. The orientation of the filter paper was unimportant. The height of the filter paper and frit material were then cut to be equal to the height of the disc.

A piece of glass fiber filter(GF-F obtained from Whatman, ADDRESS) and a piece of frit material, as above, were cut to the width of slot 1029 in binding chamber 1027. The glass fiber filter was placed into the slot, and then the frit material was inserted behind the glass fiber, on the side closest to the edge of the disc, with the shiny side facing the glass fiber filter. The height of both materials was then cut to be equal to the height of the disc.

A fluorinated coating (Cytonix part # ME000) Perfluorocoat was painted into the channels X, Y, Z. The excess perfluorocoat was wiped away from the surrounding areas of the disc, and then a sharp object such as an Exacto blade was run through the channel to ensure that it was not blocked. The disc was then cured at approximately 70° C. for 1 hour to allow the fluorinated coating to set.

A piece of adhesive (3M part #7953MP) was then placed across the entire surface of the disc and carefully sealed around the edges of all of the chambers. A Mylar sheet with silver conductive and carbon resistive inks corresponding to the positions of the wax valves and the binding column was aligned with the disc and adhered with the side containing the ink facing the fluidic structures. Finally, another sheet of the same 3M tape was placed across the back of the Mylar sheet surface and a non-machined acrylic disc (comprising the insulating base layer) was placed against this layer of tape to provide structural integrity to the Mylar layer.

Plasmid DNA was isolated from about 40 µL of a suspension of an *E. coli* bacterial culture that carried the pTrcHis vector containing the CRP insert was acquired from an overnight culture of transfected *E. coli* grown up in Luria Bertani broth; the volume of the suspension used contained between about $1 \times 10^8$ to about $1.5 \times 10^8$ cells in the 40 microliter sample. The reagent solutions used were adapted from a Qiagen MiniPrep kit (QlAprep Miniprep Handbook, Qiagen GmbH, Max-Volmer-Strasse 4, 40724 Hildren, Germany) or made from raw materials. The alkaline cell lysis solution was 200 mM NaOH with 1% sodium dodecyl sulfate (SDS; weight to volume) corresponding to solution P2 in the Miniprep kit. The precipitating solution was 1.0M potassium acetate, pH 5.5 and 3M guanidine hydrochloride, corresponding to solution N3 in the Miniprep kit; this solution adjusts the pH of the lysis mixture and precipitates large genomic DNA fragments, SDS, and proteins; in addition, the chaotropic salt breaks the hydration shell of DNA, allowing it to bind to silaceous materials. The first and second wash solutions were 70% ethanol in water (v/v) and corresponds to PE solution in the Miniprep kit; this solution removed residual salts from the glass fiber matrix. The elution buffer was 0.1×TE (where TE is 10 mM Tris-HCl, pH 8 and 1 mM EDTA) and it eluted bound plasmid DNA from the glass fiber matrix.

The process steps for both benchtop controls and using the platform of the invention were:

(1) mixing sample (about 50 microliters) with alkaline cell lysis solution (about 50 microliters) to effect lysis (2) mixing the resulting solution with the precipitating solution (about 70 microliters)

(3) filtration of the fluid to remove precipitated materials and cell debris (4) addition to the binding matrix (glass fiber filter)

(5) two sequential washes of ethanol/water solution (70% v/v) (using about 100 microliters for the first wash and about 150 microliters for the second wash step)

(6) elution of plasmid DNA using about 40 microliters of 0.1×TE solution.

Steps (1)–(6) are modified from the Qiagen Miniprep protocol; the only alterations from the published protocol are in ratios of volumes of the solutions. The volumes listed above were used both for the bench controls and on the disc. The materials and procedures for the bench controls are as in the Miniprep kit; the discs of the invention were run after loading fluids through the following steps:

1) accelerate to 1000 RPM. Alkaline cell lysis solution flowed from reservoir 1016 into mixing chamber 1005 (shown in FIGS. 17*a–c*; the arrow marked ω shows the rotational direction (arbitrarily chosen to be counter-clockwise)).

Figure 17A:
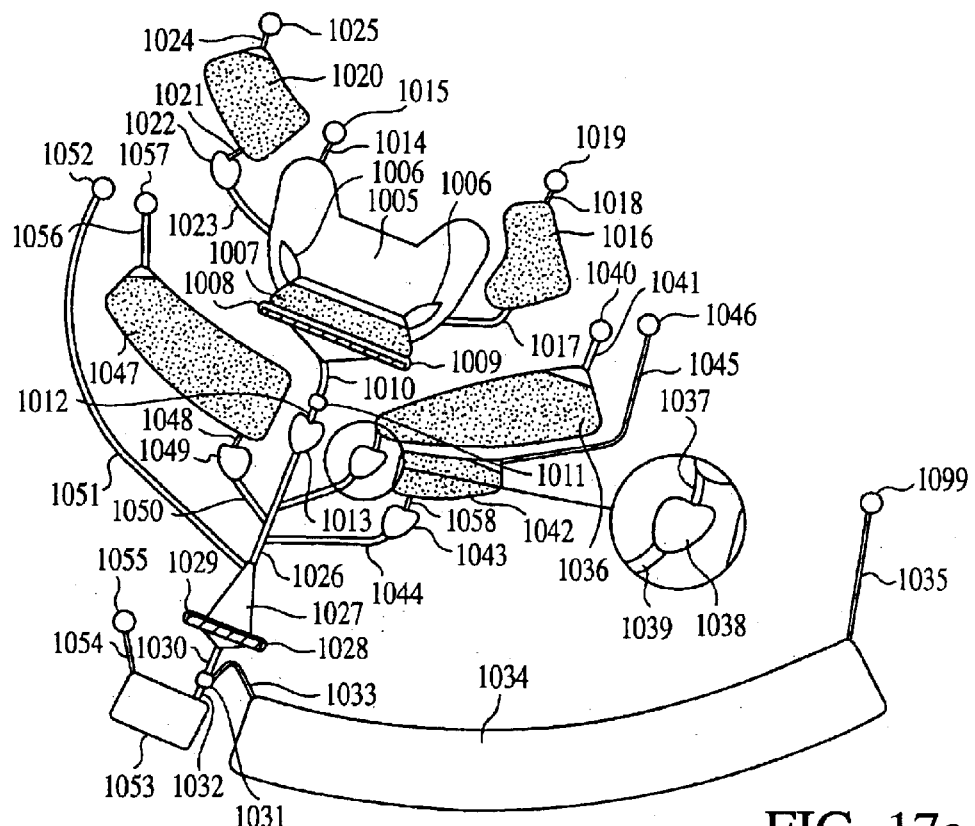
FIGS. 17A through 17K illustrates fluid movement through the microfluidics structure for a plasmid DNA preparation platform.
Figure 17B:
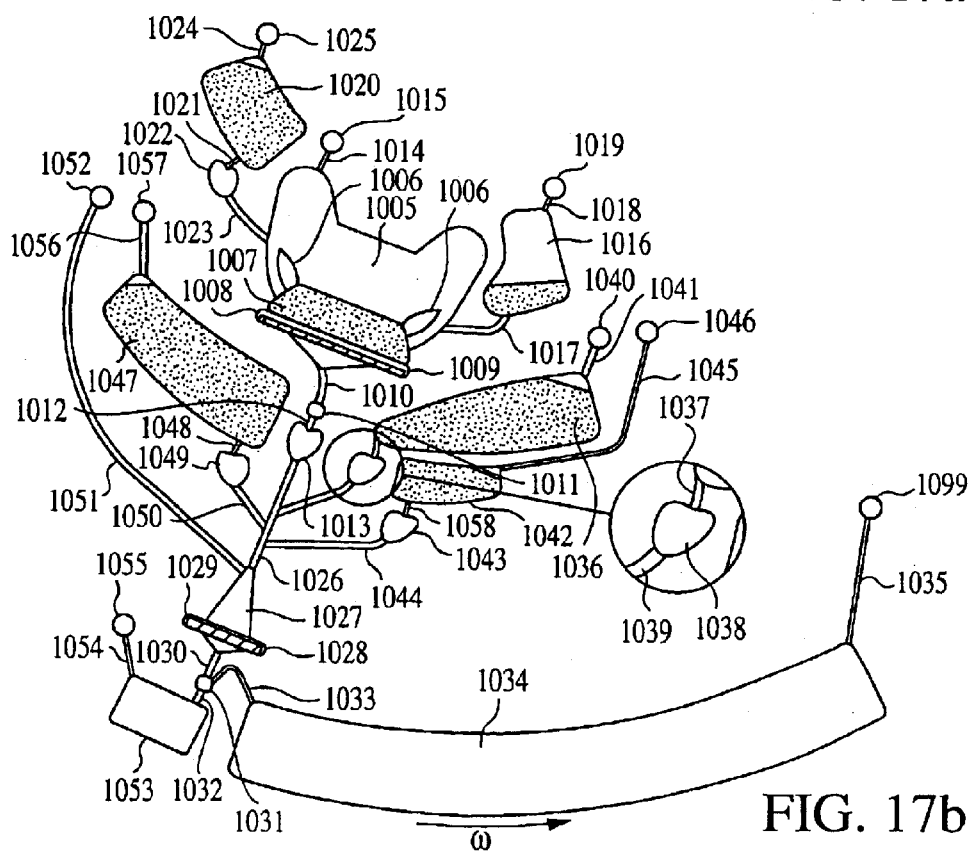
Figure 17C:
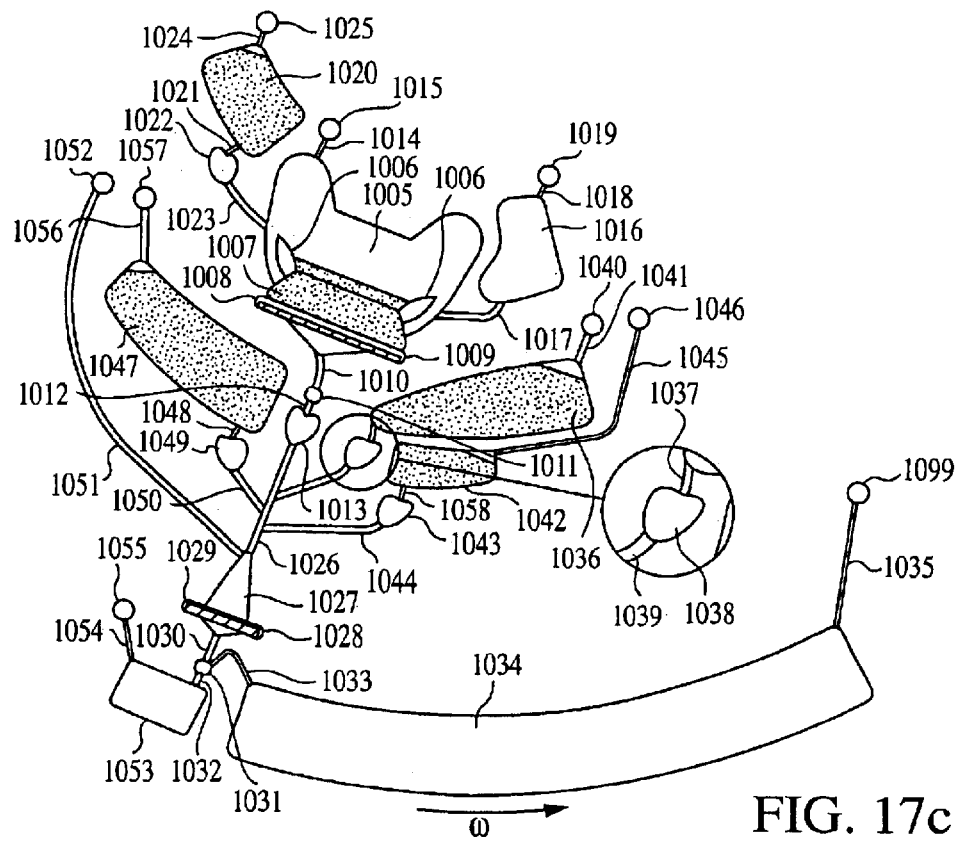
Figure 17D:
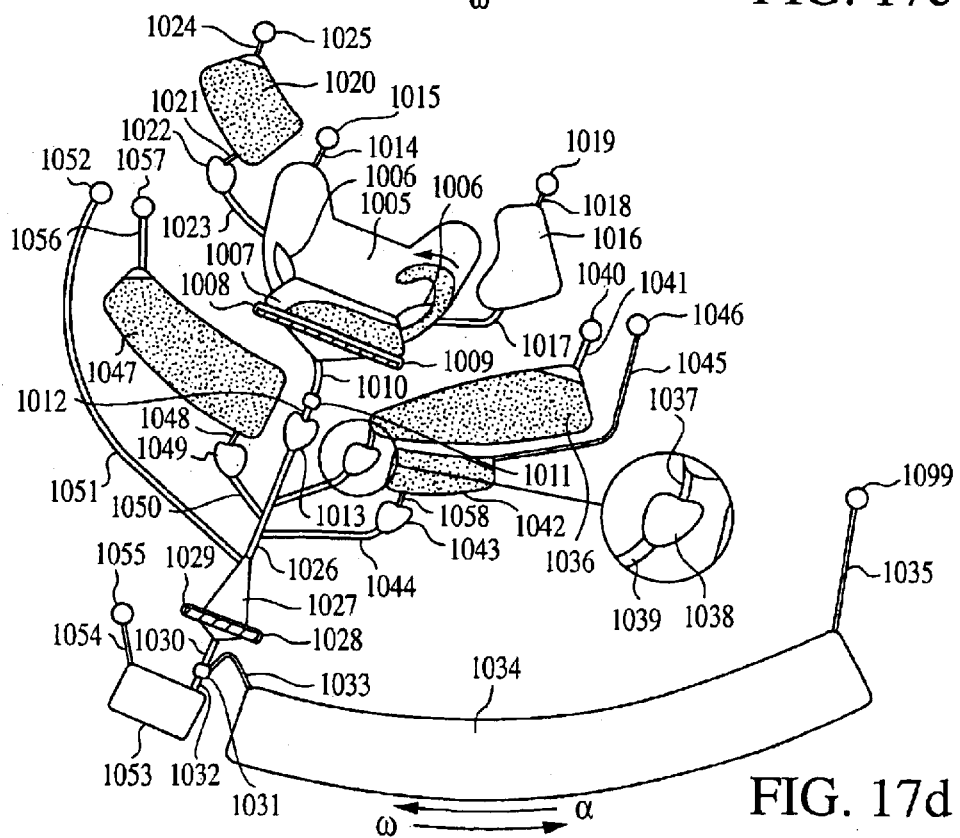
Figure 17E:
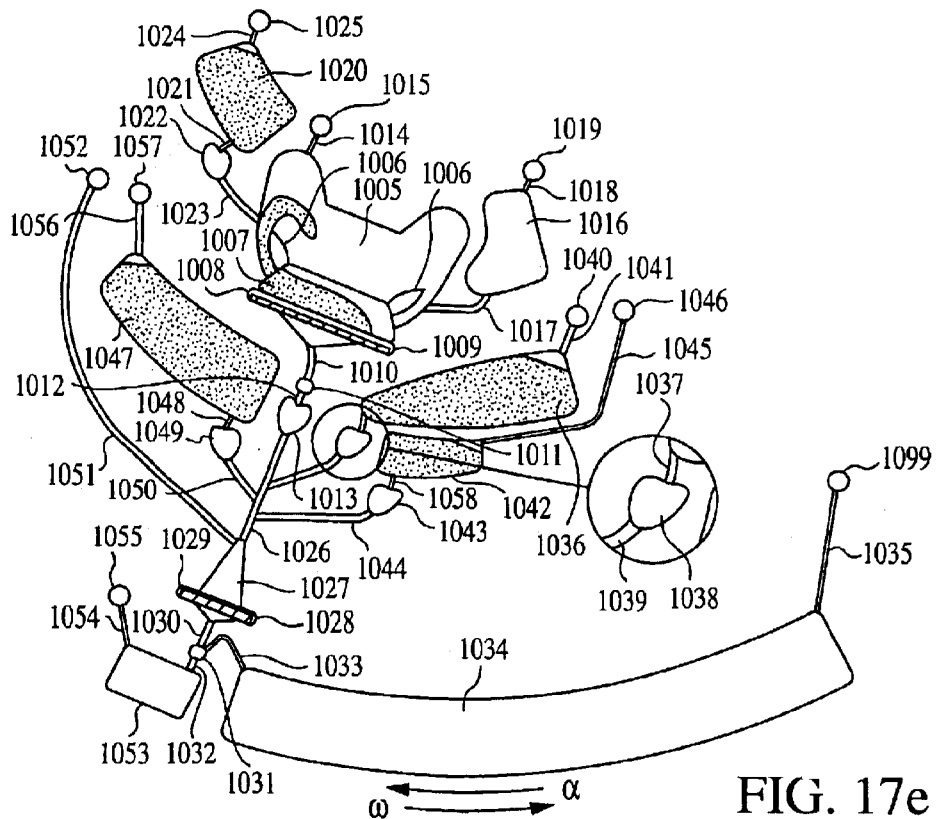

2) agitate 5 times, using complete stops and accelerations of 500 rpm/s, to mix the solution and the sample (shown in FIGS. 17*d–e*).

3) accelerate to 1000 RPM.

Figure 17F:
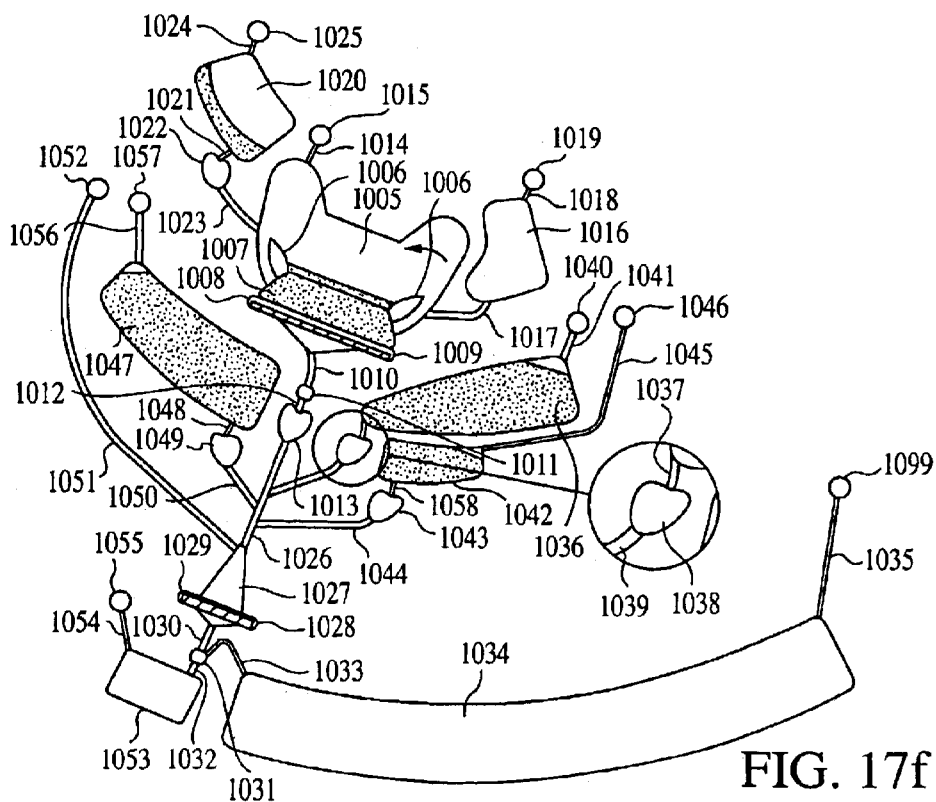

4) apply voltage to leads corresponding to sacrificial valve at 1021. Precipitating solution driven into 1005 (FIG. 17*f*).

5) mix as above in step (2)

Figure 17G:
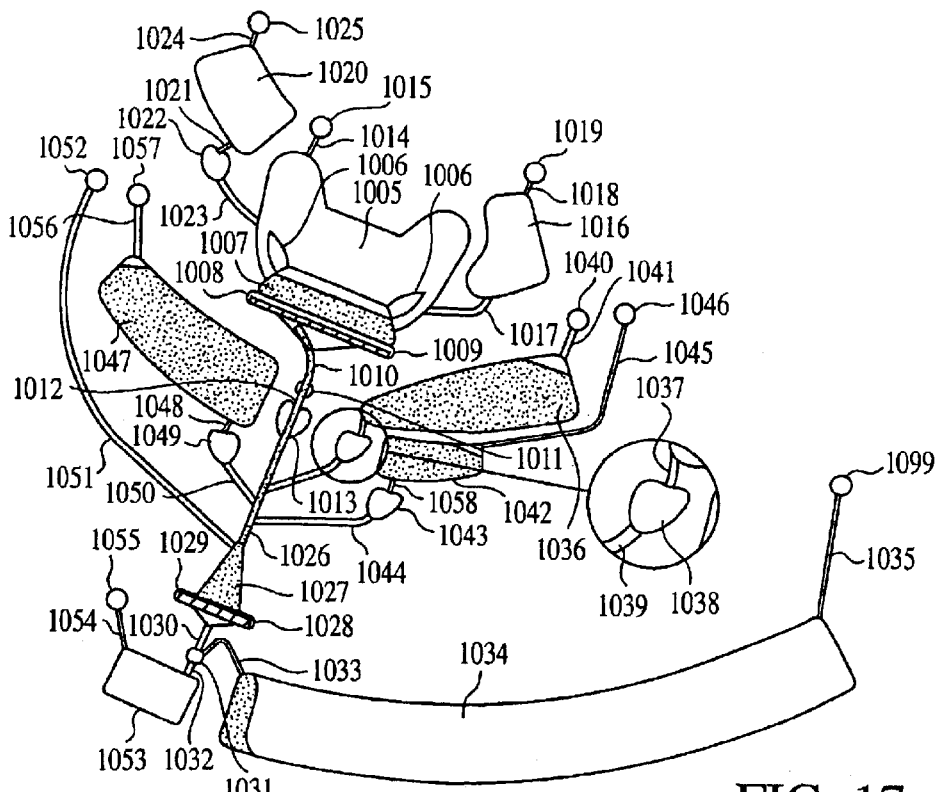
Figure 17H:
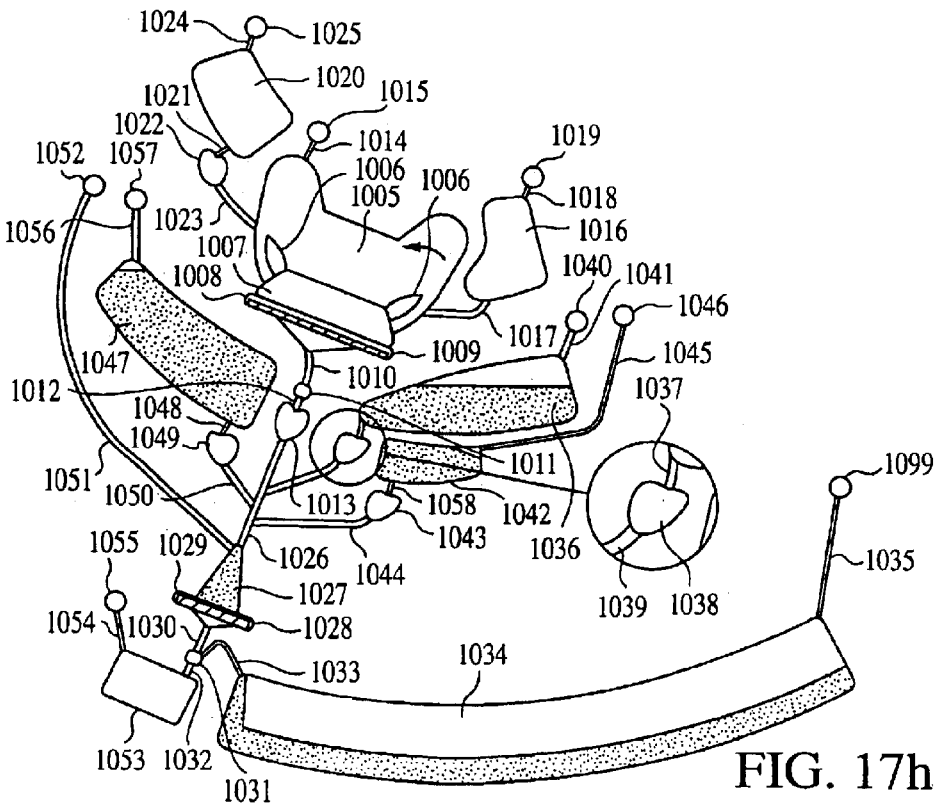
Figure 17I:
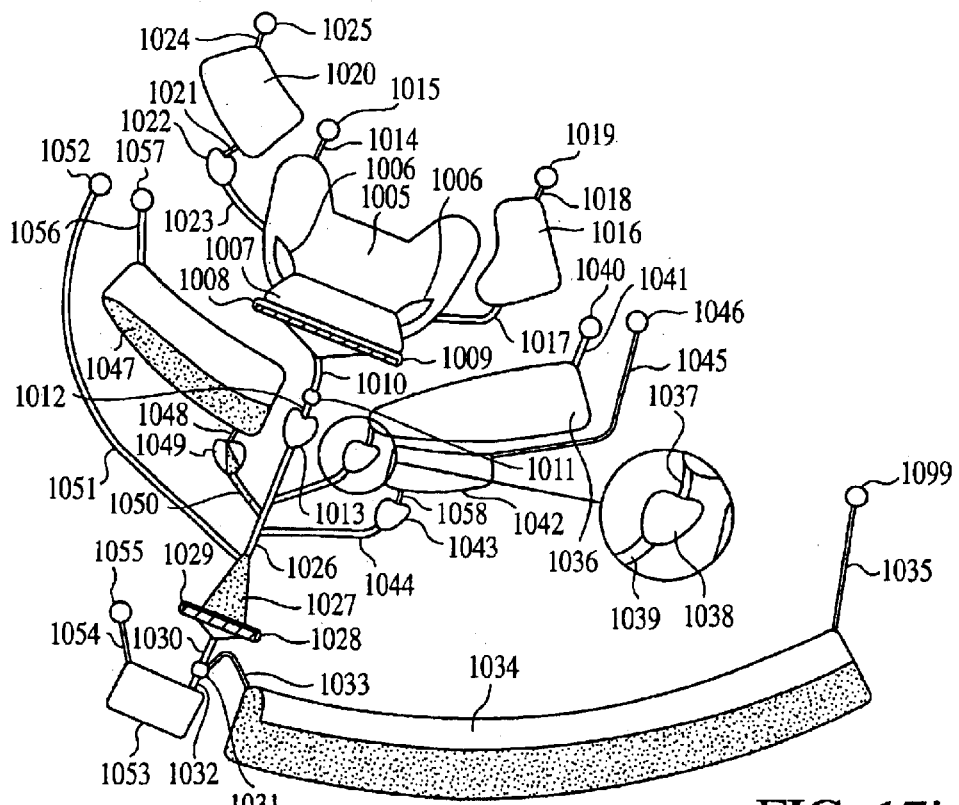
Figure 17J:
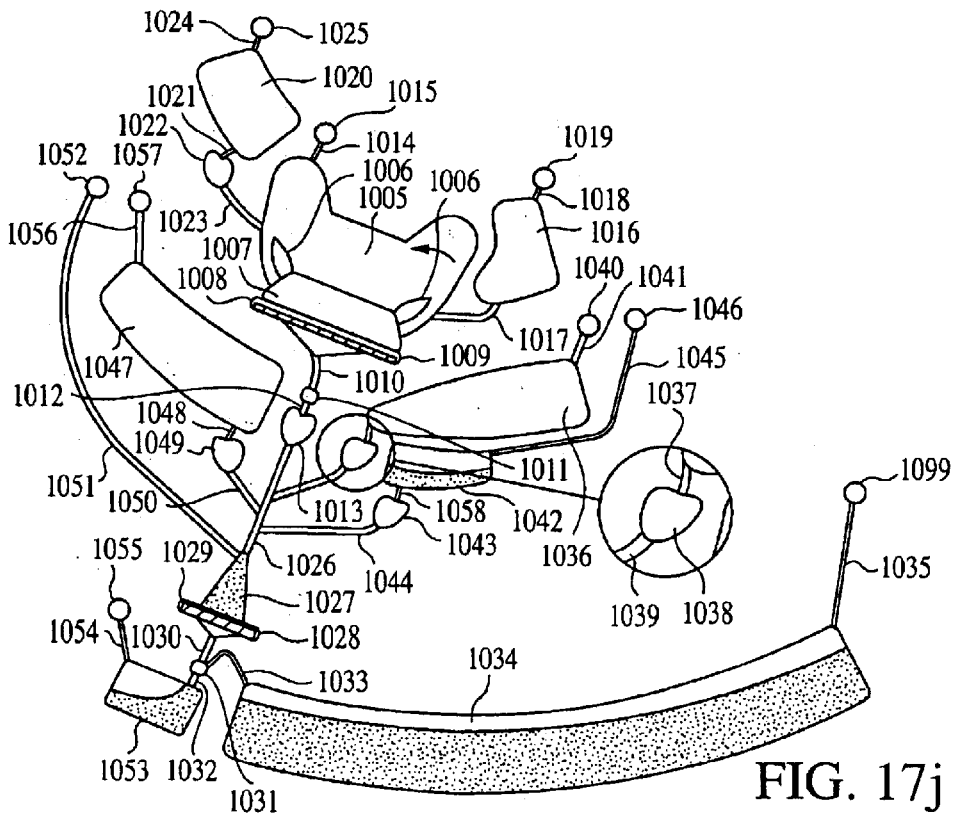
Figure 17K:
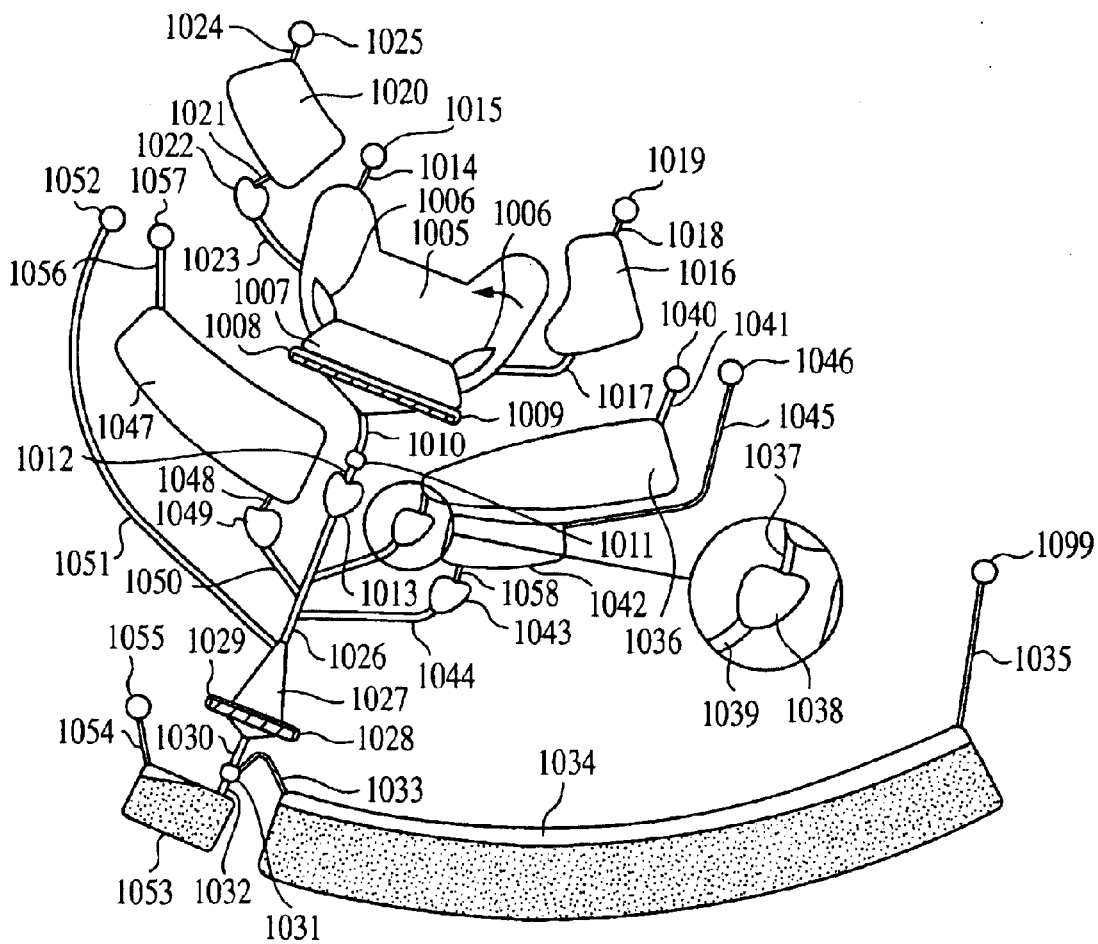

6) accelerate to 1000 RPM. Apply voltage to leads corresponding to sacrificial valve at 1012. Solution released from 1005 onto binding column 1027 (FIG. 17*g*). Maintain at 1000 RPM for a time sufficient to completely move the precipitated mixture through the glass filter and into waste chamber 1034.

7) apply voltage to leads corresponding to sacrificial valve at 1037, releasing first wash solution. Maintain rotational speed at 1000 RPM until first wash solution passed completely through glass fiber into waste chamber 1034 (shown in FIG. 17*g*)

8) apply voltage to leads corresponding to sacrificial valve 1048, releasing second wash solution. Maintain at 1000 RPM until second wash solution completely passed through glass fiber into waste chamber 1034. (shown in FIG. 17*h*)

9) apply voltage to leads corresponding to sacrificial valve at 1032, opening the sample collection chamber.

10) 5 seconds later, apply voltage to leads corresponding to sacrificial valve 1058, releasing elution buffer.

11) Maintain platform rotation at 1000 rpm until all elution buffer washed through glass fiber filter into sample collection chamber. Maintain rotational speed for at least an additional minute after no additional elution buffer appears to be flowing through microchannel 1032. (shown in FIGS. 17*j–k*).

12) Remove fluid sample from platform using port 1055.

For both bench controls and samples run on the discs of the invention, the recovered fluid was dried in a Speedvac (Savant CorporationDrying serves to reduce the volume of liquid (and increase the concentration) to be analyzed; it also removes residual ethanol. The dried sample was then resuspended in 10 microliters of deionized water. In some cases a restriction enzyme such as AlwN1 (New England Biolabs, Beverley, Mass.), a 9-base cutter, was used to digest the sample. This enzyme is sensitive to residual salt and as a result serves as a test of sample cleanliness. In all cases, either all or some of the undigested sample was resolved using ethidium bromide gel electrophoresis on a 1% agarose gel in 1×TBE buffer. The resulting bands when compared to a size ladder, are indicative of the size of the plasmid DNA in the sample. The larger genomic DNA, if contaminating the sample, would be visible in the wells of the gel. For digested samples, complete cutting of the sample, with no residual uncut band, indicates the cleanliness of the sample.

Figure 18:
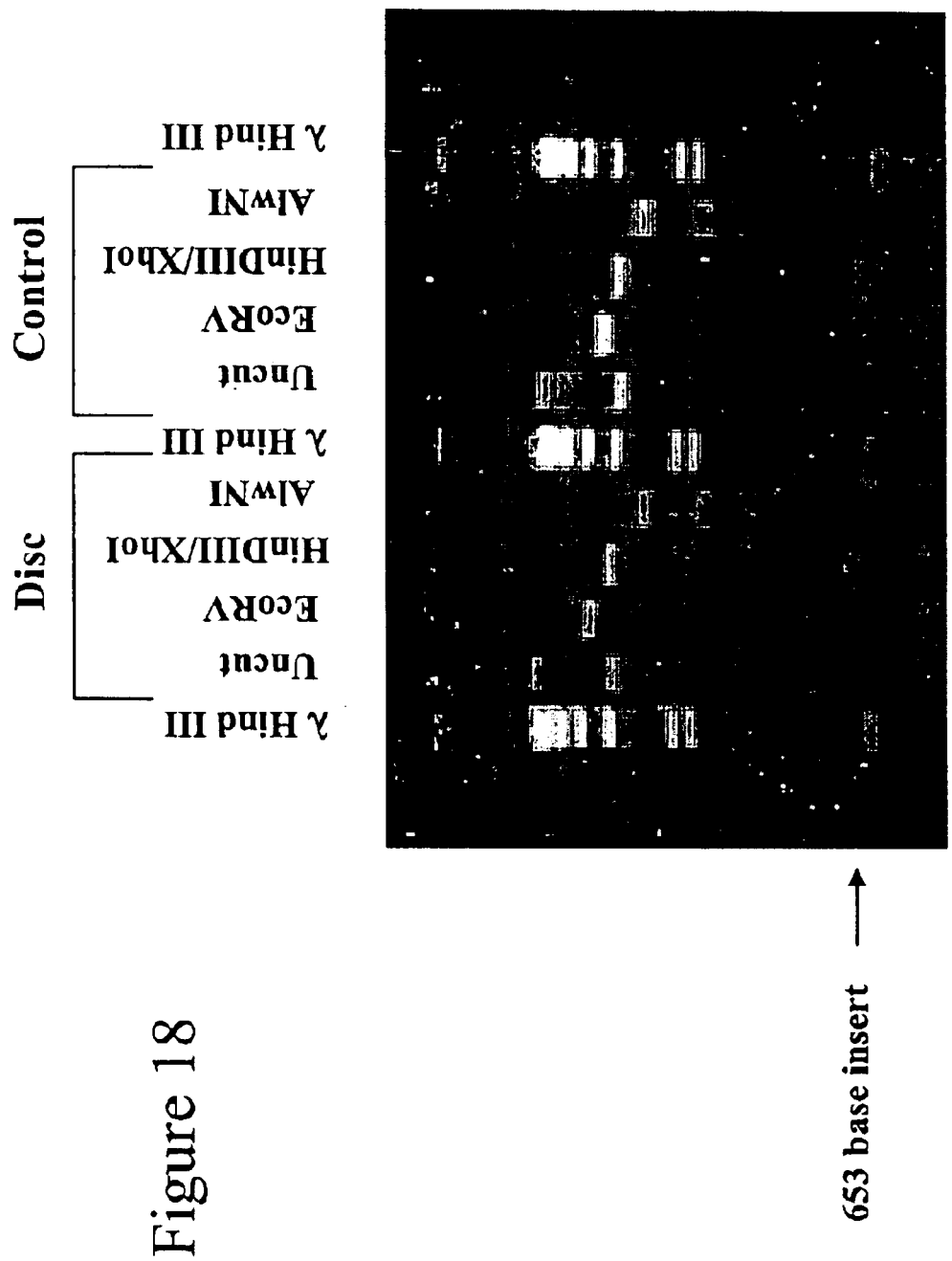
FIG. 18 is a photograph of gel electrophoretic analysis of a restriction enzyme digestion profile of plasmid DNA prepared conventionally (control) or using a plasmid DNA preparation platform of the invention, wherein the outside lanes are size markers.

FIG. 18 shows a gel that illustrates the purity of the sample by using several different restriction enzymes. First, the uncut sample run alone on the gel shows the plasmid in several different conformers with very little salt in the sample itself. The plasmid was cut with EcoRV enzyme, which linearizes the plasmid and causes all of the conformers to run at one size against the ladder. This demonstrates that all the conformers can be cut. The second digestion was a double digestion using both the XhoI and HindIII sites. These sites fall to either side of the CRP insert and results in two long fragments and the 653 base insert fragment. The final as digest was AlwN 1. This is a nine-base cutter and is highly sensitive to salt contamination in the product. The results of these assays demonstrates that plasmid DNA obtained using the platforms of the invention is comparable in quality and purity to plasmid DNA isolated using conventional benchtop methods.

Figure 19:
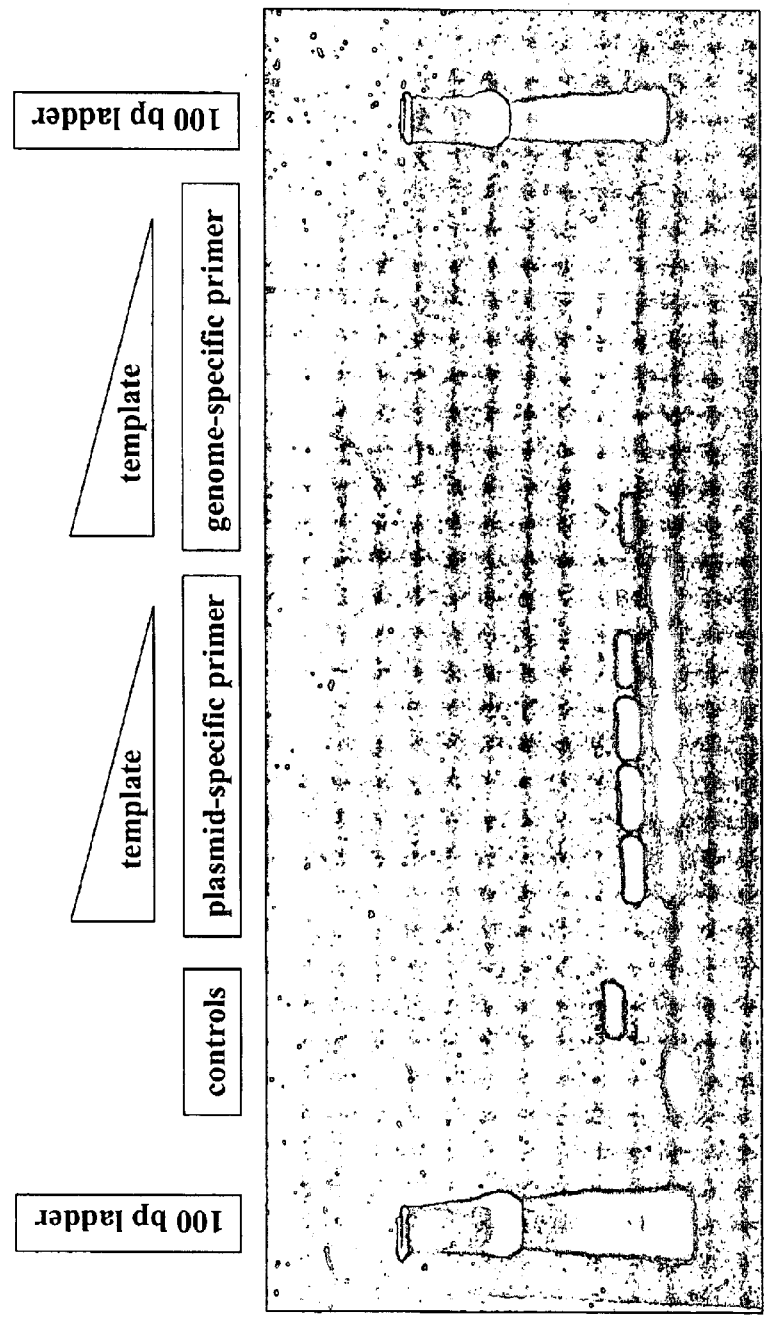
FIG. 19 is a photograph of gel electrophoretic analysis of an in vitro amplification reaction using primers specific for plasmid DNA or bacterial genomic DNA, wherein the amount of template DNA decreases in each set of amplification reactions moving from left to right, using a plasmid DNA preparation platform of the invention; the outside lanes are size markers.

FIG. 19 shows the results of an assay for genomic DNA contamination. PCR is performed using plasmid-specific primers as well as primers specific to a fragment of the *E. coli* genomic DNA. The negative and positive controls used genomic DNA and genomic primers. The first amplification series show the expected amplified fragment at decreasing amounts of plasmid template DNA using plasmid-specific primers. The second amplification series show amplification (or lack thereof) of a genomic DNA fragment using genomic DNA primers and plasmid DNA template.

As can be seen, successive 10-fold dilutions yield significant PCR product using plasmid-specific primers through 1:1000 dilution; only at 1:10000 dilution was little amplification obtained. By contract, genomic DNA-specific primer shows amplification only for the neat sample and 1:10 dilution. These observations indicate an approximately 1000-fold excess of plasmid to genomic DNA.

Example 4

PCR of Genomic DNA from *E coli*

A microfluidics platform as depicted in FIGS. 6, 7, 24, 25 and 26 was used to amplify a DNA target from samples of *E. coli*.

Figure 6:
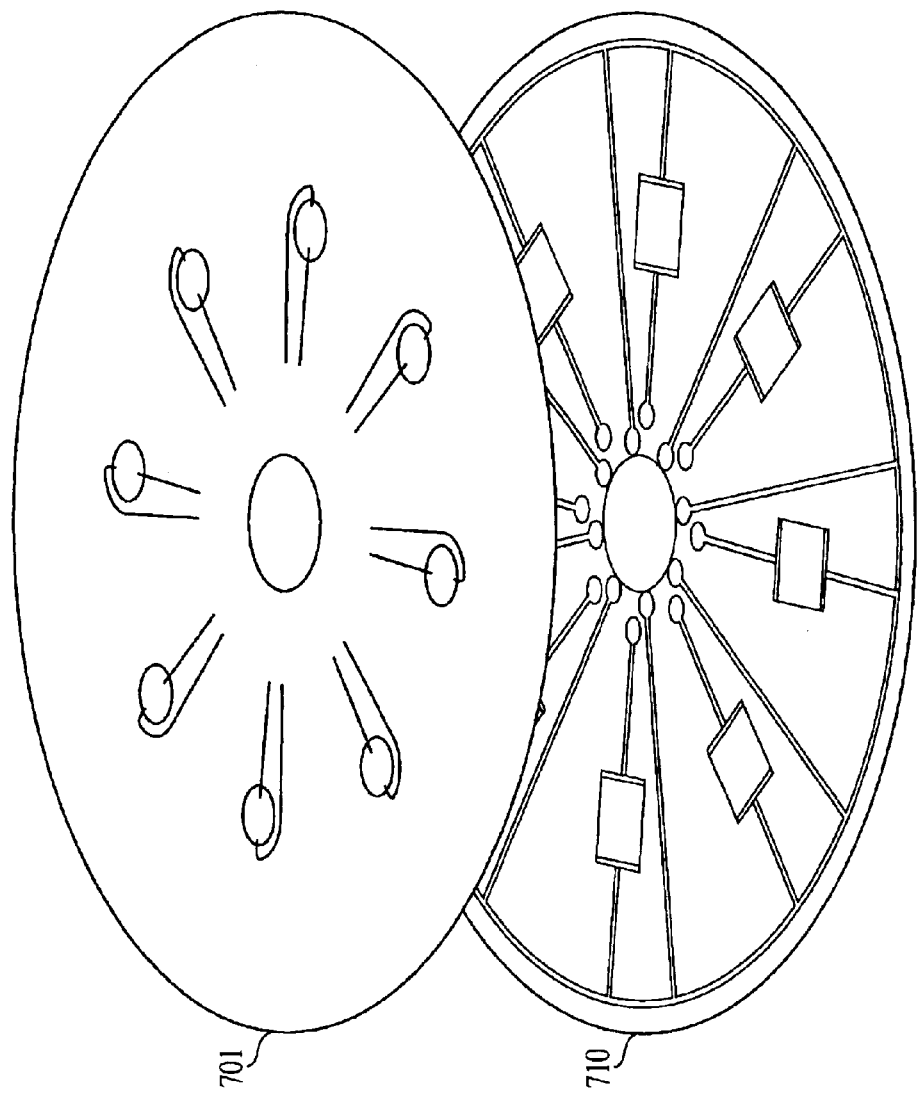
FIG. 6 depicts an explode, oblique view of a microfluidics disc and a printed circuit.

FIG. 6 gives an exploded view of the two main components of the microfluidics platform. A machined fluidics disk 701 is bonded to a screen printed electrical circuit disk 710.

Figure 7:
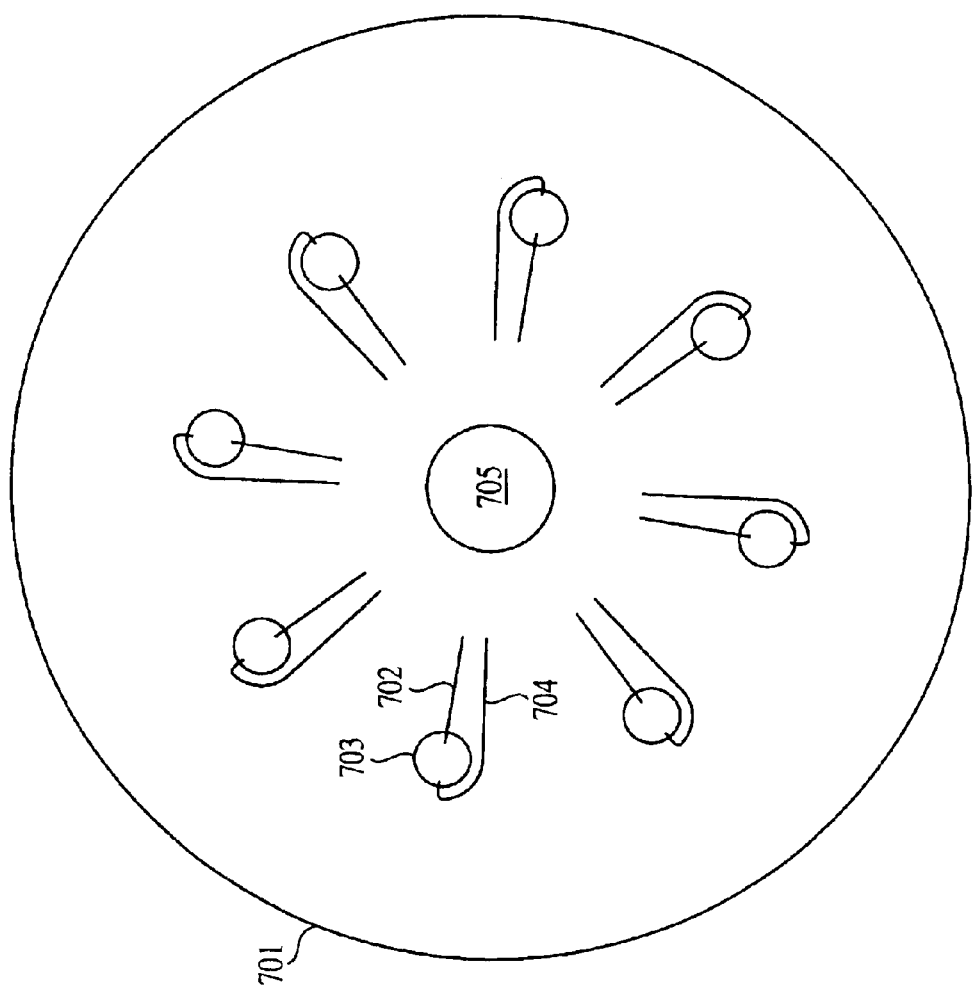
FIG. 7 illustrates a plan view of the microfluidics disc shown in FIG. 6.

FIG. 7 shows an array of eight cycling chambers 703 within the fluidics disk. The thermal cycling chambers are circular with a diameter of 7 mm and depth of 0.5 mm. Each chamber has a reaction mixture loading channel 704 and an air channel 702. Both channels are 0.5 mm wide by 0.5 mm deep. The air channel helps to prevent liquid loss upon heating, as vapors cool and condense along its walls before spinning back down to the reaction chamber.

Figure 24:
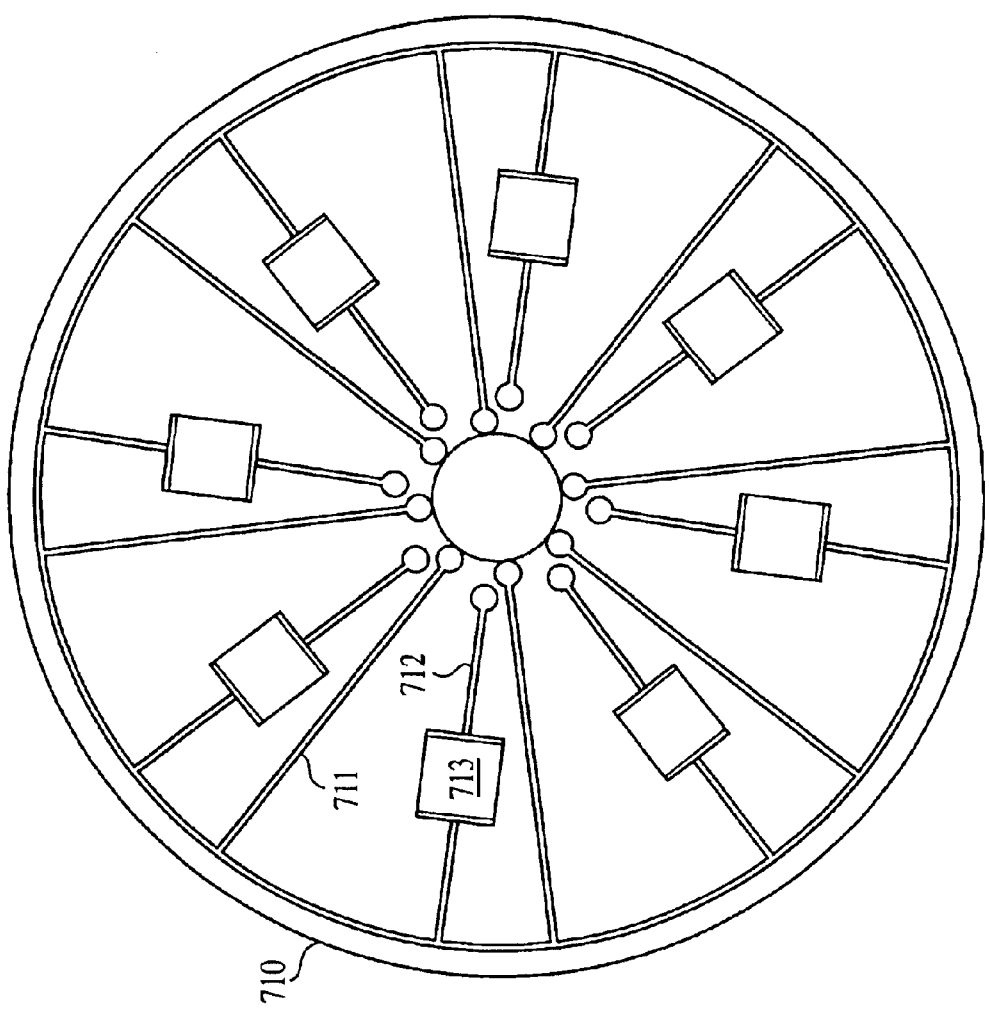
FIG. 24 depicts a plan view of the electric circuit layer shown in FIG. 6.

FIG. 24 shows how resistive heaters are arrayed on the electrical circuit disk. The resistive heater patches 713 are squares, 10 mm on a side. The heater dimensions were chosen to be larger than the cycling chamber dimension to minimize thermal gradients across the cycling chamber. Electrical current is supplied to the heaters through positive 712 and ground 711 leads.

Figure 25:
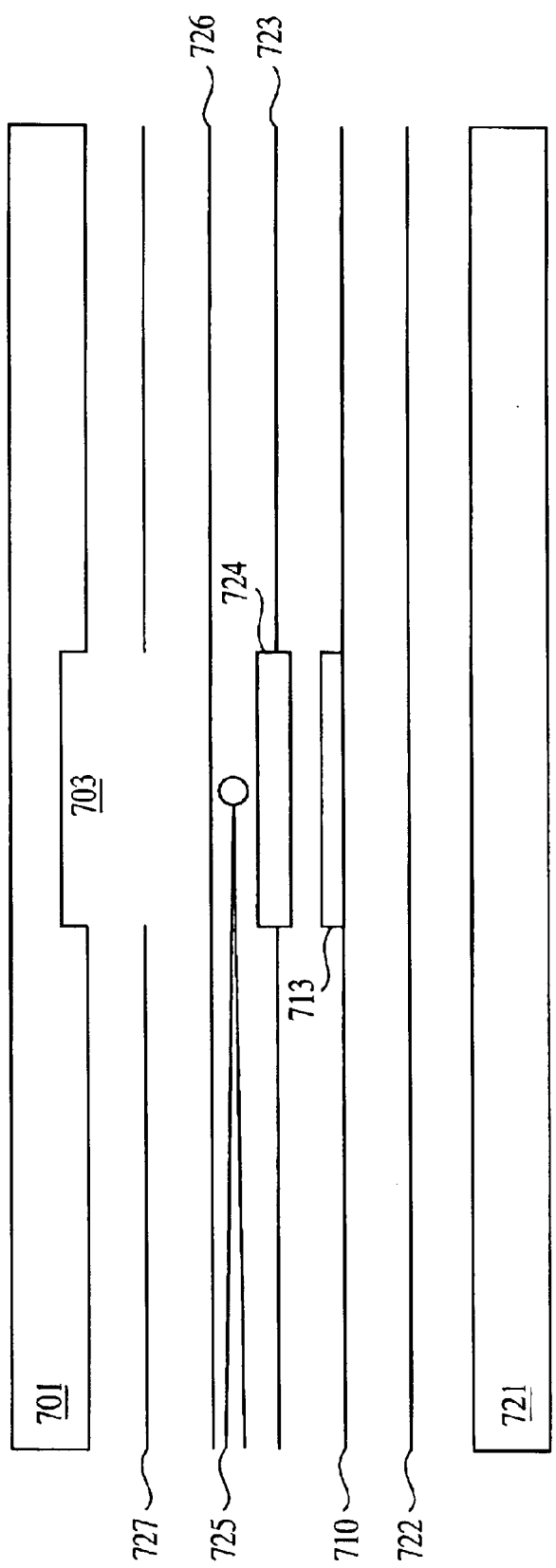
FIG. 25 shows a cross-sectional view on the disk shown in FIG. 6.

FIG. 25 is a cross-sectional view of a cycling chamber, bond layers, and resistive heater. The fluidics disk 701 is mated to a 0.1 mm thick mylar sheet 726 (ICI part #ST505) using double sided tape 727 (3M part #7953MP). The double sided tape is removed from the area under the reaction chamber to minimize reaction contamination from the tape. The mylar layer 726 is mated to the electrical circuit layer 710 using double sided tape 723. These two layers are radially aligned to ensure that the reaction chamber array lines up with the resistive heater array. A thermally conductive elastomer 724 (Bergquist part # CPU Pad) is inserted between the resistive heater 713 and mylar sheet 726 to minimize possible thermal gradients across the cycling chamber. A 0.1 mm thermocouple 725 (Omega part # CHAL 005-type K), to be used for temperature cycling control, is inserted between the mylar sheet 726 and conductive elastomer 724. The electrical circuit layer 710 is mated to a bottom polycarbonate support disk 721 using double sided tape 722.

The microfluidic structures were manufactured through machining of polycarbonate disks using a Light Machines VMC5000 milling machine running "Benchman" software (Light Machines Corporation, Manchester, N.H.). Structures were designed using a computer drafting program and converted to computer machine code. The disc was cleaned with ethanol and then air, then polished by exposure to vapor from boiling methylene chloride to remove surface imperfections.

The electrical circuit disk was fabricated with screen-printing techniques known by those skilled in the art and also specifically disclosed in U.S. Pat. No. 6,063,589. Carbon-based resistive ink (Dupont, 7102/7082 blend) was used to print the resistive heaters, and silver-based ink (Dupont, 5028) was used to print the conductive leads onto 0.1 mm thick mylar sheet.

The instrument used for controlling the rotational profile and thermal cycling consisted of a personal computer, interface electronics between the PC and a servo-controlled drive motor and interface electronics between the PC and the screen-printed circuit. For this example, the spindle is driven by a servo-controlled DC motor with encoder (Micromo, 3557K012CR). A serial port converter a (J. R. Kerr, Z232-485) and motor control board a (J. R. Kerr, PIC-SERVO) provide a communication interface between the PC and motor. A slipring (Litton, AC6023-24) provided the electrical connection between the rotating platform and the stationary control system. The temperature-dependent voltage measured by the thermocouple was converted to current using a miniature transmitter (Omega part # TX91A) and output through the slip ring. This current was converted to a voltage and read with a commercially available analog/digital board (Computer Boards part # CIO-DAS 1600) within the PC. The voltage across the resistive heater was also applied through the slip-ring and was varied to drive the temperature to the desired temperature.

A constant power control loop was used to control reaction chamber temperature. Empirical data showed that to maintain temperatures from 60C to 100C required power from 0.4W to 1.2W. In this example, the PC software control program read the thermocouple temperature and output a control voltage proportional to the setpoint temperature. This voltage was input to a constant power circuit, which was in series with the resistive heater. As temperature increased, heater resistance increased. To maintain constant power, the circuit decreased its output current. Cooling at zero power was provided by convection from the exposed surfaces of the platform and was aided by rotating the disk at a constant speed of 500 rpm. Heating rates were as high as 1.5C/sec and cooling rates were 1.0C/sec.

The disk was mounted on to the motor spindle through a center hole in the disc 705. The slip ring was secured to the top of the disk using a screw. The slip ring lined up with the electric circuit layer so that the appropriate power control and temperature measurement leads were connected.

The solutions PCR consisted of deionized water, E. coli genomic template (Sigma, St. Louis, Mo.), primer set EBGA that amplifies a 215 base pair portion of the beta-galactosidase codon of the E. coli genomic DNA (Research Genetics) and Ready-to-Go beads (Amersham Pharmacia). The EBGA forward sequence is given by 5'-ACCTGCATCACCAGCTGCTT-3' (SEQ ID No.: 7) and the EBGA reverse sequence is given by 5'-CGATGATCCTCATTGCFTATTCTC-3' (SEQ ID No.: 8). Denaturation, annealing, extension temperatures were chosen to be 95° C., 60° C. and 72° C., respectively. The PC software setpoints were 100° C., 60° C., and 72° C. The difference between setpoint and obtained temperatures is expected based on the location of the thermocouple beneath the reaction chamber and the temperature gradient through the disk.

Figure 26:
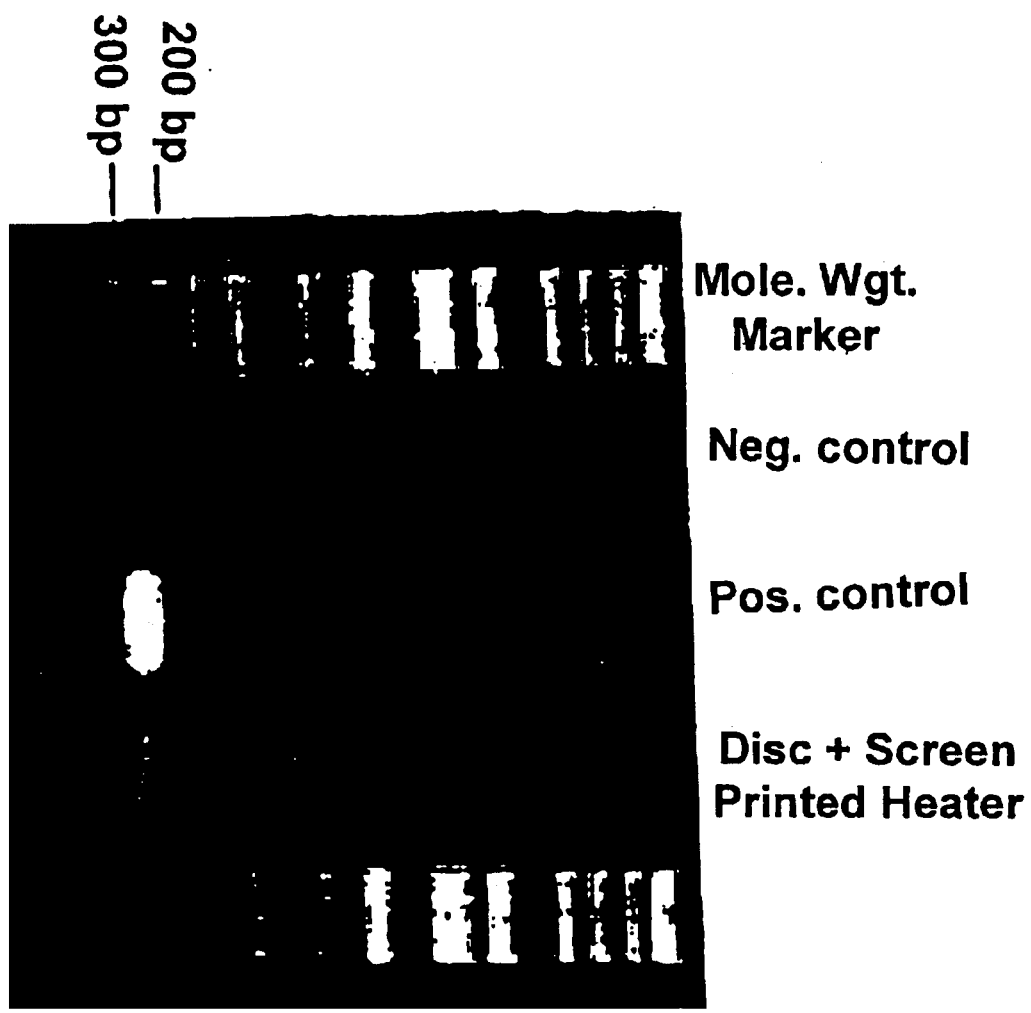
FIG. 26 is a photograph of gel electrophoretic analysis of amplified DNA target from an *E. coli* sample using the disk pictured in FIG. 6.

FIG. 26 shows the gel electrophoresis output after running 30 cycles in this system. The results compare favorably with amplification performed on a commercial thermal cycler (M J Research model # PTC-100), also shown in this gel.

It should be understood that the foregoing disclosure emphasizes certain specific embodiments of the invention and that all modifications or alternatives equivalent thereto are within the spirit and scope of the invention.

What is claimed is:

1. A centripetally-motivated microsystems platform for performing a DNA sample preparation comprising:
   a) a rotatable platform comprising a substrate having a surface comprising one or a multiplicity of microfluidics structures embedded in the surface of the platform, wherein each microfluidics structure comprises
      i) a sample input port fluidly connected to
      ii) a cell lysis chamber in thermal contact with a temperature control element, wherein the cell lysis chamber comprises a filter element having a porosity that retains cell debris and precipitated proteins and nucleic acids in the chamber,
      iii) a lysis buffer reservoir containing a lysis buffer, fluidly connected to the cell lysis chamber by a microchannel;
      iv) a precipitation buffer reservoir, fluidly connected to the cell lysis chamber by a microchannel that comprises a sacrificial valve;
      v) a DNA binding chamber, fluidly connected to the cell lysis chamber by a microchannel, wherein the microchannel is interrupted by a sacrificial valve, wherein the DNA binding chamber further comprises
      vi) a DNA binding filter having a binding affinity for DNA;
      vii) one or a multiplicity of wash buffer reservoirs, wherein each reservoir contains a wash buffer, and wherein each reservoir is fluidly connected to the DNA binding chamber by a microchannel that is interrupted by a sacrificial valve;
      viii) a waste reservoir fluidly connected to the DNA binding chamber by a microchannel;
      ix) a sample recovery chamber, fluidly connected to the DNA binding chamber by a microchannel interrupted by a sacrificial valve; and
      x) an elution buffer reservoir, fluidly connected to the DNA binding chamber by a microchannel interrupted by a sacrificial valve;
   wherein fluid flow through the microfluidic structures is motivated by centripetal force resulting from rotation of the platform and fluid flow through microchannels interrupted by sacrificial valves is dependent on the integrity of these valves.

2. A microsystem platform of claim 1 wherein the cell lysis chamber has a volumetric capacity of from about 50 μL to about 1000 μL.

3. A microsystem platform of claim 1 wherein the lysis buffer reservoir has a volumetric capacity of from about 25 μL to about 300 μL.

4. A microsystem platform of claim 1 wherein the precipitation buffer reservoir has a volumetric capacity of from about 35 μL to about 400 μL.

5. A microsystem platform of claim 1 herein each of the wash buffer reservoirs has a volumetric capacity of from about 50 μL to about 850 μL.

6. A microsystem platform of claim 1 wherein the elution buffer reservoir has a volumetric capacity of from about 20 μL to about 250 μL.

7. A microsystem platform of claim 1 wherein the waste reservoir has a volumetric capacity of from about 350 μL to about 1500 μL.

8. A microsystem platform of claim 1 wherein the DNA binding chamber has a volumetric capacity of from about 5 μL to about 20 μL.

9. A microsystem platform of claim 1 wherein the sample collection chamber has a volumetric capacity of from about 20 μL to about 250 μL.

10. A microsystems platform of claim wherein the sample recovery chamber further comprises a sample outlet port.

11. A microsystems platform of claim 1 wherein the cell lysis chamber further comprises one or a multiplicity of mixing baffles.

12. A microsystems platform of claim 1 wherein the filter contained in the cell lysis chamber is positioned proximal to the microchannel connecting the cell lysis chamber to the DNA binding chamber, wherein fluid must flow through the filter to enter the microchannel.

13. A microsystems platform of claim 1 wherein the DNA binding filter contained in the DNA binding chamber is positioned proximal to the microchannel connecting the DNA binding chamber to the waste reservoir and the sample collection chamber, wherein fluid must flow through the filter to enter the microchannel.

14. A microsystems platform of claim 1 wherein the microchannel connecting the DNA binding chamber to the waste reservoir is the same microchannel that connects the DNA binding chamber to the sample collection chamber, wherein fluid flows through the portion of the microchannel fluidly connected to the waste reservoir only when the sacrificial valve interrupting the portion of the microchannel fluidly connecting the DNA binding chamber to the sample collection chamber is intact.

15. A microsystems platform according to claim 1, wherein each of the sacrificial valves is a wax valve that is in thermal contact with a heating element capable of producing sufficient heat to melt the wax and open the valve.

16. A microsystems platform according to claim 15, wherein each sacrificial valve further comprises a recrystallization chamber having a cross-sectional dimension sufficient to contain the wax comprising the wax valve and permit fluid flow through the microchannel.

17. A microsystems platform according to claim 1, wherein the cell lysis chamber is in thermal contact with a heating element.

18. A microsystems platform according to claim 17, further comprising an electric platen comprising a substrate bearing one or a multiplicity of temperature control elements, wherein each of the temperature control elements is electrically connected to at least two electrical leads, and wherein the electrical leads are connected to a power source through a slip ring;
wherein the substrate comprising the cell lysis chamber is separate from the platen and wherein the temperature control element is in thermal contact with the cell lysis chamber.

19. A centripetally-motivated Microsystems platform for performing an in vitro amplification reaction comprising:
   a) a rotatable platform comprising a substrate having a surface comprising one or a multiplicity of microfluidics structures embedded in the surface of the platform, wherein each microfluidics structure comprises
      i) a sample chamber comprising a sample input port;
      ii) a cell lysis buffer reservoir containing a cell lysis buffer;
      iii) a neutralization buffer reservoir containing a neutralization buffer that is fluidly connected to a first reservoir by a microchannel;
      iv) a first mixing microchannel fluidly connected to the sample buffer chamber and the cell lysis buffer reservoir, wherein the first mixing microchannel defines a longitudinal path in the surface of the platform having a length sufficient to mix the sample and the cell lysis buffer to a lysed cell mixture, wherein the first mixing microchannel is fluidly connected to
      v) a second reservoir, wherein the first and second reservoirs are fluidly connected to
      vi) a second mixing microchannel wherein the second mixing microchannel defines a longitudinal path in the surface of the platform having a length sufficient to mix the lysed cell mixture and the neutralization buffer to a DNA sample mixture, wherein the first mixing microchannel is fluidly connected to
      vii) a third reservoir; wherein the platform further comprises
      viii) a fourth reservoir containing a solution comprising a DNA amplification reagent mixture, wherein the third and fourth reservoirs are fluidly connected to
      ix) a third mixing microchannel wherein the third mixing microchannel defines a longitudinal path in the surface of the platform having a length sufficient to mix the DNA sample mixture and the DNA amplification reagent mixture to produce a DNA amplification reaction mixture, wherein the third mixing microchannel is fluidly connected to
      x) a thermal cycling chamber in thermal contact with
      xi) a temperature control element fluid within the microchannels of the platform is moved through said microchannels by centripetal force arising from rotational motion of the platform for a time and a rotational velocity sufficient to move the fluid through the microchannels and wherein DNA amplification is performed in the thermal cycling chamber by alternating the temperature to denature template DNA, anneal primers and extend the primers with a polymerase.

20. A microsystem platform of claim 19 wherein the sample chamber has a volumetric capacity of from about 2 nL to about 1000 $\mu$L.

21. A microsystem platform of claim 19 wherein the cell lysis buffer reservoir has a volumetric capacity of from about 2 nL to about 1000 $\mu$L.

22. A microsystem platform of claim 19 wherein the neutralization buffer reservoir has a volumetric capacity of from about 2 nL to about 1000 $\mu$L.

23. A microsystem platform of claim 19 wherein each of the first, second, third and fourth reservoirs has a volumetric capacity of from about 2 nL to about 1000 $\mu$L.

24. A microsystem platform of claim 19 wherein the cell lysis buffer reservoir, the neutralization buffer reservoir and the third and fourth reservoirs each further comprise an input port.

25. A microsystem platform of claim 19 wherein each mixing microchannel comprises a plurality of bends having angles greater than 90°.

26. A microsystem platform of claim 19 wherein the flow rate of fluid through each of the mixing microchannels is from about 1 nL/s to about 100 $\mu$L/s.

27. A microsystems platform of claim 19 wherein the thermal cycling chamber further comprises a sample outlet port.

28. A microsystems platform according to claim 19, further comprising an electric platen comprising a substrate bearing one or a multiplicity of temperature control elements, wherein each of the temperature control elements is electrically connected to at least two electrical leads, and wherein the electrical leads are connected to a power source through a slip ring;
wherein the substrate comprising the thermal cycling chamber is separate from the platen and wherein the temperature control element is in thermal contact with the thermal cycling chamber.

29. A microsystems platform according to claim 1, wherein the interior surfaces of the microfluidic structures are coated with parylene.

30. A microsystems platform according to claim 19, wherein the interior surfaces of the microfluidic structures are coated with parylene.

* * * * *